United States Patent
Runtz-Schmitt et al.

(10) Patent No.: US 10,479,796 B2
(45) Date of Patent: Nov. 19, 2019

(54) SPIRO-OXAZOLONES

(71) Applicant: Hoffmann-La Roche Inc., Little Falls, NJ (US)

(72) Inventors: Valerie Runtz-Schmitt, Rixheim (FR); Patrick Schnider, Bottmingen (CH); Cosimo Dolente, Allschwil (CH); Bernhard Fasching, Basel (CH)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/174,674

(22) Filed: Jun. 6, 2016

(65) Prior Publication Data

US 2017/0008901 A1 Jan. 12, 2017

Related U.S. Application Data

(63) Continuation of application No. PCT/EP2014/077858, filed on Dec. 16, 2014.

(30) Foreign Application Priority Data

Dec. 19, 2013 (EP) .................... 13198604

(51) Int. Cl.
| | |
|---|---|
| *C07D 491/107* | (2006.01) |
| *C07D 491/10* | (2006.01) |
| *C07D 491/12* | (2006.01) |
| *C07D 498/10* | (2006.01) |
| *C07D 491/20* | (2006.01) |
| *C07D 519/00* | (2006.01) |

(52) U.S. Cl.
CPC ....... *C07D 491/107* (2013.01); *C07D 491/10* (2013.01); *C07D 491/12* (2013.01); *C07D 491/20* (2013.01); *C07D 498/10* (2013.01); *C07D 519/00* (2013.01)

(58) Field of Classification Search
CPC ................................. C07D 491/107
USPC .......................................... 514/278
See application file for complete search history.

(56) References Cited

U.S. PATENT DOCUMENTS

2010/0120751 A1    5/2010   Bissantz et al.

FOREIGN PATENT DOCUMENTS

| CN | 2008/161299 A1 | 9/2009 |
|---|---|---|
| CN | 2008/167333 | 10/2009 |
| CN | 2008/171760 | 11/2009 |
| CN | 2010/120751 A1 | 10/2011 |
| EP | 1566384 * | 6/2009 |
| WO | 2008/068159 A1 | 6/2008 |
| WO | 2008/077811 A1 | 7/2008 |

OTHER PUBLICATIONS

Fabio et al. Frontiers in CNS Drug Discovery, 2010, vol. 1, pp. 156-183 (Year: 2010).*
Lippard. Nature (2002) vol. 416, pp. 587 (Year: 2002).*
International Search Report for International Patent Application No. PCT/EP2014/077858.
Schnur et al., "Spiro Oxazolidinedione Aldose Reductase Inhibitors" J. Med. Chem. 25:1451-1454 ( 1982).

* cited by examiner

*Primary Examiner* — Savitha M Rao
*Assistant Examiner* — Taina D Matos Negron
(74) *Attorney, Agent, or Firm* — Robert C. Hall

(57) ABSTRACT

The present invention provides spiro-oxazolones, which act as V1a receptor modulators, and in particular as V1a receptor antagonists, their manufacture, pharmaceutical compositions containing them and their use as medicaments. The present compounds are useful as therapeutics acting peripherally and centrally in the conditions of inappropriate secretion of vasopressin, anxiety, depressive disorders, obsessive compulsive disorder, autistic spectrum disorders, schizophrenia, aggressive behavior and phase shift sleep disorders, in particular jetlag.

13 Claims, No Drawings

SPIRO-OXAZOLONES

RELATED APPLICATION DATA

This application is a Continuation of International Application No. PCT/EP2014/077858 filed on Dec. 16, 2014, which claims priority to EP Application No. 13198604.4 filed on Dec. 19, 2013, the disclosures of which are incorporated herein by reference in their entirety.

The present invention provides spiro-oxazolones, which act as V1a receptor modulators, and in particular as V1a receptor antagonists, their manufacture, pharmaceutical compositions containing them and their use as medicaments. The present compounds are useful as therapeutics acting peripherally and centrally in the conditions of inappropriate secretion of vasopressin, anxiety, depressive disorders, obsessive compulsive disorder, autistic spectrum disorders, schizophrenia, aggressive behavior and phase shift sleep disorders, in particular jetlag.

TECHNICAL FIELD

The present invention provides a compound of formula I,

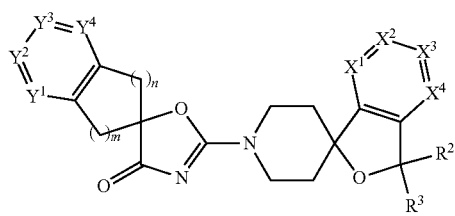

wherein the substituents and variables are as described below and in the claims, or a pharmaceutically acceptable salt thereof.

The present compounds are V1a receptor antagonists, useful for the treatment of autistic spectrum disorders.

BACKGROUND ART

Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water reabsorption and mediates the antidiuretic effects of vasopressin (Robben, et al.)[1]. Compounds with activity at the V2 receptor may therefore cause side-effects on blood homeostasis.

The oxytocin receptor is related to the Vasopressin receptor family and mediates the effects of the neurohormone oxytocin in the brain and the periphery. Oxytocin is believed to have central anxiolytic effects (Neumann)[2]. Central oxytocin receptor antagonism might therefore lead to anxiogenic effects, which are regarded as undesired side-effects.

In the brain vasopressin acts as a neuromodulator and is elevated in the amygdala during stress (Ebner, et al.)[3]. It is known that stressful life events can trigger major depression and anxiety (Kendler, et al.)[4] and that both have very high comorbidity, with anxiety often preceding major depression (Regier, et al.)[5]. The V1a receptor is extensively expressed in the brain and particularly in limbic areas like the amygdala, lateral septum and hippocampus which are playing an important role in the regulation of anxiety. Indeed V1a knock-out mice show a reduction in anxious behavior in the plus-maze, open field and light-dark box (Bielsky, et al.)[6]. The down-regulation of the V1a receptor using antisense oligonucleotide injection in the septum also causes a reduction in anxious behavior (Landgraf, et al.)[7]. Vasopressin or the V1a receptor are also implicated in other neuropsychological disorders: genetic studies linked sequence polymorphism in the promoter of the human V1a receptor to autistic spectrum disorders (Yirmiya, et al.)[8], intranasal administration of vasopressin was shown to influence aggression in human males (Thompson, et al.)[9] and vasopressin levels were found to be elevated in schizophrenic patients (Raskind, et al.)[10] and patients with obsessive-compulsive disorder (Altemus, et al.)[11].

Autistic Spectrum Disorders (ASD) are a clinically heterogeneous condition characterized by defects in socialization and language. ASD include a wide range of abnormalities including a genuine incapacity to organize affective relations, behavioral anomalies in reciprocal social interactions, verbal and non-verbal communication, limited interest in the surrounding environment associated with stereotyped movements and repetitive plays (Bourreau et al, 2009)[12]. Research to date indicates that a genetic predisposition may be involved, but also environmental factors have to be taken into consideration (Bourgeron, 2009)[13]. There is at present no efficient biological/pharmaceutical treatment to ASD.

The suprachiasmatic nucleus (SCN) is the endogenous clock of the body regulating circadian rhythmicity and is known to be rich in vasopressin neurons (Kalsbeek et al. 2010)[14], producing and releasing vasopressin with a 24 h circadian rhythm (Schwartz et al. 1983)[15]. A major regulatory effect of vasopressin on circadian rhythm could not be demonstrated by the prior art. The Brattleboro rat, a rat strain naturally lacking vasopressin due to a point mutation, has no obvious defect in its circadian rhythm (Groblewski et al. 1981)[16]. Injection of vasopressin directly in the hamster SCN had no effect on circadian phase shift (Albers et al. 1984)[17]. In contrast, the vasopressin receptors were shown to modulate the circadian clock in a more subtle way. Yamaguchi et at (2013)[18] demonstrated that V1a knock-out and V1a/V1b double knock-out mice show faster reentrainment to the new light/dark cycle after a circadian phase advance or a phase delay, an experiment mimicking jet-lag in humans. The same result was obtained after chronic administration of a mixture of V1a and V1b small molecule antagonists through a minipump directly on the SCN.

DETAILED DESCRIPTION OF THE INVENTION

Object of the present invention is a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with modulation of the V1a receptor, and in particular with V1a receptor antagonism. A further object of the invention is to provide selective inhibitors of the V1a receptor, since selectivity for the V1a receptor is expected to afford a low potential to cause unwanted off-target related side effects such as discussed above.

The following definitions of the general terms used in the present description apply irrespectively of whether the terms in question appear alone or in combination with other groups.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular "$C_{1-6}$-alkyl" groups have 1 to 4 carbon atoms ("$C_{1-4}$-alkyl"). A specific group is methyl.

The term "halogen-$C_{1-6}$-alkyl", alone or in combination with other groups, refers to $C_{1-6}$-alkyl as defined herein, which is substituted by one or multiple halogen, in particular 1-5 halogen, more particular 1-3 halogen ("halogen-$C_{1-3}$-alkyl"), specific 1 halogen or 3 halogen. Particular halogen is fluoro. Particular "halogen-$C_{1-6}$-alkyl" is "fluoro-$C_{1-6}$-alkyl". Examples are $CH_2F$, $CHF_2$ and $CF_3$.

The term "hydroxy", alone or in combination with other groups, refers to —OH.

The term "halogen", alone or in combination with other groups, denotes chloro (Cl), iodo (I), fluoro (F) and bromo (Br).

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" groups have 1 to 4 carbon atoms ("$C_{1-4}$-alkoxy"). A specific group is OMe.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Particular acids are formic acid, trifluoroacetic acid and hydrochloric acid. Particular are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. In particular it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to $pK_i$ values ($-\log K_i$), in which higher values indicate exponentially greater potency.

The term "antagonist" denotes a compound that diminishes or prevents the action of another compound as defined e.g. in Goodman and Gilman's "The Pharmacological Basis of Therapeutics, 7th ed." in page 35, Macmillan Publ. Company, Canada, 1985. In particular, antagonists refer to a compound that attenuates the effect of an agonist. A "competitive antagonist" binds to the same site of a receptor as the agonist but does not activate the receptor, thus blocks the agonist's action. A "non-competitive antagonist" binds to an allosteric (non-agonist) site on the receptor to prevent activation of the receptor. A "reversible antagonist" binds non-covalently to the receptor, therefore can be "washed out". An "irreversible antagonist" binds covalently to the receptor and cannot be displaced by either competing ligands or washing.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC[19].

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The terms "Autistic Spectrum" and "Autistic Spectrum Disorders" summarize conditions classified as pervasive developmental disorders, which include but are not limited to autism, Asperger syndrome, pervasive developmental disorder not otherwise specified (PDD-NOS), childhood disintegrative disorder, Rett syndrome and Fragile X, in particular autism. These disorders are typically characterized by social deficits, communication difficulties, stereotyped or repetitive behaviors and interests, and cognitive delays.

The term "phase shift sleep disorders" summarizes conditions classified as disturbances in the circadian rhythm, i.e. the approximately 24-hour cycles that are generated by an organism, e.g. a human being. Phase shift sleep disorders include, but are not limited to transient disorders like jetlag or a changed sleep schedule due to work, social responsibilities, or illness, as well as chronic disorders like delayed sleep-phase syndrome (DSPS), delayed sleep-phase type (DSPT), advanced sleep-phase syndrome (ASPS), and irregular sleep-wake cycle.

The phrase "whereby only one of $X^1$, $X^2$, $X^3$ and $X^4$ is N" mean that maximal one of $X^{1-4}$ is N and the remaining residues are each individually C—$R^1$, or that all $X^{1-4}$ are each individually C—$R^1$.

The phrase "whereby only one of $Y^1$, $Y^2$, $Y^3$ and $Y^4$ is N" mean that maximal one of $Y^{1-4}$ is N and the remaining residues are each individually C—$R^4$, or that all $Y^{1-4}$ are each individually C—$R^4$.

In detail, the present invention provides compounds of the general formula I

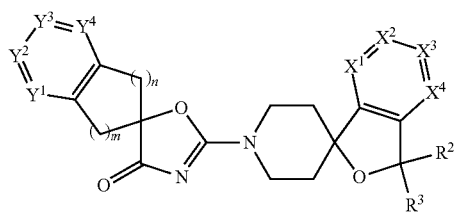

wherein
$X^1$ is C—$R^1$ or N;
$X^2$ is C—$R^1$ or N;
$X^3$ is C—$R^1$ or N;
$X^4$ is C—$R^1$ or N;
whereby only one of $X^1$, $X^2$, $X^3$ and $X^4$ is N;
$R^1$ each separately is selected from the group consisting of hydrogen, halogen, hydroxy, $C_{1-6}$-alkyl and $C_{1-6}$-alkoxy;
$R^2$ is selected from the group consisting of H and $C_{1-6}$-alkyl;
$R^3$ is selected from the group consisting of H and $C_{1-6}$-alkyl;
or $R^2$ and $R^3$ together are =O;
$Y^1$ is C—$R^4$ or N;
$Y^2$ is C—$R^4$ or N;
$Y^3$ is C—$R^4$ or N;
$Y^4$ is C—$R^4$ or N;
whereby only one of $Y^1$, $Y^2$, $Y^3$ and $Y^4$ is N;
$R^4$ each separately is selected from the group consisting of hydrogen, halogen, halogen-$C_{1-6}$-alkyl, hydroxy, $C_{1-6}$-alkyl, $C_{1-6}$-alkoxy and Si($C_{1-6}$-alkyl)$_3$;
m is 1, 2 or 3; and
n is 0 or 1;
or pharmaceutically acceptable salts thereof.

A certain embodiment of this invention refers to a compound of formula I as described herein, wherein
$X^1$ is C—H or N;
$X^2$ is C—$R^1$ or N;
$X^3$ is C—$R^1$;
$X^4$ is C—H or N;
whereby only one of $X^1$, $X^2$, $X^3$ and $X^4$ is N;
$R^1$ each separately is selected from the group consisting of hydrogen, halogen, hydroxy, and $C_{1-6}$-alkyl;
$R^2$ is selected from the group consisting of H and $C_{1-6}$-alkyl;
$R^3$ is selected from the group consisting of H and $C_{1-6}$-alkyl;
or $R^2$ and $R^3$ together are =O;
$Y^1$ is C—H or N;
$Y^2$ is C—$R^4$ or N;
$Y^3$ is C—$R^4$ or N;
$Y^4$ is C—H or N;
whereby only one of $Y^1$, $Y^2$, $Y^3$ and $Y^4$ is N;
$R^4$ each separately is selected from the group consisting of hydrogen, halogen, hydroxy and $C_{1-6}$-alkyl;
m is 1; and
n is 1.

A certain embodiment of this invention refers to a compound of formula I as described herein, wherein
$X^1$, $X^2$, $X^3$ and $X^4$ are each CH;
$R^2$ is selected from the group consisting of H and $C_{1-6}$-alkyl;
$R^3$ is selected from the group consisting of H and $C_{1-6}$-alkyl;
or $R^2$ and $R^3$ together are =O;
m and n are each 1;
$Y^1$ and $Y^4$ are each CH; and
$Y^2$ and $Y^3$ are each CF.

A certain embodiment of this invention refers to a compound of formula I as described herein, wherein
$X^1$, $X^2$, $X^3$ and $X^4$ are each CH;
$R^2$ and $R^3$ are each H;
m and n are each 1;
$Y^1$ and $Y^4$ are each CH; and
$Y^2$ and $Y^3$ are each CF.

A certain embodiment of this invention refers to an intermediate of a compound of formula I as described herein, wherein
$X^1$ is C—$R^1$;
$X^2$ is C—$R^1$;
$X^3$ is C—$R^1$;
$X^4$ is C—$R^1$ or NO;
$R^1$ each separately is selected from the group consisting of hydrogen, halogen, hydroxy, $C_{1-6}$-alkyl and $C_{1-6}$-alkoxy;
$R^2$ is selected from the group consisting of H and $C_{1-6}$-alkyl;
$R^3$ is selected from the group consisting of H and $C_{1-6}$-alkyl;
or $R^2$ and $R^3$ together are =O;
$Y^1$ is C—$R^4$ or N;
$Y^2$ is C—$R^4$ or N;
$Y^3$ is C—$R^4$ or N;
$Y^4$ is C—$R^4$ or N;
whereby only one of $Y^1$, $Y^2$, $Y^3$ and $Y^4$ is N;
$R^4$ each separately is selected from the group consisting of hydrogen, halogen, halogen-$C_{1-6}$-alkyl, hydroxy, $C_{1-6}$-alkyl, $C_{1-6}$-alkoxy and Si($C_{1-6}$-alkyl)$_3$;
m is 1, 2 or 3; and
n is 0 or 1;
or pharmaceutically acceptable salts thereof.

A certain embodiment of this invention refers to an intermediate of a compound of formula I as described herein, wherein
$X^1$, $X^2$ and $X^3$ are each CH and $X^4$ is NO;
$R^2$ and $R^3$ are each $C_{1-6}$-alkyl;
m and n are each 1; and
$Y^1$, $Y^2$, $Y^3$ and $Y^4$ are each CH.

A certain embodiment of this invention refers to an intermediate of a compound of formula I as described herein, wherein
$X^1$, $X^2$ and $X^3$ are each CH and $X^4$ is NO;
$R^2$ and $R^3$ are each H;
m and n are each 1; and
$Y^1$, $Y^2$, $Y^3$ and $Y^4$ are each CH.

A certain embodiment of this invention refers to a compound of formula I as described herein, wherein $X^1$ is CH, or C-halogen.

A certain embodiment of this invention refers to a compound of formula I as described herein, wherein $X^1$ is CH, C—Cl or C—F.

A certain embodiment of this invention refers to a compound of formula I as described herein, wherein $X^1$ is CH.

A certain embodiment of this invention refers to a compound of formula I as described herein, wherein $X^2$ is CH, C-halogen, C—$C_{1-6}$-alkyl, C—$C_{1-6}$-alkoxy or C—OH.

A certain embodiment of this invention refers to a compound of formula I as described herein, wherein $X^2$ is CH, C—Cl, C—$CH_3$, C—$OCH_3$ or C—OH.

A certain embodiment of this invention refers to a compound of formula I as described herein, wherein $X^2$ is CH.

A certain embodiment of this invention refers to a compound of formula I as described herein, wherein $X^3$ is CH, C-halogen, C—$C_{1-6}$-alkyl, C—$C_{1-6}$-alkoxy or C—OH.

A certain embodiment of this invention refers to a compound of formula I as described herein, wherein $X^3$ is CH, C—Br, C—Cl, C—F, C—$CH_3$, C—$OCH_3$ or C—OH.

A certain embodiment of this invention refers to a compound of formula I as described herein, wherein $X^3$ is CH.

A certain embodiment of this invention refers to a compound of formula I as described herein, wherein $X^4$ is CH, C-halogen or C—$C_{1-6}$-alkyl.

A certain embodiment of this invention refers to a compound of formula I as described herein, wherein $X^4$ is CH, C-Me or C—F.

A certain embodiment of this invention refers to a compound of formula I as described herein, wherein $X^4$ is CH.

A certain embodiment of this invention refers to a compound of formula I as described herein, wherein $X^1$, $X^2$, $X^3$ and $X^4$ are each CH.

A certain embodiment of this invention refers to a compound of formula I as described herein, wherein $X^2$, $X^3$ and $X^4$ are each CH and $X^1$ is N.

A certain embodiment of this invention refers to a compound of formula I as described herein, wherein $X^1$, $X^3$ and $X^4$ are each CH and $X^2$ is N.

A certain embodiment of this invention refers to a compound of formula I as described herein, wherein $X^1$, $X^2$ and $X^4$ are each CH and $X^3$ is N.

A certain embodiment of this invention refers to a compound of formula I as described herein, wherein $X^1$, $X^2$ and $X^3$ are each CH and $X^4$ is N.

A certain embodiment of this invention refers to a compound of formula I as described herein, wherein $R^2$ is H or $C_{1-6}$-alkyl.

A certain embodiment of this invention refers to a compound of formula I as described herein, wherein $R^2$ is H or Me.

A certain embodiment of this invention refers to a compound of formula I as described herein, wherein $R^2$ is H.

A certain embodiment of this invention refers to a compound of formula I as described herein, wherein $R^3$ is H or $C_{1-6}$-alkyl.

A certain embodiment of this invention refers to a compound of formula I as described herein, wherein $R^3$ is H or Me.

A certain embodiment of this invention refers to a compound of formula I as described herein, wherein $R^3$ is H.

A certain embodiment of this invention refers to a compound of formula I as described herein, wherein $R^2$ and $R^3$ together are =O.

A certain embodiment of this invention refers to a compound of formula I as described herein, wherein m is 1 and n is 0 or 1.

A certain embodiment of this invention refers to a compound of formula I as described herein, wherein m is 1 and n is 1.

A certain embodiment of this invention refers to a compound of formula I as described herein, wherein m is 2 and n is 0 or 1.

A certain embodiment of this invention refers to a compound of formula I as described herein, wherein m is 3 and n is 0.

A certain embodiment of this invention refers to a compound of formula I as described herein, wherein $Y^1$ is CH.

A certain embodiment of this invention refers to a compound of formula I as described herein, wherein $Y^2$ is CH, C-halogen, C—$C_{1-6}$-alkyl, C—$C_{1-6}$-alkoxy or C—OH.

A certain embodiment of this invention refers to a compound of formula I as described herein, wherein $Y^2$ is CH, C—F, C—$CH_3$, C—$OCH_3$ or C—OH.

A certain embodiment of this invention refers to a compound of formula I as described herein, wherein $Y^2$ is CH.

A certain embodiment of this invention refers to a compound of formula I as described herein, wherein $Y^3$ is CH, C-halogen, C-halogen-$C_{1-6}$-alkyl, C—$C_{1-6}$-alkyl, C—$C_{1-6}$-alkoxy, C—OH or Si($C_{1-6}$-alkyl)$_3$.

A certain embodiment of this invention refers to a compound of formula I as described herein, wherein $Y^3$ is CH, C—$CH_2Cl$, C—$CH_2F$, C—$CHF_2$, C—Cl, C—F, C—$CH_3$, C—$OCH_3$, C—OH or C—Si$(CH_3)_3$.

A certain embodiment of this invention refers to a compound of formula I as described herein, wherein $Y^3$ is CH.

A certain embodiment of this invention refers to a compound of formula I as described herein, wherein $Y^4$ is CH.

A certain embodiment of this invention refers to a compound of formula I as described herein, wherein $Y^1$, $Y^2$, $Y^3$ and $Y^4$ are each CH.

A certain embodiment of this invention refers to a compound of formula I as described herein, wherein $Y^1$, $Y^3$ and $Y^4$ are each CH and $Y^2$ is N.

A certain embodiment of this invention refers to a compound of formula I as described herein, wherein $X^1$, $X^2$ and $X^3$ are each CH and $X^4$ is N, $R^2$ and $R^3$ are each $C_{1-6}$-alkyl, $R^2$ and $R^3$ are each $C_{1-6}$-alkyl, m and n are each 1 and $Y^1$, $Y^2$, $Y^3$ and $Y^4$ are each CH.

A certain embodiment of this invention refers to a compound of formula I as described herein, selected from the group consisting of (1R)-2'-(1'H,3H-spiro[2-benzofuran-1,4'-piperidin]-1'-yl)-2,3-dihydro-4'H-spiro[indene-1,5'-[1,3]oxazol]-4'-one, (1S)-2'-(1'H,3H-spiro[2-benzofuran-1,4'-piperidin]-1'-yl)-2,3-dihydro-4'H-spiro[indene-1,5'-[1,3]oxazol]-4'-one, 1'-(4'-oxo-1,3-dihydro-4'H-spiro[indene-2,5'-[1,3]oxazol]-2'-yl)-3H-spiro[2-benzofuran-1,4'-piperidin]-3-one, 1'-(4'-oxo-3,4-dihydro-1H,4'H-spiro[naphthalene-2,5'-[1,3]oxazol]-2'-yl)-1'H,3H-spiro[2-benzofuran-1,4'-piperidin]-3-one, 1'-(4'-oxo-3,4-dihydro-2H,4'H-spiro[naphthalene-1,5'-[1,3]oxazol]-2'-yl)-3H-spiro[2-benzofuran-1,4'-piperidin]-3-one, 1'-(5,6-difluoro-4'-oxo-1,3-dihydro-4'H-spiro[indene-2,5'-[1,3]oxazol]-2'-yl)-3H-spiro[2-benzofuran-1,4'-piperidin]-3-one, 1'-(5,6-dihydroxy-4'-oxo-1,3-dihydro-4'H-spiro[indene-2,5'-[1,3]oxazol]-2'-yl)-3H-spiro[2-benzofuran-1,4'-piperidin]-3-one, 1'-(5,6-dimethoxy-4'-oxo-1,3-dihydro-4'H-spiro[indene-2,5'-[1,3]oxazol]-2'-yl)-3H-spiro[2-benzofuran-1,4'-piperidin]-3-one, 1'-(5,6-dimethyl-4'-oxo-1,3-dihydro-4'H-spiro[indene-2,5'-[1,3]oxazol]-2'-yl)-3H-spiro[2-benzofuran-1,4'-piperidin]-3-one, 1'-(5-hydroxy-4'-oxo-1,3-dihydro-4'H-spiro[indene-2,5'-[1,3]oxazol]-2'-yl)-3H-spiro[2-benzofuran-1,4'-piperidin]-3-one, 1'-(5-methoxy-4'-oxo-1,3-dihydro-4'H-spiro[indene-2,5'-[1,3]oxazol]-2'-yl)-3H-spiro[2-benzofuran-1,4'-piperidin]-3-one, 1'-(5-methyl-4'-oxo-1,3-dihydro-4'H-spiro[indene-2,5'-[1,3]oxazol]-2'-yl)-3H-spiro[2-benzofuran-1,4'-piperidin]-3-one, 1'-[(2R)-4'-oxo-3,4-dihydro-1H,4'H-spiro[naphthalene-2,5'-[1,3]oxazol]-2'-yl]-1'H,3H-spiro[2-benzofuran-1,4'-piperidin]-3-one, 1'-[(2R)-5-methyl-4'-oxo-1,3-dihydro-4'H-spiro[indene-2,5'-[1,3]oxazol]-2'-yl]-3H-spiro[2-benzofuran-1,4'-piperidin]-3-one, 1'-[(2S)-4'-oxo-3,4-dihydro-1H,4'H-spiro[naphthalene-2,5'-[1,3]oxazol]-2'-yl]-1'H,3H-spiro[2-benzofuran-1,4'-piperidin]-3-one, 1'-[(2S)-5-methyl-4'-oxo-1,3-dihydro-4'H-spiro[indene-2,5'-[1,3]oxazol]-2'-yl]-3H-spiro[2-benzofuran-1,4'-piperidin]-3-one, 2'-(1'H,3H-spiro[2-benzofuran-1,4'-piperidin]-1'-yl)-1,3-dihydro-4'H-spiro[indene-2,5'-[1,3]oxazol]-4'-one, 2'-(1'H,3H-spiro[2-benzofuran-1,4'-piperidin]-1'-yl)-3-(trifluoromethyl)-5,7-dihydro-4'H-spiro[cyclopenta[c]pyridine-6,5'-[1,3]oxazol]-4'-one, 2'-(1'H,3H-spiro[2-benzofuran-1,4'-piperidin]-1'-yl)-3,4-dihydro-2H,4'H-spiro[naphthalene-1,5'-[1,3]oxazol]-4'-one, 2'-(1'H,3H-spiro[2-benzofuran-1,4'-piperidin]-1'-yl)-3,4-dihydro-1H,4'H-spiro[naphthalene-2,5'-[1,3]oxazol]-4'-one, 2'-(1'H,3H-spiro[2-benzofuran-1,4'-piperidin]-1'-yl)-5-(trimethylsilyl)-1,3-dihydro-4'H-spiro[indene-2,5'-[1,3]oxazol]-4'-one, 2'-(1'H,3H-spiro[2-benzofuran-1,4'-piperidin]-1'-yl)-5,7-dihydro-4'H-spiro[cyclopenta[b]pyridine-6,5'-[1,3]oxazol]-4'-one, 2'-(2-hydroxy-7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one, 2'-(2-methyl-1'H,5H-spiro[furo[3,4-b]pyridine-7,4'-piperidin]-1'-yl)-1,3-dihydro-4'H-spiro[indene-2,5'-[1,3]oxazol]-4'-one, 2'-(2-methyl-1'H,7H-spiro[furo[3,4-b]pyridine-5,4'-piperidin]-1'-yl)-1,3-dihydro-4'H-spiro[indene-2,5'-[1,3]oxazol]-4'-one, 2'-(3,3-dimethyl-1'H,3H-spiro[2-benzofuran-1,4'-piperidin]-1'-yl)-1,3-dihydro-4'H-spiro[indene-2,5'-[1,3]oxazol]-4'-one, 2'-(3-hydroxy-7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one, 2'-(3-methyl-1'H,5H-spiro[furo[3,4-b]pyridine-7,4'-piperidin]-1'-yl)-1,3-dihydro-4'H-spiro[indene-2,5'-[1,3]oxazol]-4'-one, 2'-(3-methyl-1'H,7H-spiro[furo[3,4-b]pyridine-5,4'-piperidin]-1'-yl)-1,3-dihydro-4'H-spiro[indene-2,5'-[1,3]oxazol]-4'-one, 2'-(4-methyl-1'H,3H-spiro[2-benzofuran-1,4'-piperidin]-1'-yl)-1,3-dihydro-4'H-spiro[indene-2,5'-[1,3]oxazol]-4'-one, 2'-(5,5-dimethyl-1'H,5H-spiro[furo[3,4-b]pyridine-7,4'-piperidin]-1'-yl)-1,3-dihydro-4'H-spiro[indene-2,5'-[1,3]oxazol]-4'-one, 2'-(6-methyl-1H,1'H-spiro[furo[3,4-c]pyridine-3,4'-piperidin]-1'-yl)-1,3-dihydro-4'H-spiro[indene-2,5'-[1,3]oxazol]-4'-one, 2'-(6-methyl-1'H,3H-spiro[furo[3,4-c]pyridine-1,4'-piperidin]-1'-yl)-1,3-dihydro-4'H-spiro[indene-2,5'-[1,3]oxazol]-4'-one, 2'-(7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one, 2'-(7,7-dimethyl-1'H,7H-spiro[furo[3,4-b]pyridine-5,4'-piperidin]-1'-yl)-5-methoxy-1,3-dihydro-4'H-spiro[indene-2,5'-[1,3]oxazol]-4'-one, 2'-(7,7-dimethyl-1'H,7H-spiro[furo[3,4-b]pyridine-5,4'-piperidin]-1'-yl)-5-hydroxy-1,3-dihydro-4'H-spiro[indene-2,5'-[1,3]oxazol]-4'-one, 2'-(7,7-dimethyl-1'H,7H-spiro[furo[3,4-b]pyridine-5,4'-piperidin]-1'-yl)-4-methoxy-1,3-dihydro-4'H-spiro[indene-2,5'-[1,3]oxazol]-4'-one, 2'-(7,7-dimethyl-1'H,7H-spiro[furo[3,4-b]pyridine-5,4'-piperidin]-1'-yl)-4-hydroxy-1,3-dihydro-4'H-spiro[indene-2,5'-[1,3]oxazol]-4'-one, 2'-(7,7-dimethyl-1-oxido-1'H,7H-spiro[furo[3,4-b]pyridine-5,4'-piperidin]-1'-yl)-1,3-dihydro-4'H-spiro[indene-2,5'-[1,3]oxazol]-4'-one, 2-methyl-1'-(4'-oxo-1,3-dihydro-4'H-spiro[indene-2,5'-[1,3]oxazol]-2'-yl)-5H-spiro[furo[3,4-b]pyridine-7,4'-piperidin]-5-one, 2-methyl-1'-(4'-oxo-1,3-dihydro-4'H-spiro[indene-2,5'-[1,3]oxazol]-2'-yl)-7H-spiro[furo[3,4-b]pyridine-5,4'-piperidin]-7-one, 2'-spiro[5H-furo[3,4-b]pyridine-7,4'-piperidine]-1'-ylspiro[indane-2,5'-oxazole]-4'-one, 2'-spiro[7H-furo[3,4-b]pyridine-5,4'-piperidine]-1'-ylspiro[indane-2,5'-oxazole]-4'-one, 3-(chloromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one, 3-(difluoromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one, 3-(fluoromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one, 3-methyl-1'-(4'-oxo-1,3-dihydro-4'H-spiro[indene-2,5'-[1,3]oxazol]-2'-yl)-5H-spiro[furo[3,4-b]pyridine-7,4'-piperidin]-5-one, 3-methyl-1'-(4'-oxo-1,3-dihydro-4'H-spiro[indene-2,5'-[1,3]oxazol]-2'-yl)-7H-spiro[furo[3,4-b]pyridine-5,4'-piperidin]-7-one, 3-methyl-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one, 4-chloro-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one, 4-fluoro-1'-(4'-oxo-1,3-dihydro-4'H-spiro[indene-2,5'-[1,3]oxazol]-2'-yl)-3H-spiro[2-benzofuran-1,4'-piperidin]-3-one, 4-methyl-1'-(4'-oxo-1,3-dihydro-4'H-spiro[indene-2,5'-[1,3]oxazol]-2'-yl)-3H-spiro[2-benzofuran-1,4'-piperidin]-3-one, 5,6-difluoro-2'-(1'H,3H-spiro[2-benzofuran-1,4'-piperidin]-1'-yl)-1,3-dihydro-4'H-spiro[indene-2,5'-[1,3]oxazol]-4'-one, 5,6-dihydroxy-1'-(4'-oxo-1,3-dihydro-4'H-spiro[indene-2, 5'-[1,3]oxazol]-2'-yl)-3H-spiro[2-benzofuran-1,4'-piperidin]-3-one, 5,6-dimethoxy-1'-(4'-oxo-1,3-dihydro-4'H-spiro[indene-2, 5'-[1,3]oxazol]-2'-yl)-3H-spiro[2-benzofuran-1,4'-piperidin]-3-one, 5,6-dimethyl-2'-(1'H,3H-spiro[2-benzofuran-1,4'-piperidin]-1'-yl)-1,3-dihydro-4'H-spiro[indene-2,5'-[1,3]oxazol]-4'-one, 5-bromo-1'-(4'-oxo-1,3-dihydro-4'H-spiro[indene-2,5'-[1,3] oxazol]-2'-yl)-3H-spiro[2-benzofuran-1,4'-piperidin]-3-one, 5-chloro-2'-(1'H,3H-spiro[2-benzofuran-1,4'-piperidin]-1'-yl)-1,3-dihydro-4'H-spiro[indene-2,5'-[1,3]oxazol]-4'-one, 5-fluoro-1'-(4'-oxo-1,3-dihydro-4'H-spiro[indene-2,5'-[1,3] oxazol]-2'-yl)-3H-spiro[2-benzofuran-1,4'-piperidin]-3-one, 5-fluoro-2'-(1'H,3H-spiro[2-benzofuran-1,4'-piperidin]-1'-yl)-1,3-dihydro-4'H-spiro[indene-2,5'-[1,3]oxazol]-4'-one, 5-hydroxy-1'-(4'-oxo-1,3-dihydro-4'H-spiro[indene-2,5'-[1, 3]oxazol]-2'-yl)-3H-spiro[2-benzofuran-1,4'-piperidin]-3-one, 5-methoxy-1'-(4'-oxo-1,3-dihydro-4'H-spiro[indene-2,5'-[1, 3]oxazol]-2'-yl)-3H-spiro[2-benzofuran-1,4'-piperidin]-3-one, 5-methyl-1'-(4'-oxo-1,3-dihydro-4'H-spiro[indene-2,5'-[1,3] oxazol]-2'-yl)-3H-spiro[2-benzofuran-1,4'-piperidin]-3-one, 5-methyl-2'-(1'H,3H-spiro[2-benzofuran-1,4'-piperidin]-1'-yl)-1,3-dihydro-4'H-spiro[indene-2,5'-[1,3]oxazol]-4'-one, 6-chloro-1'-(4'-oxo-1,3-dihydro-4'H-spiro[indene-2,5'-[1,3] oxazol]-2'-yl)-3H-spiro[2-benzofuran-1,4'-piperidin]-3-one, 6-chloro-1'-(4'-oxo-1,3-dihydro-4'H-spiro[indene-2,5'-[1,3] oxazol]-2'-yl)-1H-spiro[furo[3,4-c]pyridine-3,4'-piperidin]-1-one, 6-hydroxy-1'-(4'-oxo-1,3-dihydro-4'H-spiro[indene-2,5'-[1, 3]oxazol]-2'-yl)-3H-spiro[2-benzofuran-1,4'-piperidin]-3-one, 6-methoxy-1'-(4'-oxo-1,3-dihydro-4'H-spiro[indene-2,5'-[1, 3]oxazol]-2'-yl)-3H-spiro[2-benzofuran-1,4'-piperidin]-3-one, 6-methyl-1'-(4'-oxo-1,3-dihydro-4'H-spiro[indene-2,5'-[1,3] oxazol]-2'-yl)-3H-spiro[2-benzofuran-1,4'-piperidin]-3-one, 6-methyl-1'-(4'-oxo-1,3-dihydro-4'H-spiro[indene-2,5'-[1,3] oxazol]-2'-yl)-1H-spiro[furo[3,4-c]pyridine-3,4'-piperidin]-1-one, 6-methyl-1'-(4'-oxo-1,3-dihydro-4'H-spiro[indene-2,5'-[1,3] oxazol]-2'-yl)-3H-spiro[furo[3,4-c]pyridine-1,4'-piperidin]-3-one, and 7-fluoro-1'-(4'-oxo-1,3-dihydro-4'H-spiro[indene-2,5'-[1,3] oxazol]-2'-yl)-3H-spiro[2-benzofuran-1,4'-piperidin]-3-one.

A certain embodiment of this invention refers to a compound of formula I as described herein, selected from the group consisting of (+)-2'-(1'H,3H-spiro[2-benzofuran-1,4'-piperidin]-1'-yl)-2, 3-dihydro-4'H-spiro[indene-1,5'-[1,3]oxazol]-4'-one, (−)-2'-(1'H,3H-spiro[2-benzofuran-1,4'-piperidin]-1'-yl)-2, 3-dihydro-4'H-spiro[indene-1,5'-[1,3]oxazol]-4'-one, 1'-(4'-oxo-1,3-dihydro-4'H-spiro[indene-2,5'-[1,3]oxazol]-2'-yl)-3H-spiro[2-benzofuran-1,4'-piperidin]-3-one, 1'-(4'-oxo-3,4-dihydro-1H,4'H-spiro[naphthalene-2,5'-[1,3] oxazol]-2'-yl)-1'H,3H-spiro[2-benzofuran-1,4'-piperidin]-3-one, 1'-(4'-oxo-3,4-dihydro-2H,4'H-spiro[naphthalene-1,5'-[1,3] oxazol]-2'-yl)-3H-spiro[2-benzofuran-1,4'-piperidin]-3-one, 1'-(5,6-difluoro-4'-oxo-1,3-dihydro-4'H-spiro[indene-2,5'-[1,3]oxazol]-2'-yl)-3H-spiro[2-benzofuran-1,4'-piperidin]-3-one, 1'-(5,6-dihydroxy-4'-oxo-1,3-dihydro-4'H-spiro[indene-2, 5'-[1,3]oxazol]-2'-yl)-3H-spiro[2-benzofuran-1,4'-piperidin]-3-one, 1'-(5,6-dimethoxy-4'-oxo-1,3-dihydro-4'H-spiro[indene-2, 5'-[1,3]oxazol]-2'-yl)-3H-spiro[2-benzofuran-1,4'-piperidin]-3-one, 1'-(5,6-dimethyl-4'-oxo-1,3-dihydro-4'H-spiro[indene-2,5'-[1,3]oxazol]-2'-yl)-3H-spiro[2-benzofuran-1,4'-piperidin]-3-one, 1'-(5-hydroxy-4'-oxo-1,3-dihydro-4'H-spiro[indene-2,5'-[1, 3]oxazol]-2'-yl)-3H-spiro[2-benzofuran-1,4'-piperidin]-3-one, 1'-(5-methoxy-4'-oxo-1,3-dihydro-4'H-spiro[indene-2,5'-[1, 3]oxazol]-2'-yl)-3H-spiro[2-benzofuran-1,4'-piperidin]-3-one, 1'-(5-methyl-4'-oxo-1,3-dihydro-4'H-spiro[indene-2,5'-[1,3] oxazol]-2'-yl)-3H-spiro[2-benzofuran-1,4'-piperidin]-3-one, 1'-[4'-oxo-3,4-dihydro-1H,4'H-spiro[naphthalene-2,5'-[1,3] oxazol]-2'-yl]-1'H,3H-spiro[2-benzofuran-1,4'-piperidin]-3-one enantiomer A, 1'-[4'-oxo-3,4-dihydro-1H,4'H-spiro[naphthalene-2,5'-[1,3] oxazol]-2'-yl]-1'H,3H-spiro[2-benzofuran-1,4'-piperidin]-3-one enantiomer B, (−)-1'-[5-methyl-4'-oxo-1,3-dihydro-4'H-spiro[indene-2,5'-[1,3]oxazol]-2'-yl]-3H-spiro[2-benzofuran-1,4'-piperidin]-3-one, (+)-1'-[5-methyl-4'-oxo-1,3-dihydro-4'H-spiro[indene-2,5'-[1,3]oxazol]-2'-yl]-3H-spiro[2-benzofuran-1,4'-piperidin]-3-one, 2'-(1'H,3H-spiro[2-benzofuran-1,4'-piperidin]-1'-yl)-1,3-dihydro-4'H-spiro[indene-2,5'-[1,3]oxazol]-4'-one, 2'-(1'H,3H-spiro[2-benzofuran-1,4'-piperidin]-1'-yl)-3-(trifluoromethyl)-5,7-dihydro-4'H-spiro[cyclopenta[c]pyridine-6,5'-[1,3]oxazol]-4'-one, 2'-(1'H,3H-spiro[2-benzofuran-1,4'-piperidin]-1'-yl)-3,4-dihydro-2H,4'H-spiro[naphthalene-1,5'-[1,3]oxazol]-4'-one, 2'-(1'H,3H-spiro[2-benzofuran-1,4'-piperidin]-1'-yl)-3,4-dihydro-1H,4'H-spiro[naphthalene-2,5'-[1,3]oxazol]-4'-one, 2'-(1'H,3H-spiro[2-benzofuran-1,4'-piperidin]-1'-yl)-5-(trimethylsilyl)-1,3-dihydro-4'H-spiro[indene-2,5'-[1,3] oxazol]-4'-one, 2'-(1'H,3H-spiro[2-benzofuran-1,4'-piperidin]-1'-yl)-5,7-dihydro-4'H-spiro[cyclopenta[b]pyridine-6,5'-[1,3]oxazol]-4'-one, 2'-(2-methyl-1'H,5H-spiro[furo[3,4-b]pyridine-7,4'-piperidin]-1'-yl)-1,3-dihydro-4'H-spiro[indene-2,5'-[1,3]oxazol]-4'-one, 2'-(2-methyl-1'H,7H-spiro[furo[3,4-b]pyridine-5,4'-piperidin]-1'-yl)-1,3-dihydro-4'H-spiro[indene-2,5'-[1,3]oxazol]-4'-one, 2'-(3,3-dimethyl-1'H,3H-spiro[2-benzofuran-1,4'-piperidin]-1'-yl)-1,3-dihydro-4'H-spiro[indene-2,5'-[1,3]oxazol]-4'-one, 2'-(3-methyl-1'H,5H-spiro[furo[3,4-b]pyridine-7,4'-piperidin]-1'-yl)-1,3-dihydro-4'H-spiro[indene-2,5'-[1,3]oxazol]-4'-one,
2'-(3-methyl-1'H,7H-spiro[furo[3,4-b]pyridine-5,4'-piperidin]-1'-yl)-1,3-dihydro-4'H-spiro[indene-2,5'-[1,3]oxazol]-4'-one,
2'-(4-methyl-1'H,3H-spiro[2-benzofuran-1,4'-piperidin]-1'-yl)-1,3-dihydro-4'H-spiro[indene-2,5'-[1,3]oxazol]-4'-one,
2'-(5,5-dimethyl-1'H,5H-spiro[furo[3,4-b]pyridine-7,4'-piperidin]-1'-yl)-1,3-dihydro-4'H-spiro[indene-2,5'-[1,3]oxazol]-4'-one,
2'-(6-methyl-1H,1'H-spiro[furo[3,4-c]pyridine-3,4'-piperidin]-1'-yl)-1,3-dihydro-4'H-spiro[indene-2,5'-[1,3]oxazol]-4'-one,
2'-(6-methyl-1'H,3H-spiro[furo[3,4-c]pyridine-1,4'-piperidin]-1'-yl)-1,3-dihydro-4'H-spiro[indene-2,5'-[1,3]oxazol]-4'-one,
2'-(7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one,
2'-(7,7-dimethyl-1'H,7H-spiro[furo[3,4-b]pyridine-5,4'-piperidin]-1'-yl)-5-methoxy-1,3-dihydro-4'H-spiro[indene-2,5'-[1,3]oxazol]-4'-one,
2'-(7,7-dimethyl-1'H,7H-spiro[furo[3,4-b]pyridine-5,4'-piperidin]-1'-yl)-5-hydroxy-1,3-dihydro-4'H-spiro[indene-2,5'-[1,3]oxazol]-4'-one,
2-methyl-1'-(4'-oxo-1,3-dihydro-4'H-spiro[indene-2,5'-[1,3]oxazol]-2'-yl)-5H-spiro[furo[3,4-b]pyridine-7,4'-piperidin]-5-one,
2-methyl-1'-(4'-oxo-1,3-dihydro-4'H-spiro[indene-2,5'-[1,3]oxazol]-2'-yl)-7H-spiro[furo[3,4-b]pyridine-5,4'-piperidin]-7-one,
2'-(1'H,5H-spiro[furo[3,4-b]pyridine-7,4'-piperidin]-1'-yl)-1,3-dihydro-4'H-spiro[indene-2,5'-[1,3]oxazol]-4'-one,
2'-(1'H,7H-spiro[furo[3,4-b]pyridine-5,4'-piperidin]-1'-yl)-1,3-dihydro-4'H-spiro[indene-2,5'-[1,3]oxazol]-4'-one,
3-(chloromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one,
3-(difluoromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one,
3-(fluoromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one,
3-methyl-1'-(4'-oxo-1,3-dihydro-4'H-spiro[indene-2,5'-[1,3]oxazol]-2'-yl)-5H-spiro[furo[3,4-b]pyridine-7,4'-piperidin]-5-one,
3-methyl-1'-(4'-oxo-1,3-dihydro-4'H-spiro[indene-2,5'-[1,3]oxazol]-2'-yl)-7H-spiro[furo[3,4-b]pyridine-5,4'-piperidin]-7-one,
3-methyl-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one,
4-chloro-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one,
4-fluoro-1'-(4'-oxo-1,3-dihydro-4'H-spiro[indene-2,5'-[1,3]oxazol]-2'-yl)-3H-spiro[2-benzofuran-1,4'-piperidin]-3-one,
4-methyl-1'-(4'-oxo-1,3-dihydro-4'H-spiro[indene-2,5'-[1,3]oxazol]-2'-yl)-3H-spiro[2-benzofuran-1,4'-piperidin]-3-one,
5,6-difluoro-2'-(1'H,3H-spiro[2-benzofuran-1,4'-piperidin]-1'-yl)-1,3-dihydro-4'H-spiro[indene-2,5'-[1,3]oxazol]-4'-one,
5,6-dihydroxy-1'-(4'-oxo-1,3-dihydro-4'H-spiro[indene-2,5'-[1,3]oxazol]-2'-yl)-3H-spiro[2-benzofuran-1,4'-piperidin]-3-one,
5,6-dimethoxy-1'-(4'-oxo-1,3-dihydro-4'H-spiro[indene-2,5'-[1,3]oxazol]-2'-yl)-3H-spiro[2-benzofuran-1,4'-piperidin]-3-one,
5,6-dimethyl-2'-(1'H,3H-spiro[2-benzofuran-1,4'-piperidin]-1'-yl)-1,3-dihydro-4'H-spiro[indene-2,5'-[1,3]oxazol]-4'-one,
5-bromo-1'-(4'-oxo-1,3-dihydro-4'H-spiro[indene-2,5'-[1,3]oxazol]-2'-yl)-3H-spiro[2-benzofuran-1,4'-piperidin]-3-one,
5-chloro-2'-(1'H,3H-spiro[2-benzofuran-1,4'-piperidin]-1'-yl)-1,3-dihydro-4'H-spiro[indene-2,5'-[1,3]oxazol]-4'-one,
5-fluoro-1'-(4'-oxo-1,3-dihydro-4'H-spiro[indene-2,5'-[1,3]oxazol]-2'-yl)-3H-spiro[2-benzofuran-1,4'-piperidin]-3-one,
5-fluoro-2'-(1'H,3H-spiro[2-benzofuran-1,4'-piperidin]-1'-yl)-1,3-dihydro-4'H-spiro[indene-2,5'-[1,3]oxazol]-4'-one,
5-hydroxy-1'-(4'-oxo-1,3-dihydro-4'H-spiro[indene-2,5'-[1,3]oxazol]-2'-yl)-3H-spiro[2-benzofuran-1,4'-piperidin]-3-one,
5-methoxy-1'-(4'-oxo-1,3-dihydro-4'H-spiro[indene-2,5'-[1,3]oxazol]-2'-yl)-3H-spiro[2-benzofuran-1,4'-piperidin]-3-one,
5-methyl-1'-(4'-oxo-1,3-dihydro-4'H-spiro[indene-2,5'-[1,3]oxazol]-2'-yl)-3H-spiro[2-benzofuran-1,4'-piperidin]-3-one,
5-methyl-2'-(1'H,3H-spiro[2-benzofuran-1,4'-piperidin]-1'-yl)-1,3-dihydro-4'H-spiro[indene-2,5'-[1,3]oxazol]-4'-one,
6-chloro-1'-(4'-oxo-1,3-dihydro-4'H-spiro[indene-2,5'-[1,3]oxazol]-2'-yl)-3H-spiro[2-benzofuran-1,4'-piperidin]-3-one,
6-chloro-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one,
6-hydroxy-1'-(4'-oxo-1,3-dihydro-4'H-spiro[indene-2,5'-[1,3]oxazol]-2'-yl)-3H-spiro[2-benzofuran-1,4'-piperidin]-3-one,
6-methoxy-1'-(4'-oxo-1,3-dihydro-4'H-spiro[indene-2,5'-[1,3]oxazol]-2'-yl)-3H-spiro[2-benzofuran-1,4'-piperidin]-3-one,
6-methyl-1'-(4'-oxo-1,3-dihydro-4'H-spiro[indene-2,5'-[1,3]oxazol]-2'-yl)-3H-spiro[2-benzofuran-1,4'-piperidin]-3-one,
6-methyl-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one,
6-methyl-1'-(4'-oxo-1,3-dihydro-4'H-spiro[indene-2,5'-[1,3]oxazol]-2'-yl)-3H-spiro[furo[3,4-c]pyridine-1,4'-piperidin]-3-one, and
7-fluoro-1'-(4'-oxo-1,3-dihydro-4'H-spiro[indene-2,5'-[1,3]oxazol]-2'-yl)-3H-spiro[2-benzofuran-1,4'-piperidin]-3-one.

A certain embodiment of this invention refers to a compound of formula I as described herein, selected from the group consisting of
1'-(4'-oxo-1,3-dihydro-4'H-spiro[indene-2,5'-[1,3]oxazol]-2'-yl)-3H-spiro[2-benzofuran-1,4'-piperidin]-3-one,
1'-(5,6-difluoro-4'-oxo-1,3-dihydro-4'H-spiro[indene-2,5'-[1,3]oxazol]-2'-yl)-3H-spiro[2-benzofuran-1,4'-piperidin]-3-one, 1'-(5,6-dihydroxy-4'-oxo-1,3-dihydro-4'H-spiro[indene-2,5'-[1,3]oxazol]-2'-yl)-3H-spiro[2-benzofuran-1,4'-piperidin]-3-one,
1'-(5-hydroxy-4'-oxo-1,3-dihydro-4'H-spiro[indene-2,5'-[1,3]oxazol]-2'-yl)-3H-spiro[2-benzofuran-1,4'-piperidin]-3-one,
1'-[(2R)-5-methyl-4'-oxo-1,3-dihydro-4'H-spiro[indene-2,5'-[1,3]oxazol]-2'-yl]-3H-spiro[2-benzofuran-1,4'-piperidin]-3-one,
2'-(1'H,3H-spiro[2-benzofuran-1,4'-piperidin]-1'-yl)-1,3-dihydro-4'H-spiro[indene-2,5'-[1,3]oxazol]-4'-one,
2'-(3-methyl-1'H,5H-spiro[furo[3,4-b]pyridine-7,4'-piperidin]-1'-yl)-1,3-dihydro-4'H-spiro[indene-2,5'-[1,3]oxazol]-4'-one,
2'-(3-methyl-1'H,7H-spiro[furo[3,4-b]pyridine-5,4'-piperidin]-1'-yl)-1,3-dihydro-4'H-spiro[indene-2,5'-[1,3]oxazol]-4'-one,
2'-(5,5-dimethyl-1'H,5H-spiro[furo[3,4-b]pyridine-7,4'-piperidin]-1'-yl)-1,3-dihydro-4'H-spiro[indene-2,5'-[1,3]oxazol]-4'-one,
2'-(6-methyl-1H,1'H-spiro[furo[3,4-c]pyridine-3,4'-piperidin]-1'-yl)-1,3-dihydro-4'H-spiro[indene-2,5'-[1,3]oxazol]-4'-one,
2'-(7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one,
2'-(7,7-dimethyl-1'H,7H-spiro[furo[3,4-b]pyridine-5,4'-piperidin]-1'-yl)-5-hydroxy-1,3-dihydro-4'H-spiro[indene-2,5'-[1,3]oxazol]-4'-one,
3-methyl-1'-(4'-oxo-1,3-dihydro-4'H-spiro[indene-2,5'-[1,3]oxazol]-2'-yl)-5H-spiro[furo[3,4-b]pyridine-7,4'-piperidin]-5-one,
3-methyl-1'-(4'-oxo-1,3-dihydro-4'H-spiro[indene-2,5'-[1,3]oxazol]-2'-yl)-7H-spiro[furo[3,4-b]pyridine-5,4'-piperidin]-7-one,
5,6-difluoro-2'-(1'H,3H-spiro[2-benzofuran-1,4'-piperidin]-1'-yl)-1,3-dihydro-4'H-spiro[indene-2,5'-[1,3]oxazol]-4'-one,
5,6-dihydroxy-1'-(4'-oxo-1,3-dihydro-4'H-spiro[indene-2,5'-[1,3]oxazol]-2'-yl)-3H-spiro[2-benzofuran-1,4'-piperidin]-3-one,
5-fluoro-1'-(4'-oxo-1,3-dihydro-4'H-spiro[indene-2,5'-[1,3]oxazol]-2'-yl)-3H-spiro[2-benzofuran-1,4'-piperidin]-3-one,
5-hydroxy-1'-(4'-oxo-1,3-dihydro-4'H-spiro[indene-2,5'-[1,3]oxazol]-2'-yl)-3H-spiro[2-benzofuran-1,4'-piperidin]-3-one,
6-hydroxy-1'-(4'-oxo-1,3-dihydro-4'H-spiro[indene-2,5'-[1,3]oxazol]-2'-yl)-3H-spiro[2-benzofuran-1,4'-piperidin]-3-one, and
6-methyl-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one.

A certain embodiment of this invention refers to a compound of formula I as described herein, selected from the group consisting of
2'-(1'H,3H-spiro[2-benzofuran-1,4'-piperidin]-1'-yl)-1,3-dihydro-4'H-spiro[indene-2,5'-[1,3]oxazol]-4'-one,
1'-(4'-oxo-1,3-dihydro-4'H-spiro[indene-2,5'-[1,3]oxazol]-2'-yl)-3H-spiro[2-benzofuran-1,4'-piperidin]-3-one,
2'-(6-methyl-1H,1'H-spiro[furo[3,4-c]pyridine-3,4'-piperidin]-1'-yl)-1,3-dihydro-4'H-spiro[indene-2,5'-[1,3]oxazol]-4'-one,
2'-(3-methyl-1'H,5H-spiro[furo[3,4-b]pyridine-7,4'-piperidin]-1'-yl)-1,3-dihydro-4'H-spiro[indene-2,5'-[1,3]oxazol]-4'-one, and
2'-(3-methyl-1'H,7H-spiro[furo[3,4-b]pyridine-5,4'-piperidin]-1'-yl)-1,3-dihydro-4'H-spiro[indene-2,5'-[1,3]oxazol]-4'-one.

A certain embodiment of this invention refers to a compound of formula I as described herein that is 2'-(1'H,3H-spiro[2-benzofuran-1,4'-piperidin]-1'-yl)-1,3-dihydro-4'H-spiro[indene-2,5'-[1,3]oxazol]-4'-one.

A certain embodiment of this invention refers to a compound of formula I as described herein that is 5,6-difluoro-2'-(1'H,3H-spiro[2-benzofuran-1,4'-piperidin]-1'-yl)-1,3-dihydro-4'H-spiro[indene-2,5'-[1,3]oxazol]-4'-one.

A certain embodiment of this invention refers to a compound of formula I as described herein that is 2'-(7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one.

In a certain embodiment, the invention relates to a process to manufacture a compound of formula (I) comprising the step of reacting a compound of formula (II)

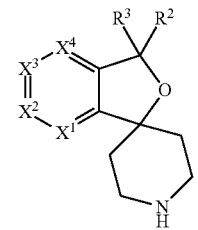

II with a compound of formula (III)

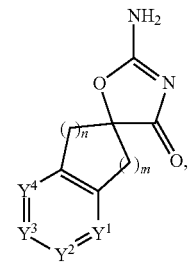

III wherein n, m, $R^2$, $R^3$, $X^{1-4}$ and $Y^{1-4}$ are as defined hereinabove for formula (I).

A certain embodiment of this invention refers to a compound of formula I as described herein, whenever prepared by a process as defined herein.

A certain embodiment of this invention refers to a compound of formula I as described herein for use as therapeutically active substance.

A certain embodiment of this invention refers to a compound of formula I as described herein for the use as therapeutically active substance for the therapeutic and/or prophylactic treatment of diseases and disorders which are associated with V1a receptor antagonism.

A certain embodiment of this invention refers to a compound of formula I as described herein for the use as therapeutically active substance acting peripherally and centrally in the conditions of inappropriate secretion of vasopressin, anxiety, depressive disorders, obsessive compulsive disorder, autistic spectrum disorders, schizophrenia, aggressive behavior and phase shift sleep disorders, in particular jetlag.

A certain embodiment of this invention refers to a pharmaceutical composition comprising a compound of formula I as described herein and a pharmaceutically acceptable carrier and/or a pharmaceutically acceptable auxiliary substance.

A certain embodiment of this invention refers to the use of a compound of formula I as described herein for the manufacture of a medicament for acting peripherally and centrally in the conditions of inappropriate secretion of vasopressin, anxiety, depressive disorders, obsessive compulsive disorder, autistic spectrum disorders, schizophrenia, aggressive behavior and phase shift sleep disorders, in particular jetlag.

A certain embodiment of this invention refers to a method for the use of a compound as described herein, which is acting peripherally and centrally in the conditions of inappropriate secretion of vasopressin, anxiety, depressive disorders, obsessive compulsive disorder, autistic spectrum disorders, schizophrenia, aggressive behavior and phase shift sleep disorders, in particular jetlag, which method comprises administering said compound of formula I to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric centre of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

Compounds of formula 1 can be prepared according to the following processes.

The processes are described in more detail with the following general schemes A to H and general procedures I to XXIII.

Scheme 1: General Scheme A

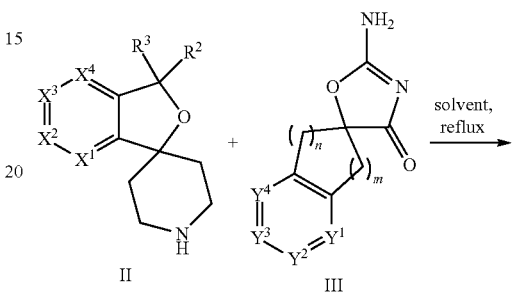

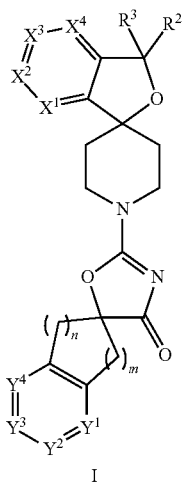

Compounds of formula (I) can be prepared by thermal condensation of a secondary amine of formula (II) and an 2-amino-oxazol-4-one of formula (III). Secondary amines of formula (II) are either commercially available or can be prepared by methods known in the art or described hereinafter. 2-Amino-oxazol-4-ones of formula (III) can be prepared by methods known in the art or described hereinafter. The syntheses of compounds of formulas (II) and (III) are outlined in general schemes D to I hereinafter. General scheme 1 is hereinafter further illustrated by general procedure XXI.

Scheme 2: General Scheme B
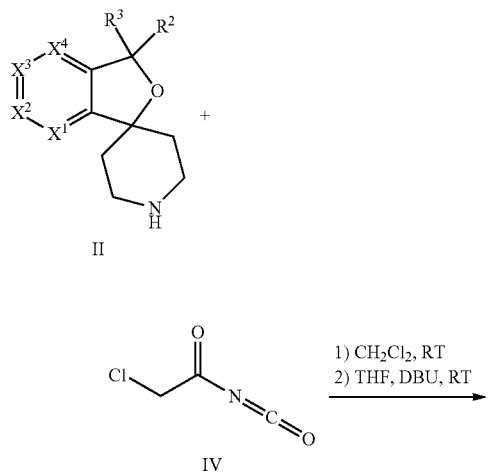
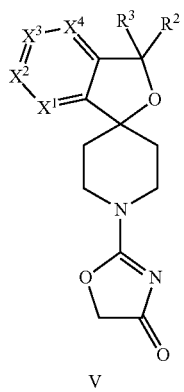
Compounds of formula (V) can be prepared by reaction of a secondary amine of formula (II) and chloroacetyl isocyanate (IV) in dichloromethane and subsequently treatment of the urea-intermediate with 1,8-diazabicyclo[5.4.0]undec-7-ene in tetrahydrofuran at room temperature.
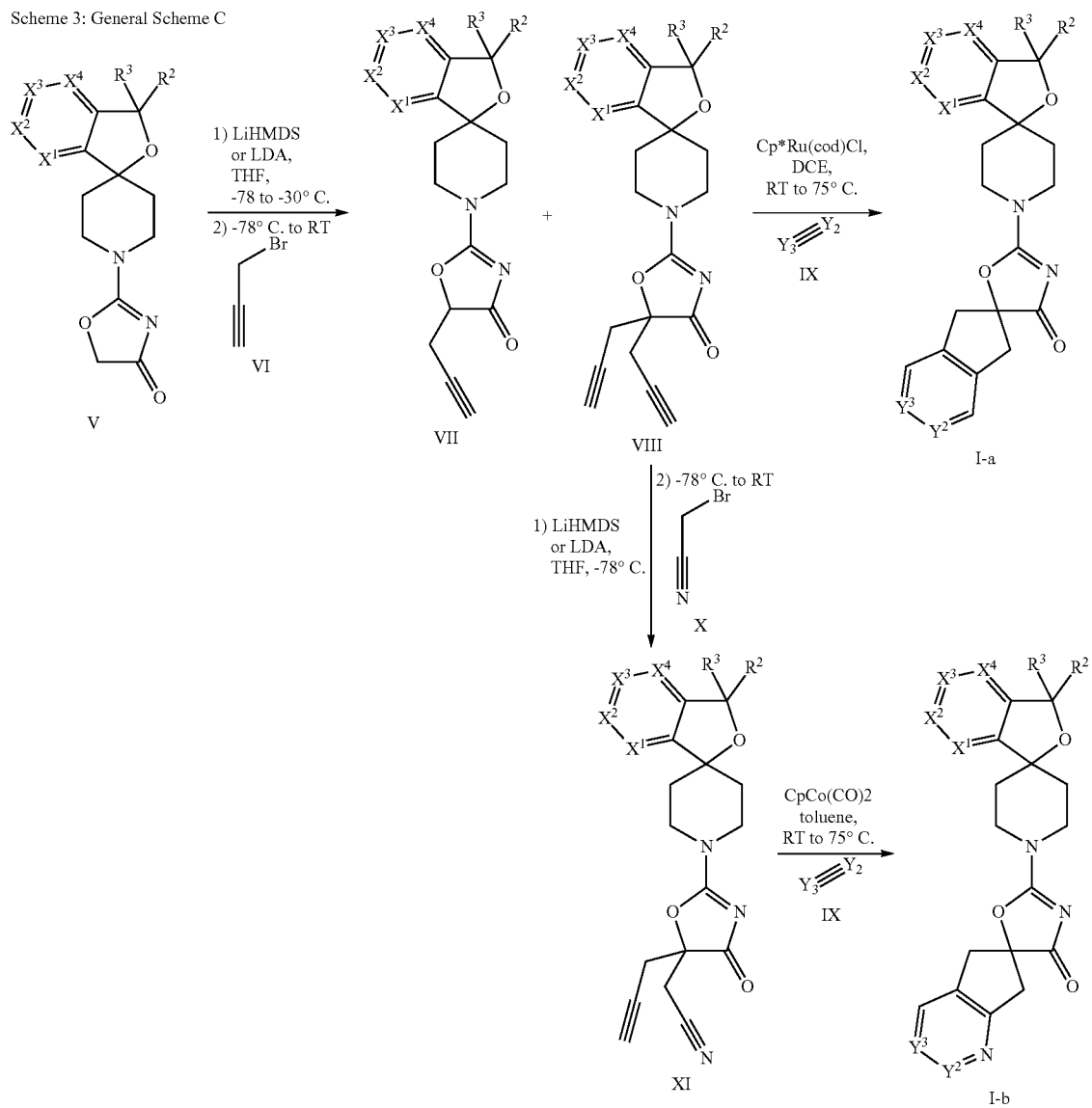

Compounds of formula (VII) and (VIII) can be prepared from compounds of formula (V) according to methods known in the art, e.g. by consecutively treating a compound of formula (V) with an organic base such as lithium diisopropylamide or lithium bis(trimethylsilyl)amide and 3-bromoprop-1-yne (VI). Compounds of formula (I-a) can be prepared by cyclization of a compound of formula (VIII) with alkynes of formula (IX) in a solvent such as 1,2-dichloroethane using a catalyst such as chloro(pentamethylcyclopentadienyl)(cyclooctadiene)ruthenium(II), at temperatures between 0° C. and 75° C. Compounds of formula (XI) can be prepared from compounds of formula (VII) according to methods known in the art, e.g. by consecutively treating a compound of formula (VII) with an organic base such as lithium diisopropylamide or lithium bis(trimethylsilyl)amide and bromoacetonitrile (X). Compounds of formula (I-b) can be prepared by cyclization of a compound of formula (XI) with alkynes of formula (IX) in a solvent such as toluene using a catalyst such as cyclopentadienylcobalt dicarbonyl at temperatures between 0° C. and 75° C. General scheme 3 is hereinafter further illustrated by general procedures XXII and XXIII.

Scheme 4: General Scheme D

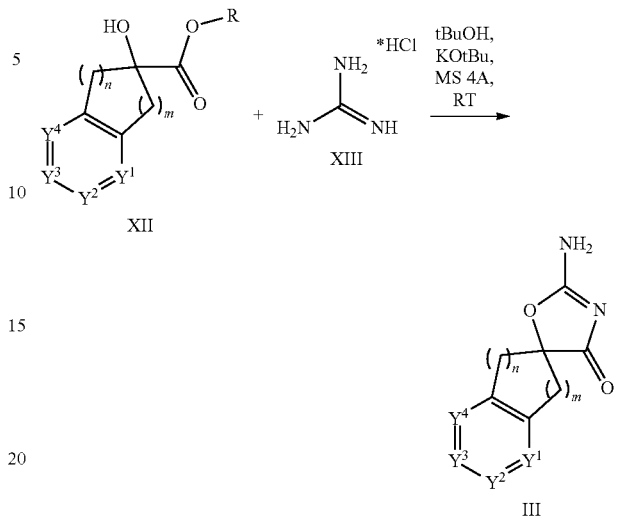

R = Me, Et

2-Amino-oxazol-4-one intermediates of formula (III) can be prepared by cyclization of an alpha-hydroxy ester of formula (XII) with guanidinium hydrochloride (XIII) in an alcohol such as tert-butanol using a base such as potassium tert-butoxide and a drying agent such as molecular sieves 4A. General scheme 4 is hereinafter further illustrated by general procedure XX.

Scheme 5: General Scheme E

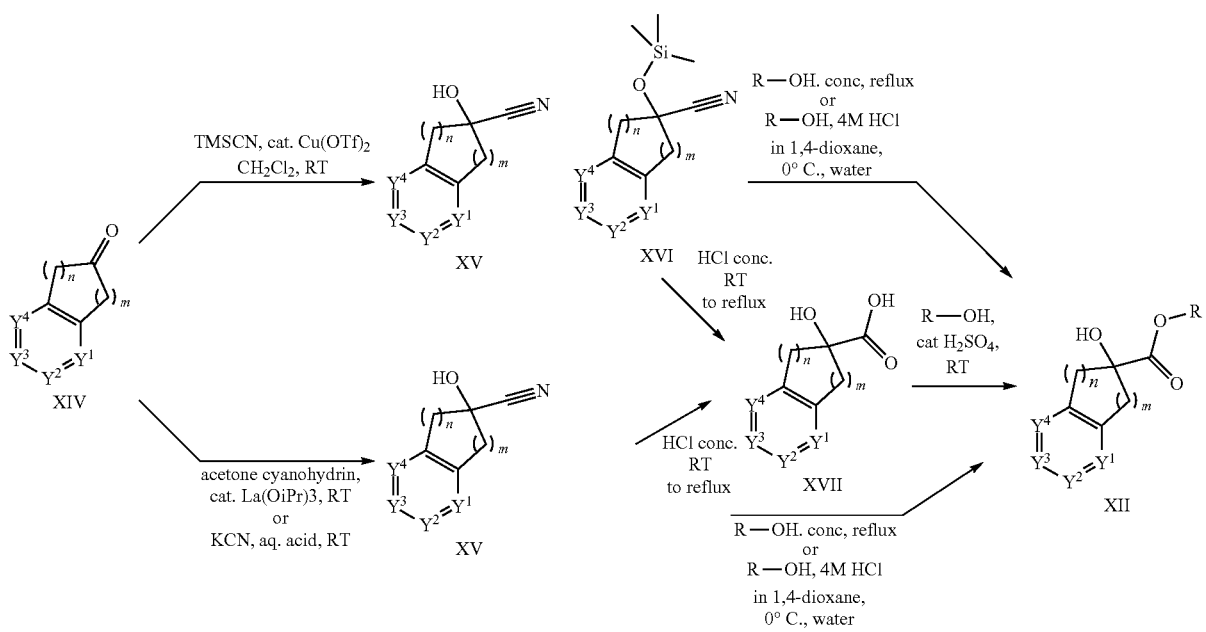

R = Me, Et

Alpha-hydroxy ester intermediates of formula (XII) can be prepared by treatment of cyanohydrin intermediates of formula (XV), (XVI) or a mixture of both, which are prepared according to methods and starting materials well known in the art, under standard conditions like stirring in a mixture of a solvent like methanol or ethanol and concentrated hydrochloric acid. Alternatively, intermediates of formula (XII) can be obtained by treatment of a compound of formula (XV), (XVI) or a mixture of both under Pinner type conditions followed by treatment of the imidate intermediate with water. Cyanohydrins of formula (XV) or (XVI) can be prepared by methods and starting materials well known in the art, e.g. by treating a ketone of formula (XIV) with trimethylsilyl cyanide in dichloromethane at room temperature using a catalyst such as copper triflate. Alternatively intermediates of formula (XV) can be prepared by treatment of a ketone of formula (XIV) with acetone cyanohydrin in a solvent such as tetrahydrofuran at room temperature using a catalyst such as lanthanum(III)triisopropoxide or with hydrogen cyanide, which can be prepared in situ from a cyanide salt such as potassium or sodium cyanide and an acid such as hydrochloric acid. Alpha-hydroxy acid intermediates of formula (XVII) can be prepared by treating a cyanohydrin of formula (XV), (XVI) or a mixture of both in an acid such as concentrated hydrochloric acid. Alpha-hydroxy ester intermediates of formula (XII) can be prepared by treatment of an alpha-hydroxy acid intermediate of formula (XVII) by esterification in an alcohol such as methanol or ethanol and a catalytic amount of an acid such as concentrated sulfuric acid. General scheme 5 is hereinafter further illustrated by general procedures XV to XVIII.

Scheme 6: General Scheme F

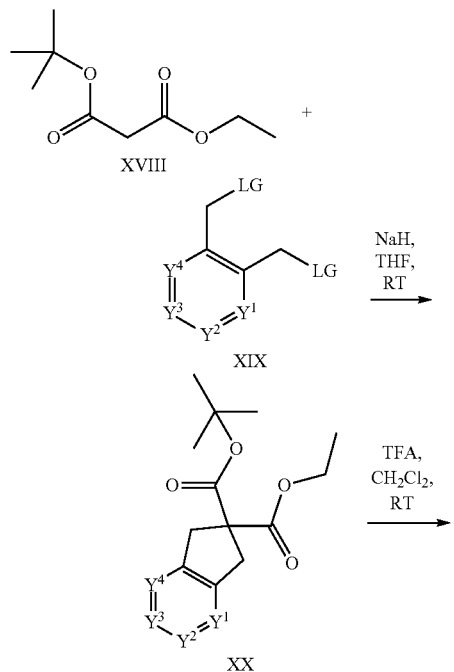

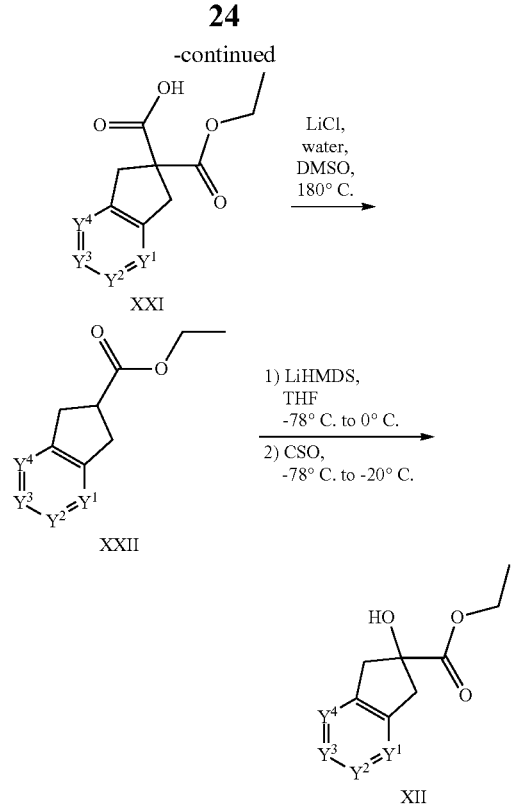

LG = Br, Cl, Ms, Ts

Malonic acid di-ester intermediates of formula (XX) can be prepared by alkylation of a commercially available malonic ester with an intermediate of formula (XIX) (wherein LG is a leaving group like halogen or sulfonyl), which is commercially available or prepared by methods known in the art. A malonic acid mono-ester intermediate of formula (XXI) can be prepared by deprotection of an intermediate of formula (XX) by methods known in the art, such as treatment with trifluroacetic acid in dichloromethane at room temperature. Indan-2-carboxylic acid intermediates of formula (XXII) are prepared by decarboxylation of intermediates of formula (XXI) in a solvent like dimethylsulfoxide in the presence of water and lithium chloride at 180° C. Alpha-hydroxy ester intermediates of formula (XII) can be obtained by treatment of an intermediate of formula (XXII) with a base like lithium diisopropylamide or lithium bis(trimethylsilyl)amide in a solvent such as tetrahydrofuran followed by alpha-hydroxylation with camphorsulfonyl oxaziridine. General scheme 6 is hereinafter further illustrated by general procedures XIII, XIV and XIX.

Scheme 7: General Scheme G

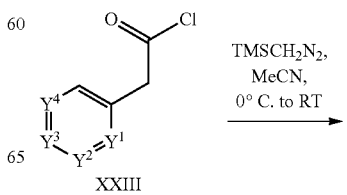

-continued

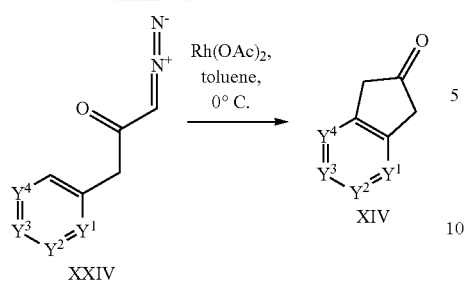

XXIV → XIV

Indan-2-one intermediates of formula (XIV) can be obtained by Rhodium catalyzed intramolecular cyclization of a diazo ketone intermediate of formula (XXIV), which can be prepared by treatment of an acid chloride of formula (XXIII) with trimethylsilyl diazomethane in acetonitrile at 0° C. General scheme 7 is hereinafter further illustrated by general procedure X.

Scheme 8: General Scheme H

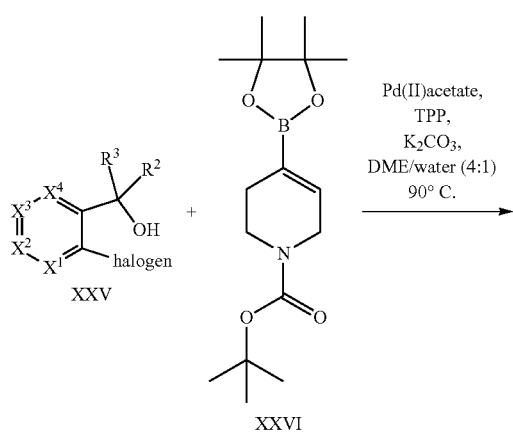

XXV + XXVI → (Pd(II)acetate, TPP, K₂CO₃, DME/water (4:1), 90° C.)

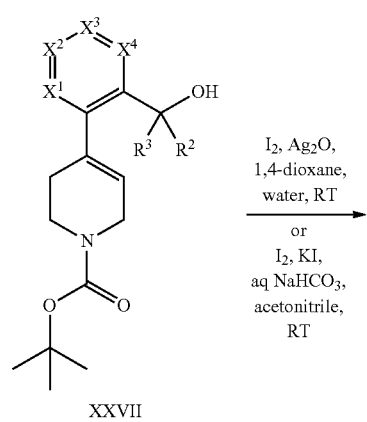

XXVII

-continued

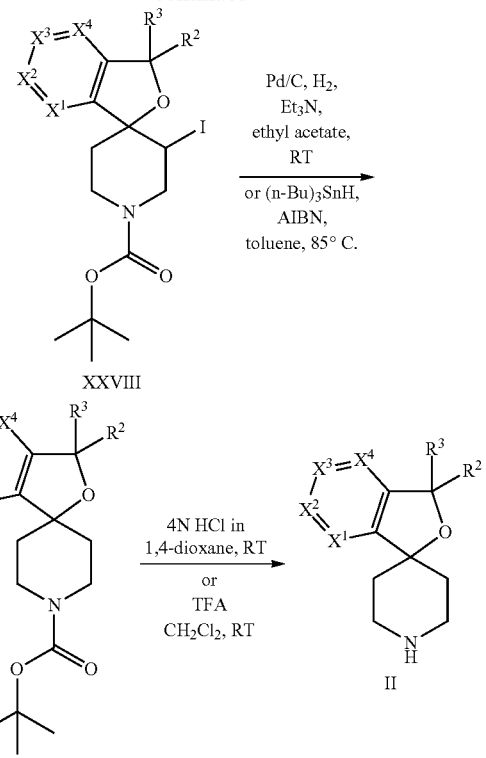

XXVIII → XXIX → II

Halogen = Cl, Br, I

Amine intermediates of formula (II) can be prepared as described hereinafter: Cross coupling reaction of an aromatic halide of formula (XXV), which is commercially available or prepared by methods known in the art, with a boronic acid ester of formula (XXVI) in the presence of a palladium catalyst, e.g. formed in situ from palladium acetate and triphenylphosphine, and an inorganic base such as potassium carbonate gives a tetrahydropyridine derivative of formula (XXVII). Compounds of formula (XXVII) can be cyclized with iodine and silver(I)oxide in a 1,4-dioxane/water mixture or with iodine and potassium iodide in a water/acetonitrile mixture to give spiro iodo-piperidines of formula (XXVIII). Compounds of formula (XXIX) can be obtained under hydrogenolytic conditions, e.g. using hydrogen gas in the presence of palladium on charcoal and an organic base such as triethyl amine, or using tri-n-butyltin hydride and a radical starter such as azobisisobutyronitrile. N-BOC-deprotection of compounds of formula (XXIX) under acidic conditions, e.g. hydrogen chloride in 1,4-dioxane or trifluoroacetic acid in dichloromethane, gives amine intermediates of formula (II). General scheme 8 is hereinafter further illustrated by general procedures I to IV and VIII to IX.

Scheme 9: General Scheme I

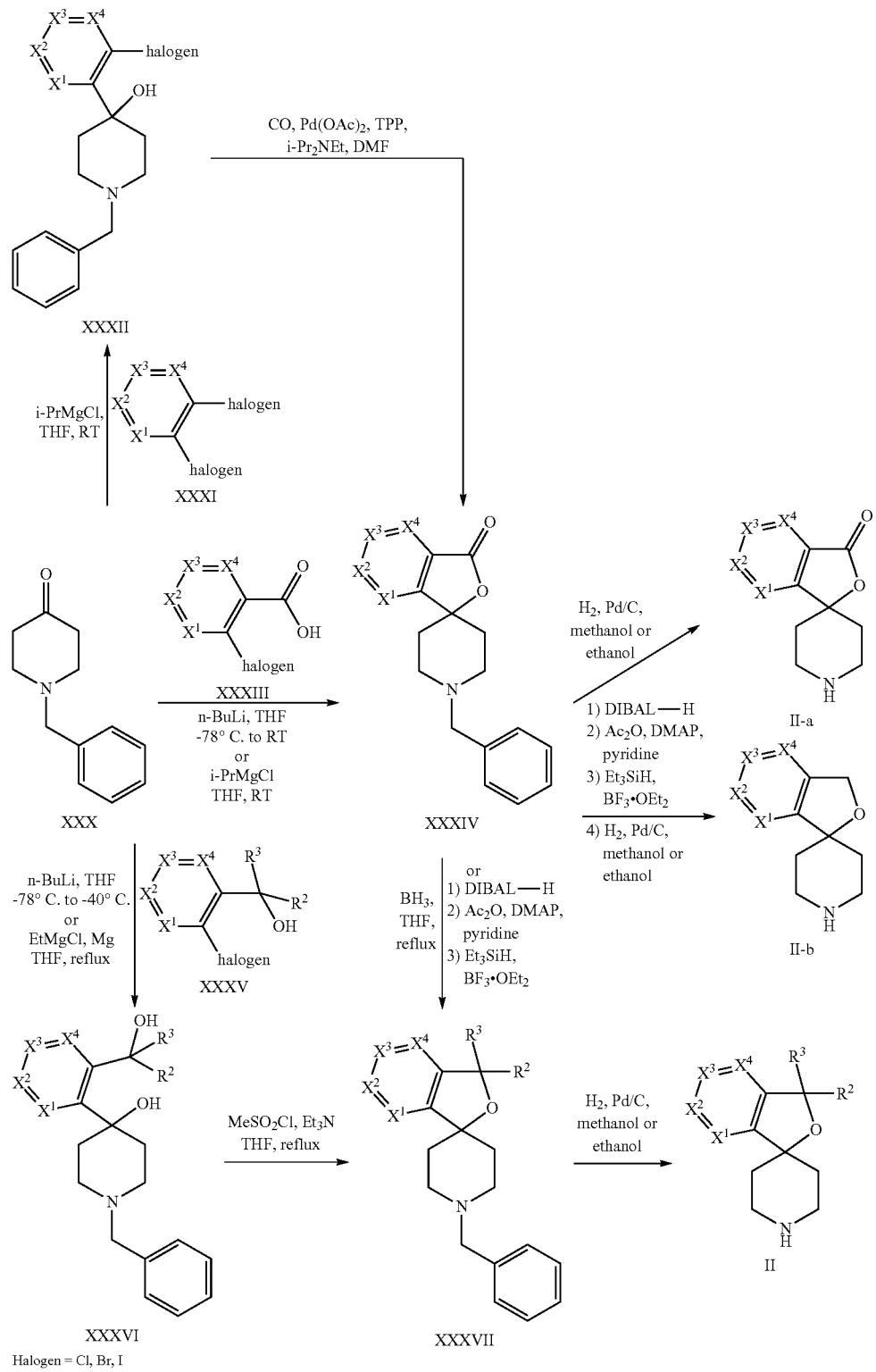

Halogen = Cl, Br, I

Amine intermediates of formulas (II), (II-a) and (II-b) can be prepared as described hereinafter: Double-lithiation of a 2-bromobenzoic acid derivative of formula (XXXIII) via deprotonation and bromine-lithium exchange with an alkyl-lithium reagent and subsequent addition to 1-benzylpiperidin-4-one (XXX) leads to a spirolactone derivative of formula (XXXIV). Compounds of formula (XXXIV) can be reduced either directly with borane or using a stepwise procedure by consecutive treatment with diisopropylaluminum hydride, acetic anhydride in the presence of pyridine and 4-(N,N-dimethylamino)-pyridine, and triethylsilane in the presence of boron trifluoride to yield compounds of formula (XXXVII). Double-metallation of a 2-bromoaryl substituted benzylic alcohol derivative of formula (XXXV), which is commercially available or prepared by methods known in the art, via O-deprotonation and bromine-metal exchange with magnesium, or a Grignard or alkyllithium reagent, and subsequent addition to 1-benzylpiperidin-4-one (XXX) leads to a diol derivative of formula (XXXVI). Cyclization of the diol derivatives of formula (XXXVI) with methanesulfonyl chloride using a base such as triethylamine leads to spiro derivatives of formula (XXXVII). Treatment of compounds of formula (XXXI), which are commercially available or prepared by methods known in the art, with isopropyl magnesium chloride leads to the formation of a Grignard reagent which is added to the carbonyl moiety of 1-benzylpiperidin-4-one (XXX) to form compounds of formula (XXXII). Treatment of a compound of formula (XXXII) with carbon monoxide in the presence of a palladium catalyst e.g. formed in situ from palladium acetate and triphenylphosphine, and an amine base to form spirolactone compounds of formula (XXXIV). Amine derivatives of formulas (II), (II-a) and (II-b) are obtained by palladium-catalyzed hydrogenolytic N-debenzylation of compounds of formulas (XXXIV) and (XXXVII), respectively. General scheme 9 is hereinafter further illustrated by general procedures VI to VII.

Scheme 10: General Scheme J

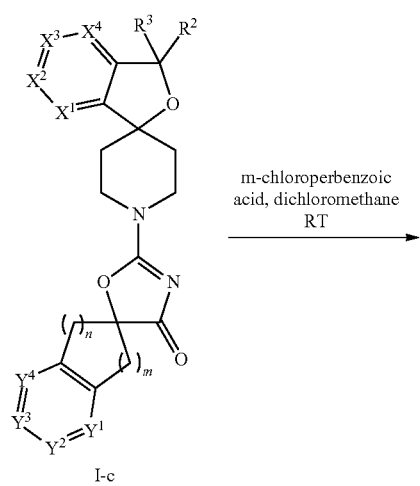

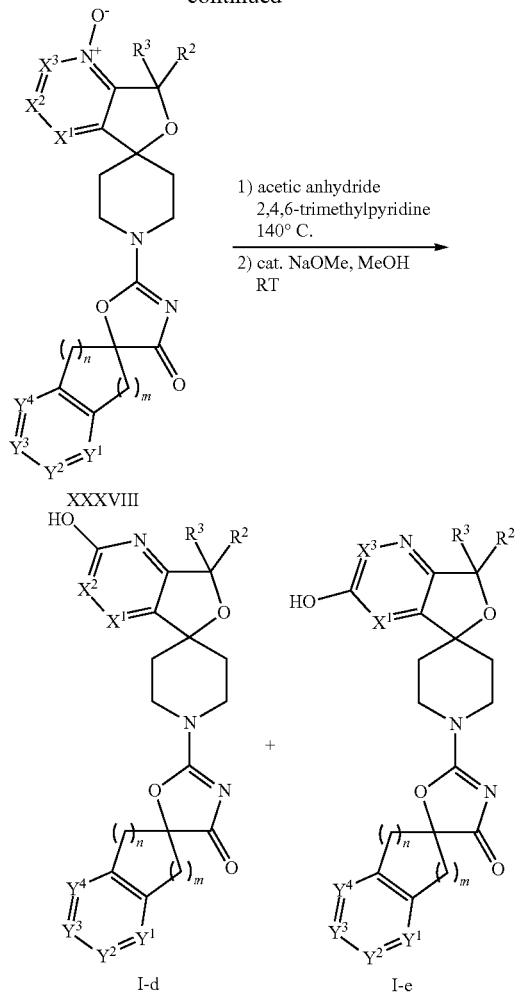

Compounds of formula (I-d) and (I-e) can be prepared as described hereinafter: An N-oxide intermediate of formula (XXXVIII) can be obtained by treatment of a compound of formula (I-c) with a suitable oxidizing agent such as m-chloroperbenzoic acid in a suitable solvent such as dichloromethane at room temperature. An N-oxide intermediate of formula (XXXVIII) can consequently be heated in excess acetic anhydride in the presence of 2,4,6-trimethylpyridine followed by treatment with a catalytic amount of sodium methoxide in methanol at room temperature to give a mixture of a compound of formula (I-d) and a compound of formula (I-e), which can be separated by a suitable method such as chromatography or crystallization. Alternatively, the O-acetylated precursors of compounds of formula (I-d) and (I-e) can be can be separated by a suitable method such as chromatography or crystallization prior to treatment with sodium methoxide in methanol.

The corresponding pharmaceutically acceptable salts with acids can be obtained by standard methods known to the person skilled in the art, e.g. by dissolving the compound of formula I in a suitable solvent such as e.g. dioxane or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. M(OH)$_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells are re-suspended in 30 ml freshly prepared ice cold Lysis buffer (50 mM HEPES, 1 mM EDTA, 10 mM MgCl$_2$ adjusted to pH=7.4+complete cocktail of protease inhibitor (Roche Diagnostics)). Homogenized with Polytron for 1 min and sonicated on ice for 2×2 minutes at 80% intensity (Vibracell sonicator). The preparation is centrifuged 20 min at 500 g at 4° C., the pellet is discarded and the supernatant centrifuged 1 hour at 43,000 g at 4° C. (19,000 rpm). The pellet is re-suspended in 12.5 ml Lysis buffer+12.5 ml Sucrose 20% and homogenized using a Polytron for 1-2 min. The protein concentration is determined by the Bradford method and aliquots are stored at −80° C. until use. For binding studies 60 mg Yttrium silicate SPA beads (Amersham) are mixed with an aliquot of membrane in binding buffer (50 mM Tris, 120 mM NaCl, 5 mM KCl, 2 mM CaCl$_2$, 10 mM MgCl$_2$) for 15 minutes with mixing. 50 µl of bead/membrane mixture is then added to each well of a 96 well plate, followed by 50 µl of 4 nM 3H-Vasopressin (American Radiolabeled Chemicals). For total binding measurement 100 µl of binding buffer are added to the respective wells, for non-specific binding 100 µl of 8.4 mM cold vasopressin and for compound testing 100 µl of a serial dilution of each compound in 2% DMSO. The plate is incubated 1 h at room temperature, centrifuged 1 min at 1000 g and counted on a Packard Top-Count. Non-specific binding counts are subtracted from each well and data is normalized to the maximum specific binding set at 100%. To calculate an IC 50 the curve is fitted using a non-linear regression model (XLfit) and the Ki is calculated using the Cheng-Prussoff equation.

The following representative data show the antagonistic activity against human V$_{1a}$ receptor of compounds according to present invention:

TABLE 1

| | pKi values of selected examples | | |
|---|---|---|---|
| Ex. | Structure | Name | pK$_i$ hV$_{1a}$ |
| 1 | 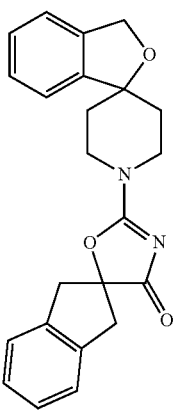 [SMILES: O=C1N=C(N2CCC3(CC2)OCc2ccccc23)OC12Cc1ccccc1C2] | 2'-(1'H,3H-spiro[2-benzofuran-1,4'-piperidin]-1'-yl)-1,3-dihydro-4'H-spiro[indene-2,5'-[1,3]oxazol]-4'-one | 9.5 |

TABLE 1-continued

| | pKi values of selected examples | | |
|---|---|---|---|
| Ex. | Structure | Name | pK$_i$ hV$_{1a}$ |
| 2 | | 1'-(4'-oxo-1,3-dihydro-4'H-spiro[indene-2,5'-[1,3]oxazol]-2'-yl)-3H-spiro[2-benzofuran-1,4'-piperidin]-3-one | 9.0 |
| 3 | | 2'-(3,3-dimethyl-1'H,3H-spiro[2-benzofuran-1,4'-piperidin]-1'-yl)-1,3-dihydro-4'H-spiro[indene-2,5'-[1,3]oxazol]-4'-one | 9.3 |
| 4 | | 2'-(4-methyl-1'H,3H-spiro[2-benzofuran-1,4'-piperidin]-1'-yl)-1,3-dihydro-4'H-spiro[indene-2,5'-[1,3]oxazol]-4'-one | 8.2 |

TABLE 1-continued pKi values of selected examples

| Ex. | Structure | Name | pK$_i$ hV$_{1a}$ |
|---|---|---|---|
| 5 | 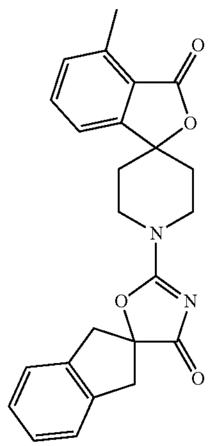 [SMILES: Cc1cccc2c1C(=O)OC21CCN(C2=NC(=O)C3(Cc4ccccc4C3)O2)CC1] | 4-methyl-1'-(4'-oxo-1,3-dihydro-4'H-spiro[indene-2,5'-[1,3]oxazol]-2'-yl)-3H-spiro[2-benzofuran-1,4'-piperidin]-3-one | 8.0 |
| 6 | 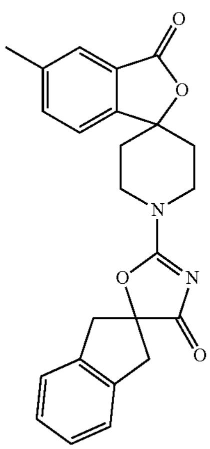 [SMILES: Cc1ccc2c(c1)C(=O)OC21CCN(C2=NC(=O)C3(Cc4ccccc4C3)O2)CC1] | 5-methyl-1'-(4'-oxo-1,3-dihydro-4'H-spiro[indene-2,5'-[1,3]oxazol]-2'-yl)-3H-spiro[2-benzofuran-1,4'-piperidin]-3-one | 8.8 |
| 7 | 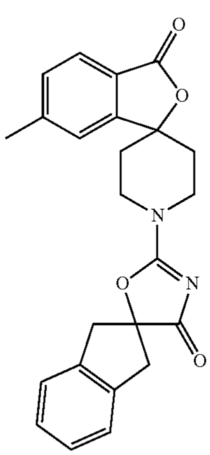 [SMILES: Cc1ccc2c(c1)C1(CCN(C3=NC(=O)C4(Cc5ccccc5C4)O3)CC1)OC2=O] | 6-methyl-1'-(4'-oxo-1,3-dihydro-4'H-spiro[indene-2,5'-[1,3]oxazol]-2'-yl)-3H-spiro[2-benzofuran-1,4'-piperidin]-3-one | 8.8 |

TABLE 1-continued pKi values of selected examples

| Ex. | Structure | Name | pK$_i$ hV$_{1a}$ |
|---|---|---|---|
| 8 | 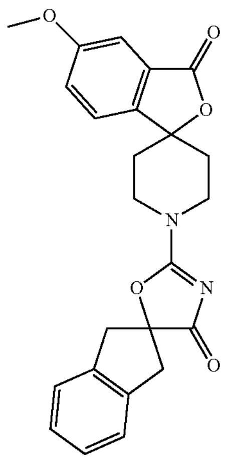 [SMILES: COc1ccc2c(c1)C(=O)OC21CCN(C2=NC(=O)C3(Cc4ccccc4C3)O2)CC1] | 5-methoxy-1'-(4'-oxo-1,3-dihydro-4'H-spiro[indene-2,5'-[1,3]oxazol]-2'-yl)-3H-spiro[2-benzofuran-1,4'-piperidin]-3-one | 8.5 |
| 9 | 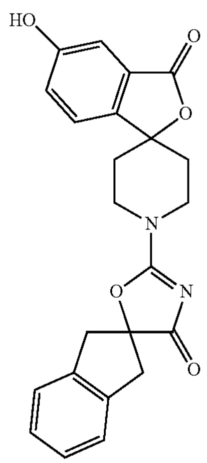 [SMILES: O=C1OC2(CCN(C3=NC(=O)C4(Cc5ccccc5C4)O3)CC2)c2ccc(O)cc21] | 5-hydroxy-1'-(4'-oxo-1,3-dihydro-4'H-spiro[indene-2,5'-[1,3]oxazol]-2'-yl)-3H-spiro[2-benzofuran-1,4'-piperidin]-3-one | 9.7 |
| 10 | 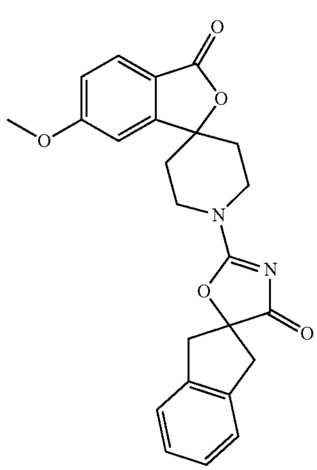 [SMILES: COc1ccc2c(c1)C1(CCN(C3=NC(=O)C4(Cc5ccccc5C4)O3)CC1)OC2=O] | 6-methoxy-1'-(4'-oxo-1,3-dihydro-4'H-spiro[indene-2,5'-[1,3]oxazol]-2'-yl)-3H-spiro[2-benzofuran-1,4'-piperidin]-3-one | 8.6 |

TABLE 1-continued

| | pKi values of selected examples | | |
|---|---|---|---|
| Ex. | Structure | Name | pK$_i$ hV$_{1a}$ |
| 11 | | 6-hydroxy-1'-(4'-oxo-1,3-dihydro-4'H-spiro[indene-2,5'-[1,3]oxazol]-2'-yl)-3H-spiro[2-benzofuran-1,4'-piperidin]-3-one | 9.1 |
| 12 | | 5,6-dimethoxy-1'-(4'-oxo-1,3-dihydro-4'H-spiro[indene-2,5'-[1,3]oxazol]-2'-yl)-3H-spiro[2-benzofuran-1,4'-piperidin]-3-one | 7.5 |
| 13 | | 5,6-dihydroxy-1'-(4'-oxo-1,3-dihydro-4'H-spiro[indene-2,5'-[1,3]oxazol]-2'-yl)-3H-spiro[2-benzofuran-1,4'-piperidin]-3-one | 8.2 |

TABLE 1-continued

| pKi values of selected examples | | | |
|---|---|---|---|
| Ex. | Structure | Name | pK$_i$ hV$_{1a}$ |
| 14 | | 4-fluoro-1'-(4'-oxo-1,3-dihydro-4'H-spiro[indene-2,5'-[1,3]oxazol]-2'-yl)-3H-spiro[2-benzofuran-1,4'-piperidin]-3-one | 8.5 |
| 15 | | 5-fluoro-1'-(4'-oxo-1,3-dihydro-4'H-spiro[indene-2,5'-[1,3]oxazol]-2'-yl)-3H-spiro[2-benzofuran-1,4'-piperidin]-3-one | 8.9 |
| 16 | | 7-fluoro-1'-(4'-oxo-1,3-dihydro-4'H-spiro[indene-2,5'-[1,3]oxazol]-2'-yl)-3H-spiro[2-benzofuran-1,4'-piperidin]-3-one | 8.7 |

TABLE 1-continued pKi values of selected examples

| Ex. | Structure | Name | pK$_i$ hV$_{1a}$ |
|---|---|---|---|
| 17 | 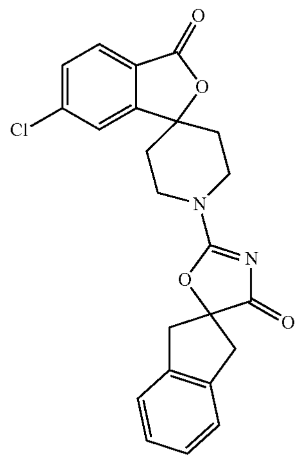 [SMILES: O=C1OC2(CCN(C3=NC(=O)C4(Cc5ccccc5C4)O3)CC2)c2cc(Cl)ccc21] | 6-chloro-1'-(4'-oxo-1,3-dihydro-4'H-spiro[indene-2,5'-[1,3]oxazol]-2'-yl)-3H-spiro[2-benzofuran-1,4'-piperidin]-3-one | 8.6 |
| 18 | 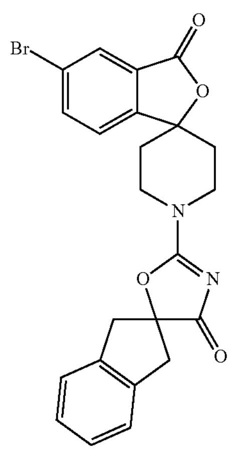 [SMILES: O=C1OC2(CCN(C3=NC(=O)C4(Cc5ccccc5C4)O3)CC2)c2ccc(Br)cc21] | 5-bromo-1'-(4'-oxo-1,3-dihydro-4'H-spiro[indene-2,5'-[1,3]oxazol]-2'-yl)-3H-spiro[2-benzofuran-1,4'-piperidin]-3-one | 8.4 |
| 19 | Chiral | (−)-2'-(1'H,3H-spiro[2-benzofuran-1,4'-piperidin]-1'-yl)-2,3-dihydro-4'H-spiro[indene-1,5'-[1,3]oxazol]-4'-one | 7.6 |

TABLE 1-continued pKi values of selected examples

| Ex. | Structure | Name | pK$_i$ hV$_{1a}$ |
|---|---|---|---|
| 20 | Chiral | (+)-2'-(1'H,3H-spiro[2-benzofuran-1,4'-piperidin]-1'-yl)-2,3-dihydro-4'H-spiro[indene-1,5'-[1,3]oxazol]-4'-one | 6.6 |
| 21 | 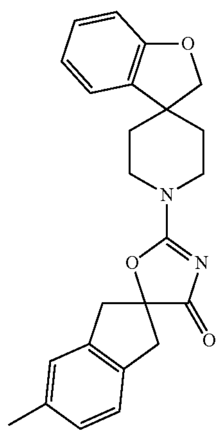 [SMILES: Cc1ccc2c(c1)CC1(C2)OC(N2CCC3(CC2)COc2ccccc23)=NC1=O] | 5-methyl-2'-(1'H,3H-spiro[2-benzofuran-1,4'-piperidin]-1'-yl)-1,3-dihydro-4'H-spiro[indene-2,5'-[1,3]oxazol]-4'-one | 9.1 |
| 22 | 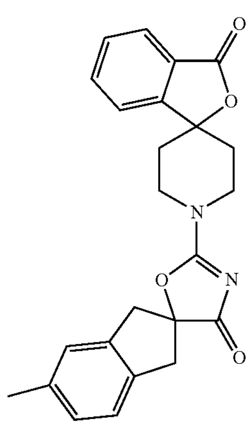 [SMILES: Cc1ccc2c(c1)CC1(C2)OC(N2CCC3(CC2)OC(=O)c2ccccc23)=NC1=O] | 1'-(5-methyl-4'-oxo-1,3-dihydro-4'H-spiro[indene-2,5'-[1,3]oxazol]-2'-yl)-3H-spiro[2-benzofuran-1,4'-piperidin]-3-one | 8.9 |

TABLE 1-continued pKi values of selected examples

| Ex. | Structure | Name | pK$_i$ hV$_{1a}$ |
|---|---|---|---|
| 23 | Chiral | (+)-1'-[5-methyl-4'-oxo-1,3-dihydro-4'H-spiro[indene-2,5'-[1,3]oxazol]-2'-yl]-3H-spiro[2-benzofuran-1,4'-piperidin]-3-one | 7.3 |
| 24 | Chiral | (−)-1'-[5-methyl-4'-oxo-1,3-dihydro-4'H-spiro[indene-2,5'-[1,3]oxazol]-2'-yl]-3H-spiro[2-benzofuran-1,4'-piperidin]-3-one | 8.6 |
| 25 | 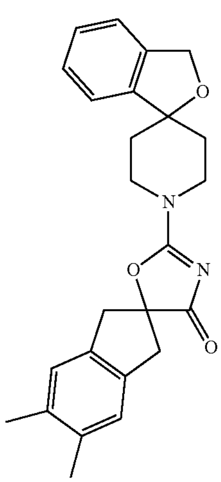 [SMILES: Cc1cc2c(cc1C)CC1(C2)OC(N2CCC3(CC2)OCc2ccccc23)=NC1=O] | 5,6-dimethyl-2'-(1'H,3H-spiro[2-benzofuran-1,4'-piperidin]-1'-yl)-1,3-dihydro-4'H-spiro[indene-2,5'-[1,3]oxazol]-4'-one | 7.1 |

TABLE 1-continued
| Ex. | Structure | Name | pK$_i$ hV$_{1a}$ |
|---|---|---|---|
| 26 | 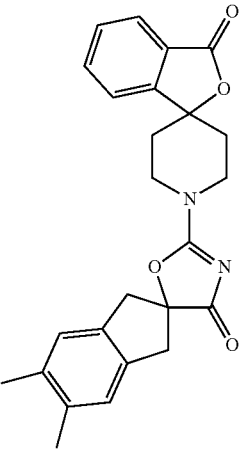 [SMILES: Cc1cc2c(cc1C)CC1(C2)OC(N2CCC3(CC2)OC(=O)c2ccccc23)=NC1=O] | 1'-(5,6-dimethyl-4'-oxo-1,3-dihydro-4'H-spiro[indene-2,5'-[1,3]oxazol]-2'-yl)-3H-spiro[2-benzofuran-1,4'-piperidin]-3-one | 6.4 |
| 27 | 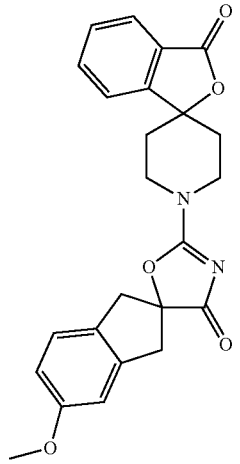 [SMILES: COc1ccc2c(c1)CC1(C2)OC(N2CCC3(CC2)OC(=O)c2ccccc23)=NC1=O] | 1'-(5-methoxy-4'-oxo-1,3-dihydro-4'H-spiro[indene-2,5'-[1,3]oxazol]-2'-yl)-3H-spiro[2-benzofuran-1,4'-piperidin]-3-one | 7.7 |
| 28 | 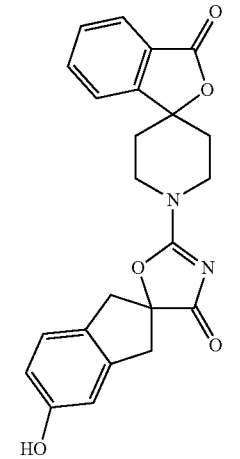 [SMILES: O=C1OC2(CCN(C3=NC(=O)C4(Cc5ccc(O)cc5C4)O3)CC2)c2ccccc21] | 1'-(5-hydroxy-4'-oxo-1,3-dihydro-4'H-spiro[indene-2,5'-[1,3]oxazol]-2'-yl)-3H-spiro[2-benzofuran-1,4'-piperidin]-3-one | 8.4 |

TABLE 1-continued pKi values of selected examples

| Ex. | Structure | Name | pK$_i$ hV$_{1a}$ |
| --- | --- | --- | --- |
| 29 | 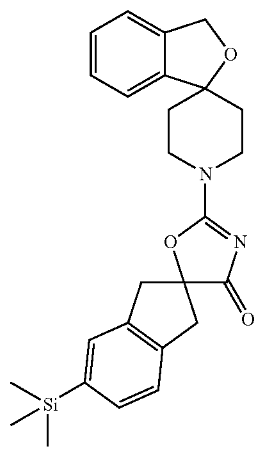 [SMILES: C[Si](C)(C)c1ccc2c(c1)CC1(C2)OC(N2CCC3(CC2)OCc2ccccc23)=NC1=O] | 2'-(1'H,3H-spiro[2-benzofuran-1,4'-piperidin]-1'-yl)-5-(trimethylsilyl)-1,3-dihydro-4'H-spiro[indene-2,5'-[1,3]oxazol]-4'-one | 6.2 |
| 30 | 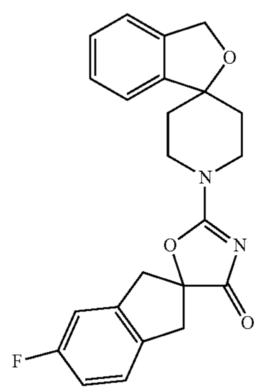 [SMILES: O=C1N=C(N2CCC3(CC2)OCc2ccccc23)OC12Cc1ccc(F)cc1C2] | 5-fluoro-2'-(1'H,3H-spiro[2-benzofuran-1,4'-piperidin]-1'-yl)-1,3-dihydro-4'H-spiro[indene-2,5'-[1,3]oxazol]-4'-one | 9.0 |
| 31 | 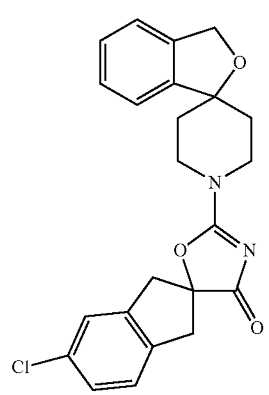 [SMILES: O=C1N=C(N2CCC3(CC2)OCc2ccccc23)OC12Cc1ccc(Cl)cc1C2] | 5-chloro-2'-(1'H,3H-spiro[2-benzofuran-1,4'-piperidin]-1'-yl)-1,3-dihydro-4'H-spiro[indene-2,5'-[1,3]oxazol]-4'-one | 9.0 |

TABLE 1-continued pKi values of selected examples

| Ex. | Structure | Name | pK$_i$ hV$_{1a}$ |
|---|---|---|---|
| 32 | 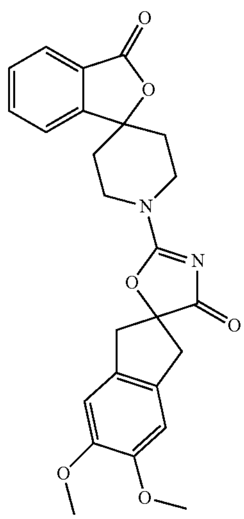 [SMILES: COc1cc2c(cc1OC)CC1(C2)OC(N2CCC3(CC2)OC(=O)c2ccccc23)=NC1=O] | 1'-(5,6-dimethoxy-4'-oxo-1,3-dihydro-4'H-spiro[indene-2,5'-[1,3]oxazol]-2'-yl)-3H-spiro[2-benzofuran-1,4'-piperidin]-3-one | 6.4 |
| 33 | 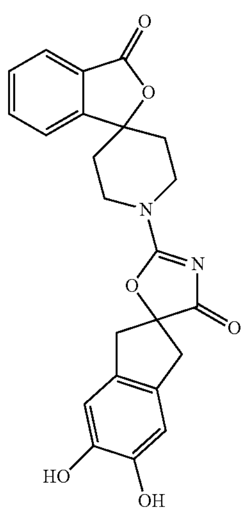 [SMILES: O=C1OC2(CCN(C3=NC(=O)C4(Cc5cc(O)c(O)cc5C4)O3)CC2)c2ccccc21] | 1'-(5,6-dihydroxy-4'-oxo-1,3-dihydro-4'H-spiro[indene-2,5'-[1,3]oxazol]-2'-yl)-3H-spiro[2-benzofuran-1,4'-piperidin]-3-one | 6.7 |
| 34 | 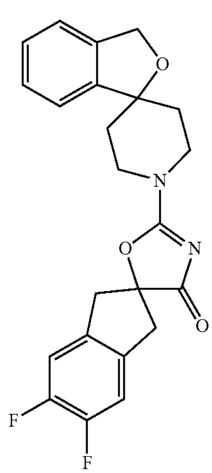 [SMILES: O=C1N=C(N2CCC3(CC2)OCc2ccccc23)OC12Cc1cc(F)c(F)cc1C2] | 5,6-difluoro-2'-(1'H,3H-spiro[2-benzofuran-1,4'-piperidin]-1'-yl)-1,3-dihydro-4'H-spiro[indene-2,5'-[1,3]oxazol]-4'-one | 9.4 |

TABLE 1-continued pKi values of selected examples

| Ex. | Structure | Name | pK$_i$ hV$_{1a}$ |
|---|---|---|---|
| 35 | 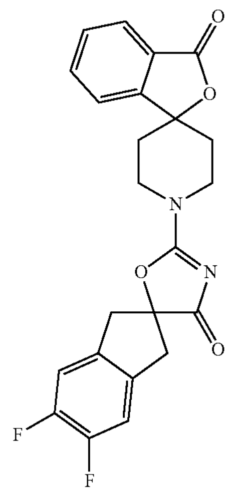 [SMILES: O=C1OC2(CCN(C3=NC(=O)C4(Cc5cc(F)c(F)cc5C4)O3)CC2)c2ccccc21] | 1'-(5,6-difluoro-4'-oxo-1,3-dihydro-4'H-spiro[indene-2,5'-[1,3]oxazol]-2'-yl)-3H-spiro[2-benzofuran-1,4'-piperidin]-3-one | 8.9 |
| 36 | 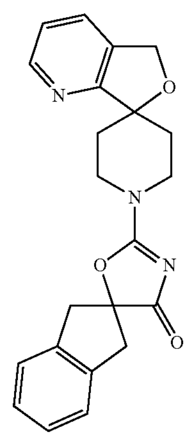 [SMILES: O=C1N=C(N2CCC3(CC2)OCc2cccnc23)OC12Cc1ccccc1C2] | 2'-(1'H,5H-spiro[furo[3,4-b]pyridine-7,4'-piperidin]-1'-yl)-1,3-dihydro-4'H-spiro[indene-2,5'-[1,3]oxazol]-4'-one | 8.6 |
| 37 | 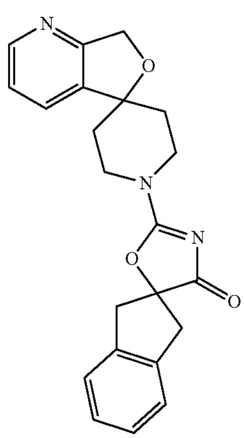 [SMILES: O=C1N=C(N2CCC3(CC2)OCc2ncccc23)OC12Cc1ccccc1C2] | 2'-(1'H,7H-spiro[furo[3,4-b]pyridine-5,4'-piperidin]-1'-yl)-1,3-dihydro-4'H-spiro[indene-2,5'-[1,3]oxazol]-4'-one | 8.0 |

TABLE 1-continued pKi values of selected examples

| Ex. | Structure | Name | pK$_i$ hV$_{1a}$ |
|---|---|---|---|
| 38 | 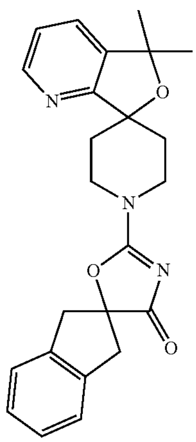 [SMILES: CC1(C)OC2(CCN(C3=NC(=O)C4(Cc5ccccc5C4)O3)CC2)c2ncccc21] | 2'-(5,5-dimethyl-1'H,5H-spiro[furo[3,4-b]pyridine-7,4'-piperidin]-1'-yl)-1,3-dihydro-4'H-spiro[indene-2,5'-[1,3]oxazol]-4'-one | 9.2 |
| 39 | 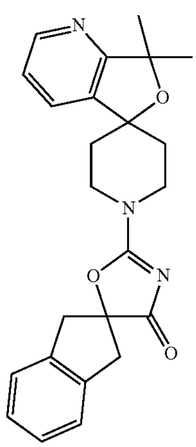 [SMILES: CC1(C)OC2(CCN(C3=NC(=O)C4(Cc5ccccc5C4)O3)CC2)c2cccnc21] | 2'-(7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one | 9.1 |
| 40 | 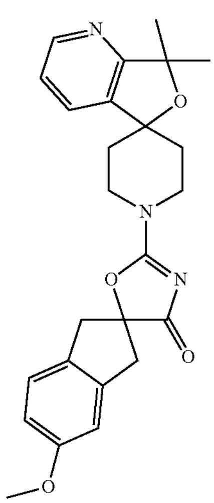 | 2'-(7,7-dimethyl-1'H,7H-spiro[furo[3,4-b]pyridine-5,4'-piperidin]-1'-yl)-5-methoxy-1,3-dihydro-4'H-spiro[indene-2,5'-[1,3]oxazol]-4'-one | 8.3 |

TABLE 1-continued pKi values of selected examples

| Ex. | Structure | Name | pK$_i$ hV$_{1a}$ |
|---|---|---|---|
| 41 | 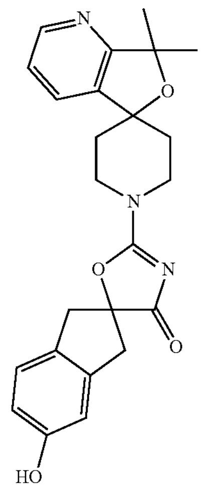 [SMILES: CC1(C)OC2(CCN(C3=NC(=O)C4(Cc5ccc(O)cc5C4)O3)CC2)c2cccnc21] | 2'-(7,7-dimethyl-1'H,7H-spiro[furo[3,4-b]pyridin-5,4'-piperidin]-1'-yl)-5-hydroxy-1,3-dihydro-4'H-spiro[indene-2,5'-[1,3]oxazol]-4'-one | 8.9 |
| 42 | 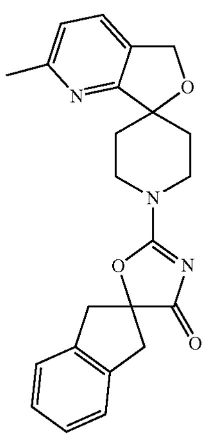 [SMILES: Cc1ccc2c(n1)C1(CCN(C3=NC(=O)C4(Cc5ccccc5C4)O3)CC1)OC2] | 2'-(2-methyl-1'H,5H-spiro[furo[3,4-b]pyridine-7,4'-piperidin]-1'-yl)-1,3-dihydro-4'H-spiro[indene-2,5'-[1,3]oxazol]-4'-one | 9.1 |
| 43 | 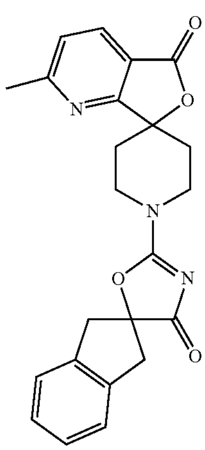 [SMILES: Cc1ccc2c(n1)C1(CCN(C3=NC(=O)C4(Cc5ccccc5C4)O3)CC1)OC2=O] | 2-methyl-1'-(4'-oxo-1,3-dihydro-4'H-spiro[indene-2,5'-[1,3]oxazol]-2'-yl)-5H-spiro[furo[3,4-b]pyridine-7,4'-piperidin]-5-one | 8.3 |

TABLE 1-continued

| | pKi values of selected examples | | |
|---|---|---|---|
| Ex. | Structure | Name | pK$_i$ hV$_{1a}$ |
| 44 | | 2'-(3-methyl-1'H,5H-spiro[furo[3,4-b]pyridine-7,4'-piperidin]-1'-yl)-1,3-dihydro-4'H-spiro[indene-2,5'-[1,3]oxazol]-4'-one | 8.7 |
| 45 | | 3-methyl-1'-(4'-oxo-1,3-dihydro-4'H-spiro[indene-2,5'-[1,3]oxazol]-2'-yl)-5H-spiro[furo[3,4-b]pyridine-7,4'-piperidin]-5-one | 7.6 |
| 46 | | 2'-(6-methyl-1H,1'H-spiro[furo[3,4-c]pyridine-3,4'-piperidin]-1'-yl)-1,3-dihydro-4'H-spiro[indene-2,5'-[1,3]oxazol]-4'-one | 8.5 |

TABLE 1-continued pKi values of selected examples

| Ex. | Structure | Name | pK$_i$ hV$_{1a}$ |
|---|---|---|---|
| 47 | 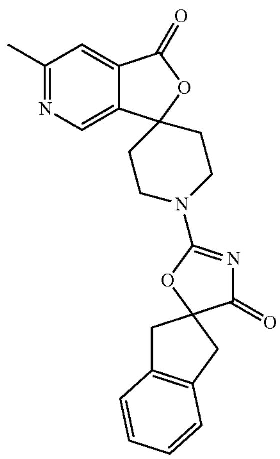 [SMILES: Cc1cc2c(cn1)C1(CCN(C3=NC(=O)C4(Cc5ccccc5C4)O3)CC1)OC2=O] | 6-methyl-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one | 7.8 |
| 48 | 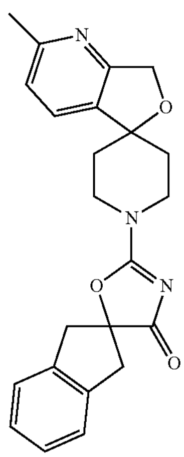 [SMILES: Cc1ccc2c(n1)COC21CCN(C2=NC(=O)C3(Cc4ccccc4C3)O2)CC1] | 2'-(2-methyl-1'H,7H-spiro[furo[3,4-b]pyridine-5,4'-piperidin]-1'-yl)-1,3-dihydro-4'H-spiro[indene-2,5'-[1,3]oxazol]-4'-one | 7.9 |
| 49 | 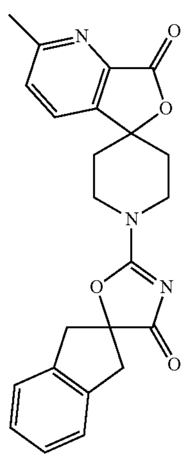 [SMILES: Cc1ccc2c(n1)C(=O)OC21CCN(C2=NC(=O)C3(Cc4ccccc4C3)O2)CC1] | 2-methyl-1'-(4'-oxo-1,3-dihydro-4'H-spiro[indene-2,5'-[1,3]oxazol]-2'-yl)-7H-spiro[furo[3,4-b]pyridine-5,4'-piperidin]-7-one | 7.0 |

TABLE 1-continued pKi values of selected examples

| Ex. | Structure | Name | pK$_i$ hV$_{1a}$ |
|---|---|---|---|
| 50 | 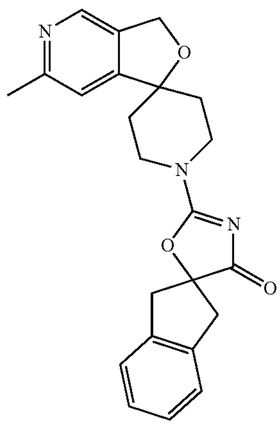 [SMILES: Cc1cc2c(cn1)COC21CCN(C2=NC(=O)C3(Cc4ccccc4C3)O2)CC1] | 2'-(6-methyl-1'H,3H-spiro[furo[3,4-c]pyridine-1,4'-piperidin]-1'-yl)-1,3-dihydro-4'H-spiro[indene-2,5'-[1,3]oxazol]-4'-one | 8.0 |
| 51 | 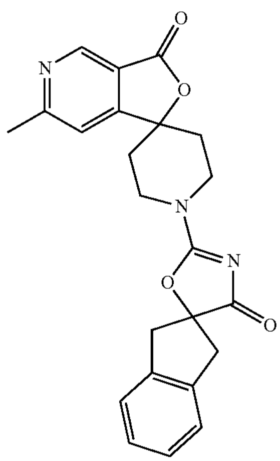 [SMILES: Cc1cc2c(cn1)C(=O)OC21CCN(C2=NC(=O)C3(Cc4ccccc4C3)O2)CC1] | 6-methyl-1'-(4'-oxo-1,3-dihydro-4'H-spiro[indene-2,5'-[1,3]oxazol]-2'-yl)-3H-spiro[furo[3,4-c]pyridine-1,4'-piperidin]-3-one | 7.9 |
| 52 | 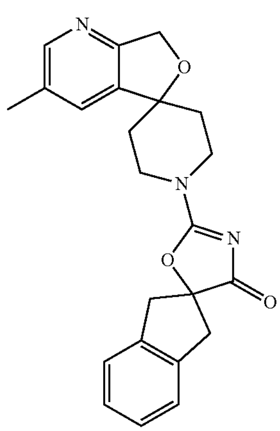 [SMILES: Cc1cnc2c(c1)C1(CCN(C3=NC(=O)C4(Cc5ccccc5C4)O3)CC1)OC2] | 2'-(3-methyl-1'H,7H-spiro[furo[3,4-b]pyridine-5,4'-piperidin]-1'-yl)-1,3-dihydro-4'H-spiro[indene-2,5'-[1,3]oxazol]-4'-one | 8.3 |

TABLE 1-continued pKi values of selected examples

| Ex. | Structure | Name | pK$_i$ hV$_{1a}$ |
|---|---|---|---|
| 53 | 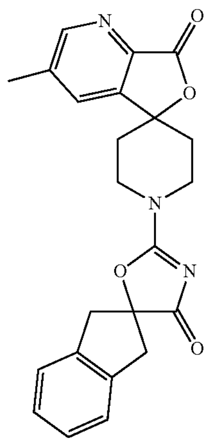 [SMILES: Cc1cnc2c(c1)C1(CCN(C3=NC(=O)C4(Cc5ccccc5C4)O3)CC1)OC2=O] | 3-methyl-1'-(4'-oxo-1,3-dihydro-4'H-spiro[indene-2,5'-[1,3]oxazol]-2'-yl)-7H-spiro[furo[3,4-b]pyridine-5,4'-piperidin]-7-one | 7.4 |
| 54 | 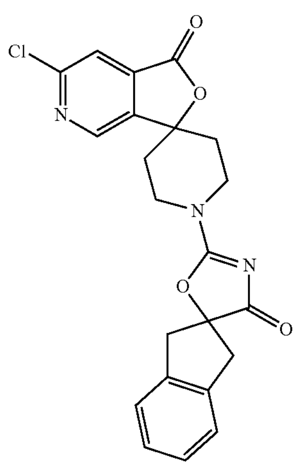 [SMILES: O=C1OC2(CCN(C3=NC(=O)C4(Cc5ccccc5C4)O3)CC2)c2cnc(Cl)cc21] | 6-chloro-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one | 7.4 |
| 55 | 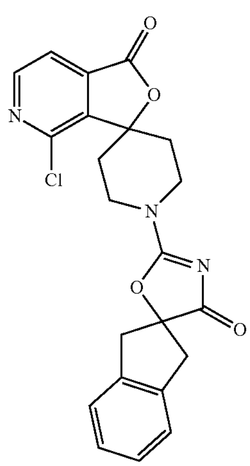 [SMILES: O=C1OC2(CCN(C3=NC(=O)C4(Cc5ccccc5C4)O3)CC2)c2c1ccnc2Cl] | 4-chloro-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one | 6.5 |

TABLE 1-continued pKi values of selected examples

| Ex. | Structure | Name | pK$_i$ hV$_{1a}$ |
|---|---|---|---|
| 56 | 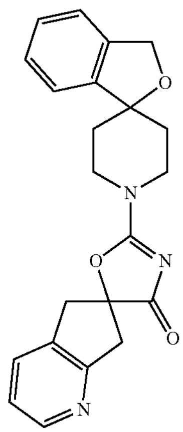 [SMILES: O=C1N=C(N2CCC3(CC2)OCc2ccccc23)OC12Cc1cccnc1C2] | 2'-(1'H,3H-spiro[2-benzofuran-1,4'-piperidin]-1'-yl)-5,7-dihydro-4'H-spiro[cyclopenta[b]pyridine-6,5'-[1,3]oxazol]-4'-one | 8.2 |
| 57 | 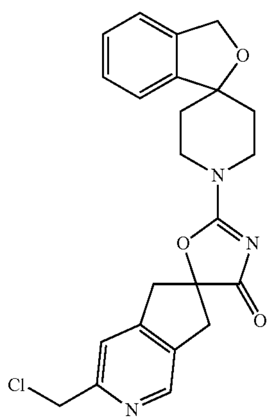 [SMILES: O=C1N=C(N2CCC3(CC2)OCc2ccccc23)OC12Cc1cnc(CCl)cc1C2] | 3-(chloromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one | 6.3 |
| 58 | 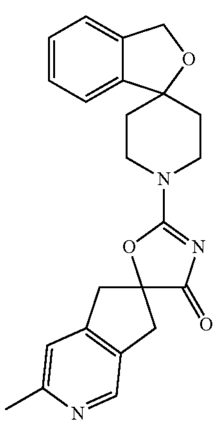 [SMILES: Cc1cc2c(cn1)CC1(C2)OC(N2CCC3(CC2)OCc2ccccc23)=NC1=O] | 3-methyl-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one | 7.7 |

TABLE 1-continued

| Ex. | Structure | Name | pK$_i$ hV$_{1a}$ |
|---|---|---|---|
| 59 | 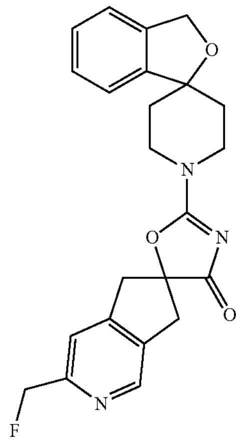 [SMILES: O=C1N=C(N2CCC3(CC2)OCc2ccccc23)OC12Cc1cnc(CF)cc1C2] | 3-(fluoromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one | 7.6 |
| 60 | 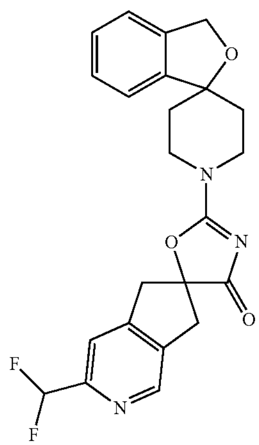 [SMILES: O=C1N=C(N2CCC3(CC2)OCc2ccccc23)OC12Cc1cnc(C(F)F)cc1C2] | 3-(difluoromethyl)-2'-(1'H,3H-spiro[2-benzofuran-1,4'-piperidin]-1'-yl)-5,7-dihydro-4'H-spiro[cylcopenta[c]pyridine-6,5'-[1,3]oxazol]-4'-one | 7.7 |
| 61 | 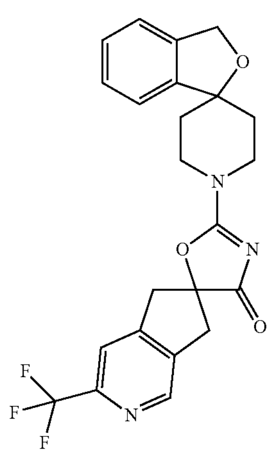 [SMILES: O=C1N=C(N2CCC3(CC2)OCc2ccccc23)OC12Cc1cnc(C(F)(F)F)cc1C2] | 2'-(1'H,3H-spiro[2-benzofuran-1,4'-piperidin]-1'-yl)-3-(trifluoromethyl)-5,7-dihydro-4'H-spiro[cyclopenta[c]pyridine-6,5'-[1,3]oxazol]-4'-one | 8.5 |

TABLE 1-continued pKi values of selected examples

| Ex. | Structure | Name | pK$_i$ hV$_{1a}$ |
|---|---|---|---|
| 62 | 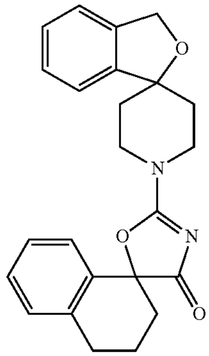 [SMILES: O=C1N=C(N2CCC3(CC2)OCc2ccccc23)OC12CCCc1ccccc12] | 2'-(1'H,3H-spiro[2-benzofuran-1,4'-piperidin]-1'-yl)-3,4-dihydro-2H,4'H-spiro[naphthalene-1,5'-[1,3]oxazol]-4'-one | 7.3 |
| 63 | 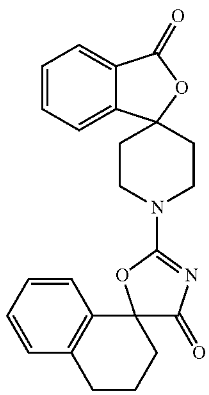 [SMILES: O=C1OC2(CCN(C3=NC(=O)C4(CCCc5ccccc54)O3)CC2)c2ccccc21] | 1'-(4'-oxo-3,4-dihydro-2H,4'H-spiro[naphthalene-1,5'-[1,3]oxazol]-2'-yl)-3H-spiro[2-benzofuran-1,4'-piperidin]-3-one | 6.7 |
| 64 | 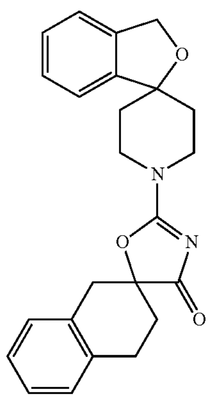 [SMILES: O=C1N=C(N2CCC3(CC2)OCc2ccccc23)OC12CCc1ccccc1C2] | 2'-(1'H,3H-spiro[2-benzofuran-1,4'-piperidin]-1'-yl)-3,4-dihydro-1H,4'H-spiro[naphthalene-2,5'-[1,3]oxazol]-4'-one | 9.0 |
| 65 | 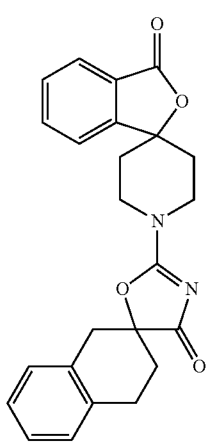 [SMILES: O=C1OC2(CCN(C3=NC(=O)C4(CCc5ccccc5C4)O3)CC2)c2ccccc21] | 1'-(4'-oxo-3,4-dihydro-1H,4'H-spiro[naphthalene-2,5'-[1,3]oxazol]-2'-yl)-1'H,3H-spiro[2-benzofuran-1,4'-piperidin]-3-one | 8.8 |

TABLE 1-continued pKi values of selected examples

| Ex. | Structure | Name | pK$_i$ hV$_{1a}$ |
|---|---|---|---|
| 66 | Chiral | 1'-[4'-oxo-3,4-dihydro-1H,4'H-spiro[naphthalene-2,5'-[1,3]oxazol]-2'-yl]-1'H,3H-spiro[2-benzofuran-1,4'-piperidin]-3-one enantiomer A | 9.1 |
| 67 | Chiral | 1'-[4'-oxo-3,4-dihydro-1H,4'H-spiro[naphthalene-2,5'-[1,3]oxazol]-2'-yl]-1'H,3H-spiro[2-benzofuran-1,4'-piperidin]-3-one enantiomer B | 8.4 |
| 68 | 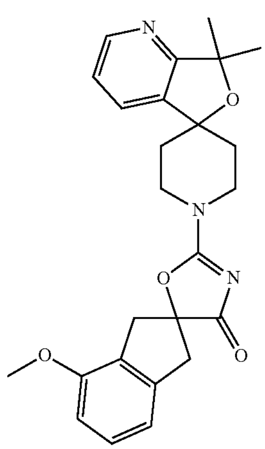 | 2'-(7,7-dimethyl-1'H,7H-spiro[furo[3,4-b]pyridine-5,4'-piperidin]-1'-yl)-4-methyl-1,3-dihydro-4'H-spiro[indene-2,5'-[1,3]oxazol]-4'-one | 8.1 |

TABLE 1-continued

| | pKi values of selected examples | | |
|---|---|---|---|
| Ex. | Structure | Name | pK$_i$ hV$_{1a}$ |
| 69 | | 2'-(7,7-dimethyl-1'H,7H-spiro[furo[3,4-b]pyridine-5,4'-piperidin]-1'-yl)-4-hydroxy-1,3-dihydro-4'H-spiro[indene-2,5'-[1,3]oxazol]-4'-one | 9.3 |
| 70 | | 2'-(7,7-dimethyl-1-oxido-1'H,7H-spiro[furo[3,4-b]pyridine-5,4'-piperidin]-1'-yl)-1,3-dihydro-4'H-spiro[indene-2,5'-[1,3]oxazol]-4'-one | 7.3 |
| 71 | | 2'-(3-hydroxy-7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'one | 10.2 |

TABLE 1-continued pKi values of selected examples

| Ex. | Structure | Name | pK$_i$ hV$_{1a}$ |
|---|---|---|---|
| 72 | 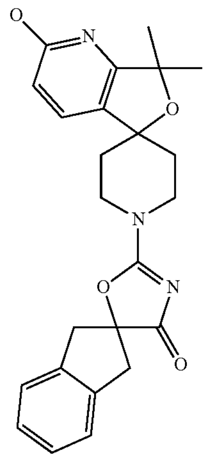 [SMILES: CC1(C)OC2(CCN(C3=NC(=O)C4(Cc5ccccc5C4)O3)CC2)c2ccc(O)nc21] | 2'-(2-hydroxy-7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'one | 8.5 |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, in particular 1-100 mg, of a compound of formula I. Examples of compositions according to the invention are:

EXAMPLE A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

EXAMPLE B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 6 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

EXAMPLE D

Injection solutions of the following composition are manufactured:

TABLE 7 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 8 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

The following table lists abbreviations used within the present document.

TABLE 9 list with abbreviations

| | |
|---|---|
| AIBN | azobisisobutyronitrile |
| brine | saturated sodium chloride solution in water |
| CH$_2$Cl$_2$ | dichloromethane |
| Cp | cyclopentadienyl, C$_5$H$_5^-$ |
| cod | cyclooctadiene |
| CSO | (10-camphorsulfonyl)oxaziridine |
| Cu(OTf)$_2$ | copper(II) trifluoromethanesulfonate |
| DBU | 1,8-diazabicyclo[5.4.0]undec-7-ene |
| DIBAL-H | diisobutylaluminium hydride |
| DMAP | 4-(N,N-dimethylamino)-pyridine |
| DME | 1,2-dimethoxyethane |
| DMSO | dimethylsulfoxide |
| Et$_3$N | triethylamine |
| LDA | lithium diisopropylamide |
| LiHMDS | lithium bis(trimethylsilyl)amide |
| MeOH | methanol |
| MS 4A | molecular sieves 4Angstrom |
| NaOH | sodium hydroxide |
| n-BuOH | n-butanol |
| RT | room temperature |
| t-BuOK, KOtBu | potassium tert-butanolate |
| TFA | trifluoroacetic acid |
| THF | tetrahydrofuran |
| TMSCN | trimethylsilyl cyanide |
| TPP | triphenylphosphine |

EXPERIMENTAL PART

The following examples are provided for illustration of the invention. They should not be considered as limiting the scope of the invention, but merely as being representative thereof.

Pyridine Intermediates of Formula (XXV)

Pyridine Intermediate 1

(2-Chloro-5-methylpyridin-3-yl)methanol

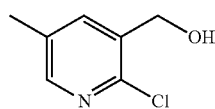

To a solution of 2-chloro-5-methylnicotinic acid (1.5 g, 8.6 mmol) and triethylamine (0.92 g, 1.3 ml, 9.1 mmol) in tetrahydrofuran (24 ml) was added ethyl chloroformate (0.98 g, 0.87 ml, 9.1 mmol) at 0-5° C. The ice bath was removed after 5 minutes and stirring was continued for 1 h. The solids were removed by filtration and washed with tetrahydrofuran. The filtrate was concentrated in vacuo to give the crude mixed anhydride. To a solution of lithium aluminum hydride (0.34 g, 9.1 mmol) in tetrahydrofuran (18 ml) was added the mixed anhydride from above as a solution in tetrahydrofuran (9 ml) at −78° C. in approximately 20 minutes. Stirring was continued for 2 h. The reaction mixture was quenched by addition of water (0.34 ml), 2 M aqueous sodium hydroxide solution (0.34 ml) and again water (1.02 ml) at −70° C. The dry ice/acetone bath was removed and stirring was continued for 1 h. The precipitate was removed by filtration and washed with tetrahydrofuran. The filtrate was concentrated in vacuo to give the title compound (1.1 g, 82%) as white solid, which was used in the next step without further purifications. MS m/e: 158 [(M+H)$^+$].

Pyridine Intermediate 2

2-(3-Bromopyridin-2-yl)propan-2-ol

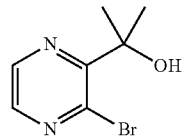

To a solution of methyl 3-bromopicolinate (5.0 g, 23 mmol) in tetrahydrofuran (116 ml) was added dropwise in approximately 15 minutes methylmagnesium chloride, 3 M in tetrahydrofuran (16 ml, 49 mmol) at 0-5° C. The ice bath was removed after 30 minutes and stirring was continued for 1 h. The reaction mixture was quenched with 2 M aqueous hydrogen chloride solution (23 ml, 46 mmol) and stirred for 5 minutes. The solvent was evaporated. The residue was partitioned between tert-butyl methyl ether (100 ml) and saturated ammonium chloride solution (100 ml). The layers were separated. The aqueous layer was extracted with two 100-ml portions of tert-butyl methyl ether. The combined organic layers were washed with one 50-ml portion of brine, dried over anhydrous sodium sulfate, filtered and concentrated in vacuo. Flash chromatography with n-heptane/ethyl acetate as eluent gave the title compound (4.2 g, 76%) as light yellow oil with a purity of 90% according to NMR. MS m/e: 216, 218 [(M+H)$^+$].

Pyridine Intermediate 3

2-(2-Bromopyridin-3-yl)propan-2-ol

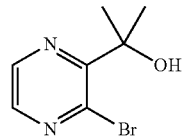

To a solution of 2,3-dibromopyridine (5.5 g, 23 mmol) in tetrahydrofuran (77 ml) was added isopropylmagnesium chloride, 2 M in tetrahydrofuran (15 ml, 30 mmol) at room temperature. The reaction mixture was stirred for 45 minutes. Acetone (2.7 g, 3.4 ml, 46 mmol) was added in a quick fashion at room temperature. The reaction mixture was stirred for 16 h and the quenched with 2 M aqueous hydrogen chloride solution (15 ml). The solvent was evaporated. The residue was partitioned between ethyl acetate (100 ml) and water (100 ml). The layers were separated. The aqueous layer was extracted with one 100-ml portion of ethyl acetate. The combined organic layers were washed with one 50-ml portion of saturated ammonium chloride solution, dried over anhydrous sodium sulfate, filtered and concentrated in vacuo. Flash chromatography with n-heptane/ethyl acetate gave the title compound (2.4 g, 48%) as light brown viscous oil. MS m/e: 216, 218 [(M+H)+].

tert-Butyl 4-aryl-5,6-dihydropyridine-1(2H)-carboxylate Intermediates of Formula (XXVII)

General Procedure I: Suzuki Coupling

To a solution of a heteroaromatic compound of formula (XXV), tert-butyl 4-(4,4,5,5-tetramethyl-1,3,2-dioxaborolan-2-yl)-5,6-dihydropyridine-1(2H)-carboxylate (1.1-1.5 eq) and potassium carbonate (3 eq) in 1,2-dimethoxyethane/water (0.2 M, 4:1) is added palladium(II)acetate (0.05 eq) and triphenylphosphine (0.1 eq). The reaction mixture is heated at 90° C. and stirred for 6-24 h. The reaction mixture is partitioned between an organic solvent such as ethyl acetate or tert-butyl methyl ether and water. The layers are separated. The aqueous layer is extracted with one or two portions of organic solvent. The combined organic layers are dried over anhydrous sodium sulfate, filtered and concentrated to dryness. Purification by flash-chromatography gives a tert-butyl 4-aryl-5,6-dihydropyridine-1(2H)-carboxylate of formula (XXVII).

tert-Butyl 4-aryl-5,6-dihydropyridine-1(2H)-carboxylate 1 tert-Butyl 4-(3-(hydroxymethyl)-5-methylpyridin-2-yl)-5,6-dihydropyridine-1(2H)-carboxylate

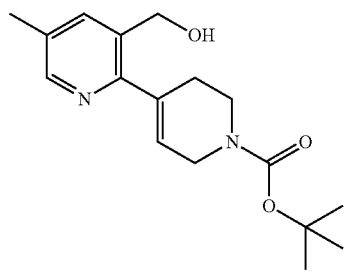 [SMILES: Cc1cnc(C2=CCN(C(=O)OC(C)(C)C)CC2)c(CO)c1]

The title compound was obtained as light yellow viscous oil in 89% yield according to the general procedure XXVII from (2-chloro-5-methylpyridin-3-yl)methanol and tert-butyl 4-(4,4,5,5-tetramethyl-1,3,2-dioxaborolan-2-yl)-5,6-dihydropyridine-1(2H)-carboxylate. MS m/e: 305 [(M+H)+].

tert-Butyl 4-aryl-5,6-dihydropyridine-1(2H)-carboxylate 2 tert-Butyl 4-(2-(2-hydroxypropan-2-yl)pyridin-3-yl)-5,6-dihydropyridine-1(2H)-carboxylate

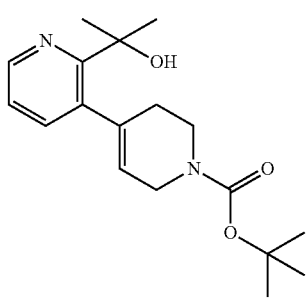 [SMILES: CC(C)(C)OC(=O)N1CC=C(c2cccnc2C(C)(C)O)CC1]

The title compound was obtained as colorless viscous oil in 35% yield according to the general procedure I from 2-(3-bromopyridin-2-yl)propan-2-ol and tert-butyl 4-(4,4,5,5-tetramethyl-1,3,2-dioxaborolan-2-yl)-5,6-dihydropyridine-1(2H)-carboxylate. MS m/e: 319 [(M+H)+].

tert-Butyl 4-aryl-5,6-dihydropyridine-1(2H)-carboxylate 3

Methyl 2-(1-(tert-butoxycarbonyl)-1,2,3,6-tetrahydropyridin-4-yl)-5-methyl nicotinate

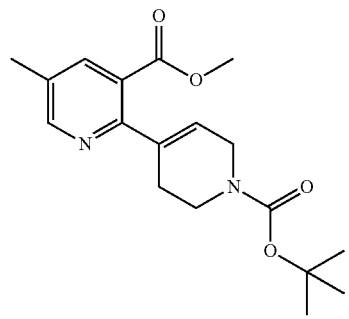 [SMILES: COC(=O)c1cc(C)cnc1C1=CCN(C(=O)OC(C)(C)C)CC1]

The title compound was obtained as light brown oil in 78% yield according to the general procedure I from methyl 2-chloro-5-methylnicotinate and tert-butyl 4-(4,4,5,5-tetramethyl-1,3,2-dioxaborolan-2-yl)-5,6-dihydropyridine-1(2H)-carboxylate. MS m/e: 333 [(M+H)+].

tert-Butyl 4-aryl-5,6-dihydropyridine-1(2H)-carboxylate 4

Methyl 3-(1-(tert-butoxycarbonyl)-1,2,3,6-tetrahydropyridin-4-yl)-5-methyl picolinate

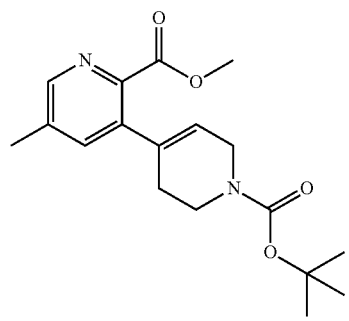 [SMILES: COC(=O)c1ncc(C)cc1C1=CCN(C(=O)OC(C)(C)C)CC1]

The title compound was obtained as yellow solid in 74% yield according to the general procedure I from methyl 3-bromo-5-methylpicolinate and tert-butyl 4-(4,4,5,5-tetramethyl-1,3,2-dioxaborolan-2-yl)-5,6-dihydropyridine-1(2H)-carboxylate. MS m/e: 333 [(M+H)+].

tert-Butyl 4-aryl-5,6-dihydropyridine-1(2H)-carboxylate 5

2-(1-(tert-Butoxycarbonyl)-1,2,3,6-tetrahydropyridin-4-yl)-5-methylnicotinic acid

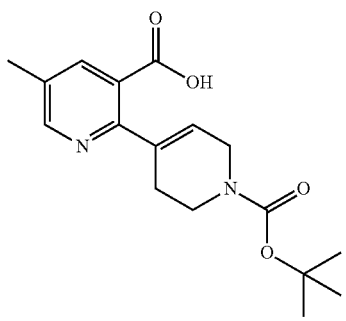 [SMILES: Cc1cnc(C2=CCN(C(=O)OC(C)(C)C)CC2)c(C(=O)O)c1]

A mixture of methyl 2-(1-(tert-butoxycarbonyl)-1,2,3,6-tetrahydropyridin-4-yl)-5-methylnicotinate (2.5 g, 7.5 mmol) in 1,4-dioxane (38 ml) and 2 M aqueous sodium hydroxide solution (38 ml, 75 mmol) was stirred for 3 h at room temperature. The reaction mixture was partitioned between ethyl acetate (125 ml) and water (10 ml). The layers were separated. The aqueous layer was acidified by addition of 2 M aqueous hydrochloric acid (38 ml, 75 mmol) and extracted with five 125-ml portions of ethyl acetate. The combined ethyl acetate layers from the acidic extraction were dried over anhydrous sodium sulfate, filtered and concentrated in vacuo. The residue was triturated in n-heptane (50 ml) and ethyl acetate (5 ml). The precipitate was collected by filtration, washed with n-heptane and dried in vacuo to give the title compound (1.5 g, 64%) as light yellow solid. MS m/e: 319 [(M+H)$^+$].

tert-Butyl 4-aryl-5,6-dihydropyridine-1(2H)-carboxylate 6

3-(1-(tert-Butoxycarbonyl)-1,2,3,6-tetrahydropyridin-4-yl)-5-methylpicolinic acid

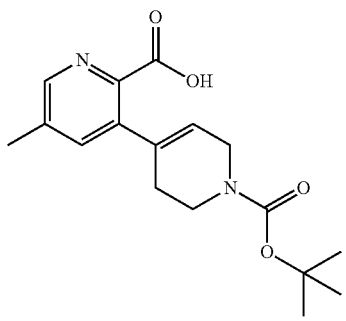 [SMILES: Cc1cnc(C(=O)O)c(C2=CCN(C(=O)OC(C)(C)C)CC2)c1]

A solution of methyl 3-(1-(tert-butoxycarbonyl)-1,2,3,6-tetrahydropyridin-4-yl)-5-methylpicolinate (1.0 g, 3.1 mmol) in 1,4-dioxane (15 ml) and 2 M aqueous sodium hydroxide solution (15 ml, 31 mmol) was stirred for 2 h at room temperature. The reaction mixture was partitioned between isopropyl acetate (50 ml) and water (30 ml). The layers were separated. The aqueous layer was acidified by addition of 2 M aqueous hydrochloric acid (15 ml, 31 mmol) and extracted with five 75-ml portions of ethyl acetate. The combined ethyl acetate layers from the acidic extraction were dried over anhydrous sodium sulfate, filtered and concentrated in vacuo. The residue was triturated in n-heptane (20 ml) and ethyl acetate (2 ml). The precipitate was collected by filtration, washed with n-heptane and dried in vacuo to give the title compound (1.0 g, quantitative) as white solid. MS m/e: 319 [(M+H)$^+$].

tert-Butyl 4-aryl-5,6-dihydropyridine-1(2H)-carboxylate 7

2-(1-(tert-Butoxycarbonyl)-1,2,3,6-tetrahydropyridin-4-yl)-6-methylnicotinic acid

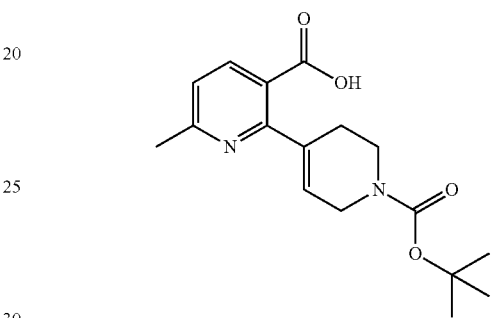

The title compound was obtained as white foam in 30% yield according to the general procedure I from 2-chloro-6-methylnicotinic acid and tert-butyl 4-(4,4,5,5-tetramethyl-1,3,2-dioxaborolan-2-yl)-5,6-dihydropyridine-1(2H)-carboxylate. MS m/e: 319 [(M+H)$^+$].

Iodo-spiropiperidine Intermediates of Formula (XXVIII)

General Procedure II: Cyclization with Iodine and Silver (I)Oxide

To a solution a of tert-butyl 4-aryl-5,6-dihydropyridine-1(2H)-carboxylate of formula (XXVII) in 1,4-dioxane/water (0.05-0.1 M, 7:1) is added iodine (1.5 eq) at room temperature. The reaction mixture is stirred for 30 minutes. Addition of silver(I)oxide (1.5 eq) in small portions is followed by stirring for 2-16 h. The solids are removed by filtration and washed with a solvent such as tetrahydrofuran, dioxane or ethyl acetate. The filtrate is concentrated in vacuo. The residue is partitioned between an organic solvent such as ethyl acetate or tert-butyl methyl ether and an aqueous inorganic base such as 1 M aqueous sodium carbonate solution. The layers are separated. The aqueous layer is extracted with one or two portions of organic solvent. The combined organic layers are washed with one portion of brine (containing 5-10 volume-% aqueous 40% sodium bisulfite) dried over anhydrous sodium sulfate, filtered and concentrated to dryness. Purification by flash-chromatography gives an iodo-spiropiperidine of formula (XXVIII).

General Procedure III: Cyclization with Iodine and Potassium Iodide

To a solution of a tert-butyl 4-aryl-5,6-dihydropyridine-1(2H)-carboxylate of formula (XXVII) in acetonitrile (0.3 M) and 1 M aqueous sodium bicarbonate solution (0.1 M) is added iodine (1.5 eq) and subsequently a 1 M aqueous potassium iodide solution at room temperature. The reaction

Iodo-Spiropiperidine Intermediate 1 tert-Butyl 3'-iodo-7,7-dimethyl-7H-spiro[furo[3,4-b]pyridine-5,4'-piperidine]-1'-carboxylate

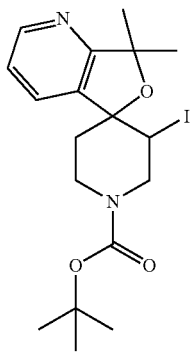 [SMILES: CC(C)(C)OC(=O)N1CCC2(OC(C)(C)c3ncccc32)C(I)C1]

The title compound was obtained as light yellow solid in 94% yield according to the general procedure II from tert-butyl 4-(2-(2-hydroxypropan-2-yl)pyridin-3-yl)-5,6-dihydropyridine-1(2H)-carboxylate. MS m/e: 445 [(M+H)$^+$].

Iodo-Spiropiperidine Intermediate 2 tert-Butyl 3'-iodo-3-methyl-5-oxo-5H-spiro[furo[3,4-b]pyridine-7,4'-piperidine]-1'-carboxylate

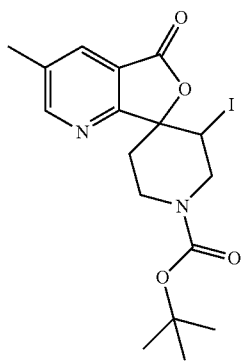 [SMILES: Cc1cnc2c(c1)C(=O)OC21CCN(C(=O)OC(C)(C)C)CC1I]

The title compound was obtained as off-white solid in 85% yield according to the general procedure III from 2-(1-(tert-butoxycarbonyl)-1,2,3,6-tetrahydropyridin-4-yl)-5-methylnicotinic acid. MS m/e: 389 [(M-C$_4$H)$^+$].

Iodo-Spiropiperidine Intermediate 3 tert-Butyl 3'-iodo-3-methyl-7-oxo-7H-spiro[furo[3,4-b]pyridine-5,4'-piperidine]-1'-carboxylate

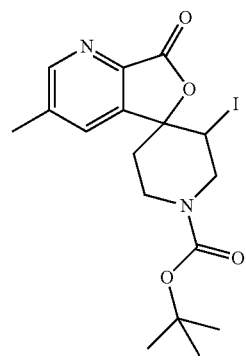 [SMILES: Cc1cnc2c(c1)C1(CCN(C(=O)OC(C)(C)C)CC1I)OC2=O]

The title compound was obtained as white solid in 75% yield according to the general procedure III from 3-(1-(tert-butoxycarbonyl)-1,2,3,6-tetrahydropyridin-4-yl)-5-methylpicolinic acid. MS m/e: 445 [(M+H)$^+$].

Iodo-Spiropiperidine Intermediate 4 tert-Butyl 3'-iodo-3-methyl-5H-spiro[furo[3,4-b]pyridine-7,4'-piperidine]-1'-carboxylate

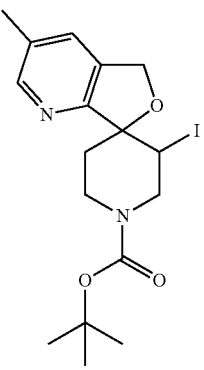 [SMILES: Cc1cnc2c(c1)COC21CCN(C(=O)OC(C)(C)C)CC1I]

The title compound was obtained as white solid in 14% yield according to the general procedure II from tert-butyl 4-(3-(hydroxymethyl)-5-methylpyridin-2-yl)-5,6-dihydropyridine-1(2H)-carboxylate. MS m/e: 431 [(M+H)$^+$].

Iodo-Spiropiperidine Intermediate 5 tert-Butyl 3'-iodo-2-methyl-5-oxo-5H-spiro[furo[3,4-b]pyridine-7,4'-piperidine]-1'-carboxylate

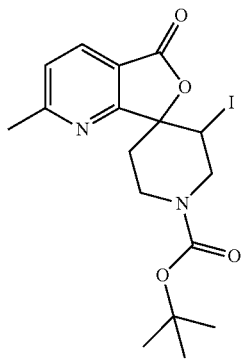 [SMILES: Cc1ccc2c(n1)C1(CCN(C(=O)OC(C)(C)C)CC1I)OC2=O]

The title compound was obtained as white solid in 77% yield according to the general procedure III from 2-(1-(tert-butoxycarbonyl)-1,2,3,6-tetrahydropyridin-4-yl)-6-methylnicotinic acid. MS m/e: 389 [(M–C$_4$H$_8$)$^+$].

Spiropiperidine Intermediates of Formula (XXIX)

General Procedure IV: Hydrogenolytic Deiodination

An iodo-spiropiperidine intermediate of formula (XXVIII) (1 eq) is dissolved in a solvent such as ethyl acetate (0.1 M). The flask is evacuated until the solvent begins to bubble gently and back-filled with Argon after 10-30 s. This procedure is repeated twice. After the addition of an organic base such as triethylamine (1.5 eq) and a catalyst such as palladium, 10% on activated charcoal (0.1-0.5 eq), the flask is evacuated until the solvent begins to bubble and back-filled with hydrogen. The reaction mixture is stirred under an atmosphere of 1 bar of hydrogen gas for 24-72 h. The catalyst is removed by filtration over Decalite and washed with a solvent such as ethyl acetate. The filtrate is concentrated in vacuo. Purification by flash-chromatography gives a spiropiperidine intermediate of formula (XXIX).

General Procedure V: Deiodination with Tributyltin Hydride

To a solution of an iodo-spiropiperidine intermediate of formula (XXVIII) (1 eq) and azobisisobutyronitrile (0.05 eq) in toluene (0.1 M) is added dropwise tri-n-butyltin hydride (3 eq) at 85° C. The reaction mixture is stirred for 24-48 h. The reaction mixture is quenched with 1 M aqueous potassium fluoride solution (5 eq) at room temperature and stirring is continued for 24 h. The layers are separated. The aqueous layer is extracted with one portion of toluene. The combined organic layers are purified by flash-chromatography to give a spiropiperidine of formula (XXIX).

Spiropiperidine Intermediate 1 tert-Butyl 3-methyl-7H-spiro[furo[3,4-b]pyridine-5,4'-piperidine]-1'-carboxylate a) tert-Butyl 4-hydroxy-4-(2-(hydroxymethyl)-5-methylpyridin-3-yl)piperidine-1-carboxylate

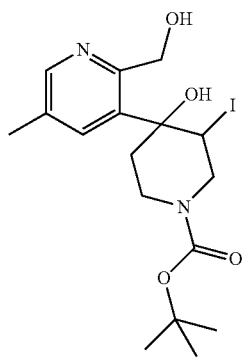 [SMILES: Cc1cnc(CO)c(C2(O)CCN(C(=O)OC(C)(C)C)CC2I)c1]

To a suspension of tert-butyl 3-methyl-7-oxo-7H-spiro[furo[3,4-b]pyridine-5,4'-piperidine]-1'-carboxylate (0.51 g, 1.61 mmol) in ethanol (8.0 ml) was added sodium borohydride (0.13 g, 3.53 mmol) in small portions at room temperature. Stirring was continued for 6 h. The reaction mixture was quenched with water (6 ml) and partitioned between ethyl acetate (50 ml) and water (30 ml). The layers were separated. The aqueous layer was extracted with two 50-ml portions of ethyl acetate. The combined organic layers were washed with one 30-ml portion of brine, dried over anhydrous sodium sulfate, filtered and concentrated in vacuo. Flash chromatography with n-heptane/ethyl acetate gave the title compound (0.38 g, 73%) as white foam. MS m/e: 323 [(M+H)$^+$].

b) tert-Butyl 3-methyl-7H-spiro[furo[3,4-b]pyridine-5,4'-piperidine]-1'-carboxylate

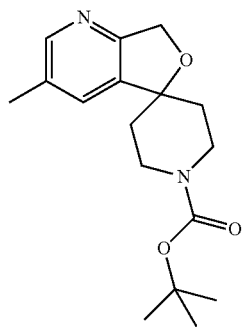 [SMILES: Cc1cnc2c(c1)C1(CCN(C(=O)OC(C)(C)C)CC1)OC2]

To a solution of tert-butyl 4-hydroxy-4-(2-(hydroxymethyl)-5-methylpyridin-3-yl)piperidine-1-carboxylate (0.38 g, 1.2 mmol), 4-(N,N-dimethylamino)-pyridine (0.007 g, 0.059 mmol) and triethylamine (0.35 ml, 2.5 mmol) in tetrahydrofuran (4.7 ml) was added methanesulfonyl chloride (0.092 ml, 1.2 mmol) at 0-5° C. The ice bath was removed after 5 minutes and stirring was continued for 5 h at room temperature. The reaction mixture was heated at 50°

C. and stirred for 3 h. The solids were removed by filtration and washed with tetrahydrofuran. Sodium hydride (0.062 g, 1.4 mmol) was added to the filtrate at 0-5° C. The ice bath was removed and stirring was continued for 16 h. The reaction mixture was quenched with water (1 ml) and partitioned between ethyl acetate (50 ml) and 1 M aqueous sodium hydroxide solution (30 ml). The layers were separated. The aqueous layer was extracted with two 50-ml portions of ethyl acetate. The combined organic layers were washed with one 30-ml portion of brine, dried over anhydrous sodium sulfate, filtered and concentrated in vacuo. Flash chromatography with n-heptane/ethyl acetate gave the title compound (0.21 g, 57%) as white solid. MS m/e: 305 [(M+H)$^+$].

Spiropiperidine Intermediate 2 tert-Butyl 3-methyl-5H-spiro[furo[3,4-b]pyridine-7, 4'-piperidine]-1'-carboxylate

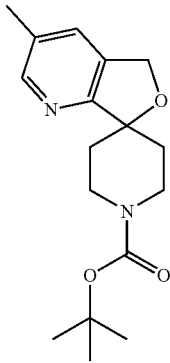 [SMILES: Cc1cnc2c(c1)COC21CCN(C(=O)OC(C)(C)C)CC1]

The title compound was obtained as colorless viscous oil in 77% yield according to the general procedure V from tert-butyl 3'-iodo-3-methyl-5H-spiro[furo[3,4-b]pyridine-7, 4'-piperidine]-1'-carboxylate. MS m/e: 305 [(M+H)$^+$].

Spiropiperidine Intermediate 3 tert-Butyl 2-methyl-7H-spiro[furo[3,4-b]pyridine-5, 4'-piperidine]-1'-carboxylate a) tert-Butyl 4-hydroxy-4-(2-(hydroxymethyl)-6-methylpyridin-3-yl)piperidine-1-carboxylate

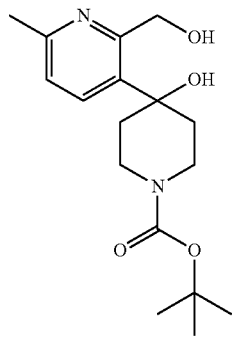 [SMILES: Cc1ccc(C2(O)CCN(C(=O)OC(C)(C)C)CC2)c(CO)n1]

To a solution of lithium aluminum hydride (0.067 g, 1.8 mmol) and in tetrahydrofuran (3.6 ml) was added 1'-benzyl-2-methyl-7H-spiro[furo[3,4-b]pyridine-5,4'-piperidin]-7-one (0.54 g, 1.8 mmol) as a solution in tetrahydrofuran (1.8 ml) at 0-5° C. The ice bath was removed after 10 minutes and stirring was continued for 15 h. The reaction mixture was quenched by addition of water (0.066 ml), 2 M aqueous sodium hydroxide solution (0.066 ml) and again water (0.2 ml) at 0-5° C. The reaction mixture was stirred for 2 h. The precipitate was removed by filtration and washed with tetrahydrofuran. The filtrate was concentrated in vacuo to give a mixture of the N-benzyl- and des-benzyl-di-ol intermediate. A solution of the mixture and di-tert-butyl dicarbonate (0.55 g, 2.5 mmol) in ethanol (17 ml) was purged with Argon. Palladium, 10% on activated charcoal (0.18 g, 0.17 mmol) was added. The flask was filled with hydrogen and stirred for 15 h. The catalyst was removed by filtration over Decalite and washed with ethanol. The filtrate was concentrated in vacuo. Flash chromatography with n-heptane/isopropanol as eluent gave a di-BOC intermediate mixture. To a solution of di-BOC intermediate mixture in 1,4-dioxane (2 ml) was added 4 M hydrogen chloride solution in 1,4-dioxane (2.1 g, 2.0 ml, 8.0 mmol) at room temperature. The mixture was stirred overnight. The solvent was evaporated. To a suspension of the crude 4-(2-(hydroxymethyl)-6-methylpyridin-3-yl)piperidin-4-ol dihydrochloride salt in dichloromethane (3.6 ml) was added triethylamine (0.45 ml, 3.2 mmol) at room temperature. Stirring for 10 minutes was followed by addition of di-tert-butyl-dicarbonate (0.24 g, 1.1 mmol) at room temperature. The reaction mixture was stirred for 15 h at room temperature. The reaction mixture was partitioned between dichloromethane (40 ml) and 1 M aqueous sodium hydroxide solution (20 ml). The layers were separated. The aqueous layer was extracted with two 40-ml portions of dichloromethane. The combined organic layers were washed with one 30-ml portion of brine, dried over anhydrous sodium sulfate, filtered and concentrated in vacuo. Flash chromatography with n-heptane/isopropanol gave the title compound as white foam (0.14 g, 40%). MS m/e: 327.5 [(M+H)$^+$].

b) tert-Butyl 2-methyl-7H-spiro[furo[3,4-b]pyridine-5,4'-piperidine]-1'-carboxylate

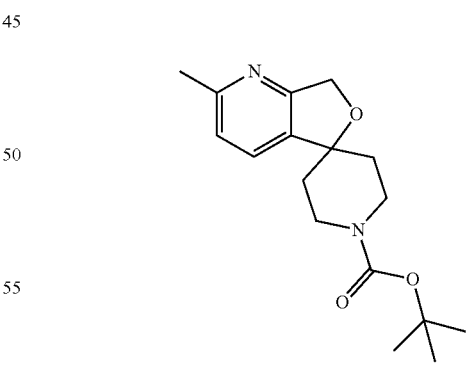

To a solution of tert-butyl 4-hydroxy-4-(2-(hydroxymethyl)-6-methylpyridin-3-yl)piperidine-1-carboxylate (0.14 g, 0.43 mmol), a catalytic amount 4-(N,N-dimethylamino)-pyridine and triethylamine (0.13 ml, 0.91 mmol) in tetrahydrofuran (2.2 ml) was added methanesulfonyl chloride (0.034 ml, 0.43 mmol) at 0-5° C. The ice bath was removed after 5 minutes and the reaction mixture was heated to 70° C. for 15 h. The reaction mixture was partitioned between ethyl acetate (50 ml) and 1 M aqueous sodium hydroxide solution (30 ml). The layers were separated. The aqueous layer was extracted with two 50-ml portions of ethyl acetate. The combined organic layers were washed with one 30-ml portion of brine, dried over anhydrous sodium sulfate, filtered and concentrated in vacuo. Flash chromatography with n-heptane/ethyl acetate gave the title compound (0.015 g, 11%) as white solid. MS m/e: 305 [(M+H)$^+$].

Spiropiperidine Intermediate 4 tert-Butyl 2-methyl-5H-spiro[furo[3,4-b]pyridine-7,4'-piperidine]-1'-carboxylate a) tert-Butyl 4-hydroxy-4-(3-(hydroxymethyl)-6-methylpyridin-2-yl)piperidine-1-carboxylate

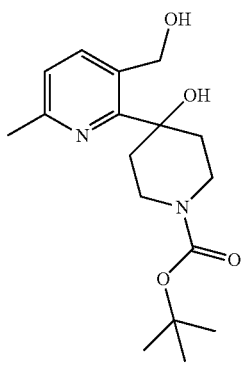 [SMILES: Cc1ccc(CO)c(C2(O)CCN(C(=O)OC(C)(C)C)CC2)n1]

To a solution of tert-butyl 2-methyl-5-oxo-5H-spiro[furo[3,4-b]pyridine-7,4'-piperidine]-1'-carboxylate (0.36 g, 1.13 mmol) in ethanol (5.7 ml) was added sodium borohydride (0.094 g, 2.49 mmol) in small portions at room temperature. The reaction mixture was stirred for 19 h. The reaction mixture was quenched with water (3 ml), stirred for 1 h and partitioned between ethyl acetate (40 ml) and water (30 ml). The layers were separated. The aqueous layer was extracted with three 30-ml portions of ethyl acetate. The combined organic layers were washed with one 30-ml portion of brine, dried over anhydrous sodium sulfate, filtered and concentrated in vacuo. Flash chromatography with n-heptane/ethyl acetate gave the title compound (0.16 g, 43%) as white foam. MS m/e: 323 [(M+H)$^+$].

b) tert-Butyl 2-methyl-5H-spiro[furo[3,4-b]pyridine-7,4'-piperidine]-1'-carboxylate

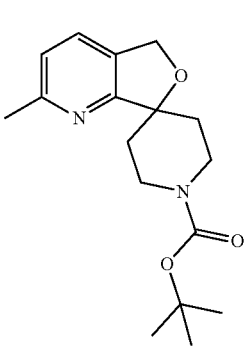 [SMILES: Cc1ccc2c(n1)C1(CCN(C(=O)OC(C)(C)C)CC1)OC2]

To a solution of tert-butyl 4-hydroxy-4-(3-(hydroxymethyl)-6-methylpyridin-2-yl)piperidine-1-carboxylate (0.15 g, 0.47 mmol), a catalytic amount of 4-(N,N-dimethylamino)-pyridine and triethylamine (0.14 ml, 0.99 mmol) in tetrahydrofuran (1.9 ml) was added methanesulfonyl chloride (0.037 ml, 0.47 mmol) at 0-5° C. The ice bath was removed after 5 minutes and stirring was continued for 2 h at room temperature. The reaction mixture was partitioned between ethyl acetate (40 ml) and 1 M aqueous sodium hydroxide solution (30 ml). The layers were separated. The aqueous layer was extracted with two 40-ml portions of ethyl acetate. The combined organic layers were washed with one 30-ml portion of brine, dried over anhydrous sodium sulfate, filtered and concentrated in vacuo. Flash chromatography with n-heptane/ethyl acetate as eluent gave the title compound (0.1 g, 75%) as white solid. MS m/e: 305 [(M+H)$^+$].

Spiropiperidine Intermediate 5 tert-Butyl 7,7-dimethyl-7H-spiro[furo[3,4-b]pyridine-5,4'-piperidine]-1'-carboxylate

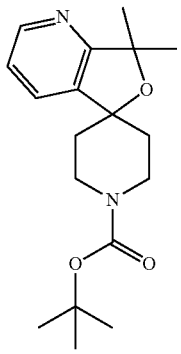 [SMILES: CC(C)(C)OC(=O)N1CCC2(CC1)OC(C)(C)c1ncccc12]

The title compound was obtained as off-white solid in 24% yield according to the general procedure IV from tert-butyl 3'-iodo-7,7-dimethyl-7H-spiro[furo[3,4-b]pyridine-5,4'-piperidine]-1'-carboxylate. MS m/e: 319 [(M+H)$^+$].

Spiropiperidine Intermediate 6 tert-Butyl 3-methyl-7-oxo-7H-spiro[furo[3,4-b]pyridine-5,4'-piperidine]-1'-carboxylate

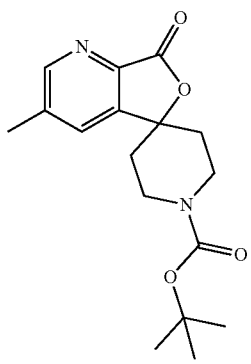 [SMILES: Cc1cnc2c(c1)C1(CCN(C(=O)OC(C)(C)C)CC1)OC2=O]

The title compound was obtained as white solid in 83% yield according to the general procedure V from tert-butyl 3'-iodo-3-methyl-7-oxo-7H-spiro[furo[3,4-b]pyridine-5,4'-piperidine]-1'-carboxylate. MS m/e: 319 [(M+H)⁺].

Spiropiperidine Intermediate 7 tert-Butyl 2-methyl-5-oxo-5H-spiro[furo[3,4-b]pyridine-7,4'-piperidine]-1'-carboxylate

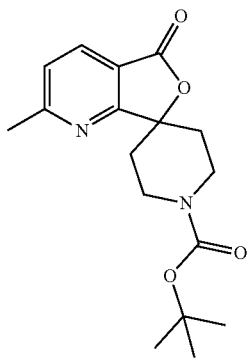 [SMILES: Cc1ccc2c(n1)C1(CCN(C(=O)OC(C)(C)C)CC1)OC2=O]

The title compound was obtained as white solid in 95% yield according to the general procedure V from tert-butyl 3'-iodo-2-methyl-5-oxo-5H-spiro[furo[3,4-b]pyridine-7,4'-piperidine]-1'-carboxylate. MS m/e: 263 [(M-C₄H)⁺].

Spiropiperidine Intermediate 8 tert-Butyl 3-methyl-5-oxo-5H-spiro[furo[3,4-b]pyridine-7,4'-piperidine]-1'-carboxylate

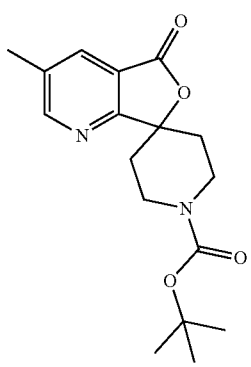 [SMILES: Cc1cnc2c(c1)C(=O)OC21CCN(C(=O)OC(C)(C)C)CC1]

The title compound was obtained as white solid in 78% yield according to the general procedure V from tert-butyl 3'-iodo-3-methyl-5-oxo-5H-spiro[furo[3,4-b]pyridine-7,4'-piperidine]-1'-carboxylate. MS m/e: 263 [(M-C₄Hs)⁺].

N-Benzyl Spiropiperidine Intermediates of Formula (XXXIV)

General Procedure VI:

To a solution of a halogen carboxylic acid of formula (XXXIII) (1 eq) in tetrahydrofuran (0.5 M) is added 1.6 M solution of n-butyllithium (2.05 eq) in n-hexane at −78° C. After 5-30 minutes 1-benzylpiperidin-4-one (1.0 eq) is added. The reaction mixture is stirred for 30-60 minutes and then quenched with 2M aqueous hydrogen chloride solution. The cooling bath is removed and stirring is continued for 1-2 h. The reaction mixture is partitioned between an organic solvent such as ethyl acetate or tert-butyl methyl ether and 0.5 M aqueous sodium hydroxide solution. The layers are separated. The aqueous layer is extracted with one or two portions of organic solvent. The combined organic layers are dried over anhydrous sodium sulfate, filtered and concentrated to dryness. The crude product mixture is dissolved in acetone (0.1-0.3 M) and 4 M hydrogen chloride solution in 1,4-dioxane (2 eq) is added dropwise at room temperature. The precipitate is collected by filtration, washed with acetone and dried in vacuo to give pure spirolactone hydrochloride salt. The salt is partitioned between an organic solvent such as ethyl acetate or tert-butyl methyl ether and 0.5-1.0 aqueous sodium hydroxide solution. The layers are separated. The aqueous layer is extracted with one or two portions of organic solvent. The combined organic layers are dried over anhydrous sodium sulfate, filtered and concentrated to dryness to give a N-benzyl spiropiperidine intermediate of formula (XXXIV).

N-Benzylpiperidine Intermediate 1

1'-Benzyl-4-methyl-3H-spiro[isobenzofuran-1,4'-piperidin]-3-one

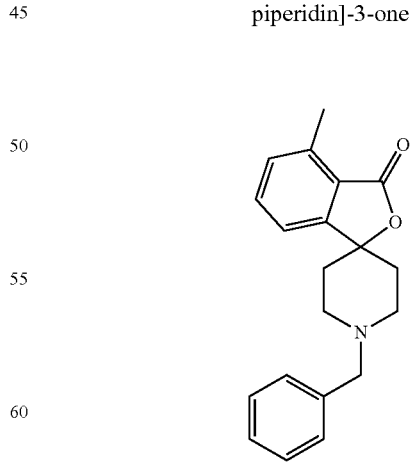

The title compound was obtained as amorphous colorless solid in 10% yield according to the general procedure VI from 2-bromo-6-methylbenzoic acid and 1-benzylpiperidin-4-one. MS m/e: 308 [(M+H)⁺].

N-Benzylpiperidine Intermediate 2

1'-Benzyl-5,6-dimethoxy-3H-spiro[isobenzofuran-1,4'-piperidin]-3-one

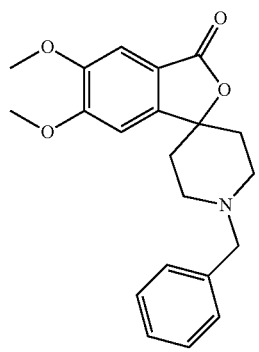 [SMILES: COc1cc2c(cc1OC)C1(CCN(Cc3ccccc3)CC1)OC2=O]

The title compound was obtained as white foam in 24% yield according to the general procedure VI from 2-bromo-4,5-dimethoxybenzoic acid and 1-benzylpiperidin-4-one. MS m/e: 354 [(M+H)$^+$].

N-Benzylpiperidine Intermediate 3

1'-Benzyl-2-methyl-7H-spiro[furo[3,4-b]pyridine-5,4'-piperidin]-7-one

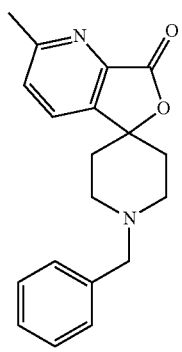 [SMILES: Cc1ccc2c(n1)C(=O)OC21CCN(Cc2ccccc2)CC1]

The title compound was obtained as off-white solid in 21% yield according to the general procedure VI from 3-bromo-6-methylpicolinic acid and 1-benzylpiperidin-4-one. MS m/e: 309 [(M+H)$^+$].

N-Benzylpiperidine Intermediate 4

1'-Benzyl-6-methyl-3H-spiro[furo[3,4-c]pyridine-1,4'-piperidin]-3-one

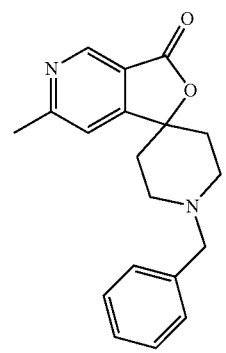 [SMILES: Cc1cc2c(cn1)C(=O)OC21CCN(Cc2ccccc2)CC1]

The title compound was obtained as white solid in 7% yield according to the general procedure VI from 4-bromo-6-methylnicotinic acid and 1-benzylpiperidin-4-one. MS m/e: 310 [(M+H)$^+$].

N-Benzylpiperidine Intermediate 5

1'-Benzyl-6-chloro-1H-spiro[furo[3,4-c]pyridine-3,4'-piperidin]-1-one

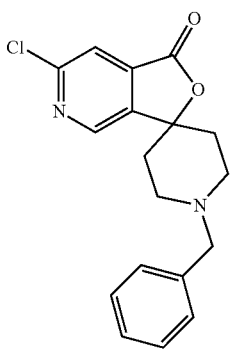 [SMILES: O=C1OC2(CCN(Cc3ccccc3)CC2)c2cnc(Cl)cc21]

The title compound was obtained as yellow oil in 11% yield according to the general procedure VI from 5-bromo-2-chloroisonicotinic acid and 1-benzylpiperidin-4-one. MS m/e: 329 [(M+H)$^+$].

N-Benzylpiperidine Intermediate 6

1'-Benzyl-6-methyl-1H-spiro[furo[3,4-c]pyridine-3,4'-piperidin]-1-one

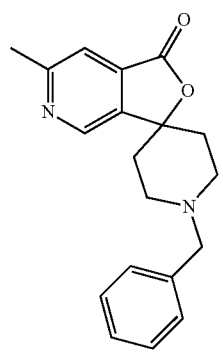 [SMILES: Cc1cc2c(cn1)C1(CCN(Cc3ccccc3)CC1)OC2=O]

To a suspension of 1'-benzyl-6-chloro-1H-spiro[furo[3,4-c]pyridine-3,4'-piperidin]-1-one (0.60 g, 1.0 eq) and tetrakis(triphenylphosphine) palladium (0) (0.021 g, 0.01 eq) in tetrahydrofuran (3.1 ml) at 0-5° C., was added dimethylzinc 2M solution in toluene (0.50 ml, 0.55 eq). The mixture was stirred at 70° C. for 4 h. The reaction mixture was partitioned between dichloromethane and aqueous saturated sodium bicarbonate solution. The layers were separated. The aqueous layer was extracted with dichloromethane. The combined organic layers were dried over anhydrous sodium sulfate, filtered and concentrated in vacuo. The title compound was obtained in 87% yield as a brown solid after purification by flash chromatography. MS m/e: 310 ([M+H]$^+$).

N-Benzylpiperidine Intermediate 7

1'-Benzyl-4-methyl-3H-spiro[isobenzofuran-1,4'-piperidine]

a) 1-Benzyl-4-(2-(hydroxymethyl)-3-methylphenyl)piperidin-4-ol

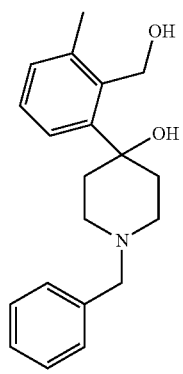 [SMILES: Cc1cccc(C2(O)CCN(Cc3ccccc3)CC2)c1CO]

To a solution of lithium aluminum hydride (0.27 g, 7.2 mmol) in tetrahydrofuran (14 ml) was added 1'-benzyl-4-methyl-3H-spiro[isobenzofuran-1,4'-piperidin]-3-one (2.2 g, 7.2 mmol) as a solution in tetrahydrofuran (7 ml) at 0-5° C. The ice bath was removed after 10 minutes and stirring was continued for 3 d. The reaction mixture was quenched by addition of water (0.27 ml), 2 M aqueous sodium hydroxide solution (0.27 ml) and again water (0.81 ml) and stirred for 1 h. The precipitate was removed by filtration and washed with tetrahydrofuran. The filtrate was concentrated in vacuo to give the title compound (2.2 g, quantitative) as white solid. MS m/e: 312 [(M+H)$^+$].

b) 1-Benzyl-4-(2-(chloromethyl)-3-methylphenyl)piperidin-4-ol

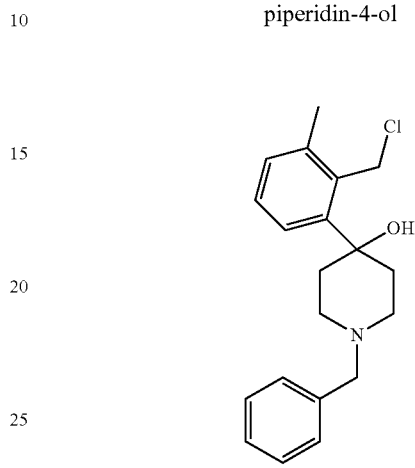

To a solution of 1-benzyl-4-(2-(hydroxymethyl)-3-methylphenyl)piperidin-4-ol (2.2 g, 7.2 mmol), 4-(N,N-dimethylamino)-pyridine (0.044 g, 0.36 mmol) and triethylamine (12 ml, 15 mmol) in tetrahydrofuran (29 ml) was added methanesulfonyl chloride (0.56 ml, 7.2 mmol) at 0-5° C. The ice bath was removed after 5 minutes and stirring was continued for 1 h. The reaction mixture was heated at reflux for 15 h. The reaction mixture was concentrated in vacuo. The residue was partitioned between ethyl acetate (50 ml) and 1 M aqueous sodium hydroxide solution (50 ml). The layers were separated. The aqueous layer was extracted with two 50-ml portions of ethyl acetate. The combined organic layers were washed with one 30-ml portion of brine, dried over anhydrous sodium sulfate, filtered and concentrated in vacuo. Flash chromatography with n-heptane/isopropanol as eluent gave the title compound (1.9 g, 64%) as light yellow viscous oil with a purity of approximately 80% according to NMR. MS m/e: 330 [(M+H)$^+$].

c) 1'-Benzyl-4-methyl-3H-spiro[isobenzofuran-1,4'-piperidine]

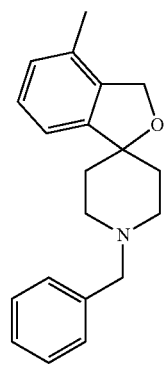 [SMILES: Cc1cccc2c1COC21CCN(Cc2ccccc2)CC1]

To a mixture of sodium hydride (0.33 g, 6.9 mmol) in tetrahydrofuran (20 ml) was added 1-benzyl-4-(2-(chloromethyl)-3-methylphenyl)piperidin-4-ol (1.9 g, 5.7 mmol) as a solution in tetrahydrofuran (5 ml) at 0-5° C. The ice bath was removed and stirring was continued for 20 h. The reaction mixture was quenched with water (1 ml) at 0-5° C. and partitioned between ethyl acetate (50 ml) and 0.5 M aqueous sodium hydroxide solution (50 ml). The layers were separated. The aqueous layer was extracted with two 50-ml portions of ethyl acetate. The combined organic layers were washed with one 30-ml portion of brine, dried over anhydrous sodium sulfate, filtered and concentrated in vacuo to give the title compound (1.8 g, quantitative) as off-white solid. MS m/e: 294 [(M+H)$^+$].

N-Benzylpiperidine Intermediate 8

1'-Benzyl-5,5-dimethyl-5H-spiro[furo[3,4-b]pyridine-7,4'-piperidine]

a) 1-Benzyl-4-(3-(2-hydroxypropan-2-yl)pyridin-2-yl)piperidin-4-ol

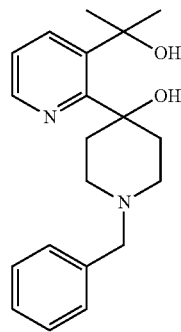 [SMILES: CC(C)(O)c1cccnc1C1(O)CCN(Cc2ccccc2)CC1]

To a solution of 2-(2-bromopyridin-3-yl)propan-2-ol (2.4 g, 11 mmol) in tetrahydrofuran (37 ml) was added n-butyllithium, 1.6 M in n-hexane (15 ml, 23 mmol) at −78° C. The reaction mixture was stirred for 10 minutes. 1-Benzylpiperidin-4-one (2.5 g, 13 mmol) was added in a quick fashion as a solution in tetrahydrofuran (5 ml). The dry ice/acetone bath was removed after 30 minutes and stirring was continued for 2 h. The reaction mixture was quenched with water (5 ml) and partitioned between ethyl acetate (100 ml) and 1 M aqueous sodium hydroxide solution (100 ml). The layers were separated. The aqueous layer was extracted with two 100-ml portions of ethyl acetate. The combined organic layers were washed with one 30-ml portion of brine, dried over anhydrous sodium sulfate, filtered and concentrated in vacuo. Flash with n-heptane/isopropanol as eluent gave the title compound with a purity of 10-20% according to NMR. Purification by Kugelrohr distillation (1-2 mbar, 120° C.) gave the title compound (0.58 g, 11%) as brown solid with a purity of approximately 70% according to NMR. MS m/e: 327.5 [(M+H)$^+$].

b) 1'-Benzyl-5,5-dimethyl-5H-spiro[furo[3,4-b]pyridine-7,4'-piperidine]

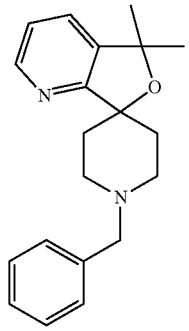 [SMILES: CC1(C)OC2(CCN(Cc3ccccc3)CC2)c2ncccc21]

To a solution of 1-benzyl-4-(3-(2-hydroxypropan-2-yl)pyridin-2-yl)piperidin-4-ol (0.58 g, 1.8 mmol) and triethylamine (0.52 ml, 3.8 mmol) in tetrahydrofuran (9.0 ml) was added methanesulfonyl chloride (0.15 ml, 1.9 mmol). The reaction mixture was stirred for 2 h at room temperature and for 5 h at reflux. The reaction mixture was partitioned between ethyl acetate (50 ml) and 1 M aqueous sodium hydroxide solution (30 ml). The layers were separated. The aqueous layer was extracted with two 50-ml portions of ethyl acetate. The combined organic layers were washed with one 30-ml portion of brine, dried over anhydrous sodium sulfate, filtered and concentrated in vacuo. Flash chromatography with n-heptane/isopropanol gave the title compound (0.22 g, 40%) as light brown solid. MS m/e: 309 [(M+H)$^+$].

N-Benzylpiperidine Intermediate 9

1'-Benzyl-6-methyl-3H-spiro[furo[3,4-c]pyridine-1,4'-piperidine]

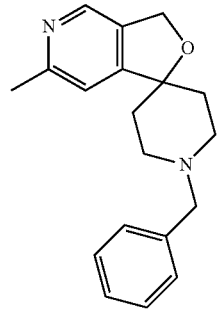 [SMILES: Cc1cc2c(cn1)COC21CCN(Cc2ccccc2)CC1]

To a solution of 1'-benzyl-6-methyl-3H-spiro[furo[3,4-c]pyridine-1,4'-piperidin]-3-one (0.20 g, 1.0 eq) in dichloromethane (7 ml) at −78° C., was added diisobutylaluminium hydride (1.3 ml, 2.0 eq). The mixture was stirred at −78° C. for 1 h. Pyridine (0.16 ml, 3.0 eq), 4-(N,N-dimethylamino)-pyridine (0.16 g, 2.0 eq) and acetic anhydride (0.37 ml, 6.0 eq) were then added. The mixture was stirred at −78° C. for 12 h then warmed to room temperature. The reaction mixture was partitioned between 7.5 ml aqueous saturated ammonium chloride and 5 ml saturated sodium potassium tartrate solution and stirred for 30 minutes. The reaction mixture was poured into aqueous saturated sodium bicarbonate solution and extracted with dichloromethane. The combined organic layers were dried over anhydrous sodium sulfate, filtered and concentrated in vacuo. The resulting acyl-hemiacetal was used as such in the next step. To a solution of the acyl-hemiacetal intermediate (0.28 g, 1.0 eq) in dichloromethane (10 ml) at room temperature, was added triethylsilane (0.95 ml, 7.5 eq) and trifluoroborane diethyl etherate (0.76 ml, 7.5 eq). The mixture was stirred at 40° C. for 25 minutes. The reaction mixture was partitioned between aqueous saturated sodium bicarbonate solution and dichloromethane. The aqueous layer was extracted with dichloromethane. The combined organic layers were dried over anhydrous sodium sulfate, filtered and concentrated in vacuo. The title compound was obtained after flash chromatography as white solid in 39% yield. MS m/e: 296 ([M+H]$^+$).

N-Benzylpiperidine intermediate 10

1'-Benzyl-6-methyl-1H-spiro[furo[3,4-c]pyridine-3,4'-piperidine]

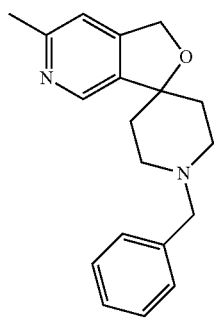 [SMILES: Cc1cc2c(cn1)C1(CCN(Cc3ccccc3)CC1)OC2]

To a solution of 1'-benzyl-6-methyl-1H-spiro[furo[3,4-c]pyridine-3,4'-piperidin]-1-one (0.20 g, 1.00 eq) in dichloromethane (7 ml) at −78° C., was added diisobutylaluminium hydride (1.3 ml, 2.0 eq). The mixture was stirred at −78° C. for 1 h. Pyridine (0.16 ml, 3.0 eq), 4-(N,N-dimethylamino)-pyridine (0.16 g, 2.0 eq) and acetic anhydride (0.37 ml, 6.0 eq) were then added. The mixture was stirred at −78° C. for 12 h then warmed to room temperature. The reaction mixture was partitioned between 7.5 ml aqueous saturated ammonium chloride solution and 5 ml saturated sodium potassium tartrate solution and stirred for 30 minutes. The reaction mixture was poured into aqueous saturated sodium bicarbonate solution and extracted with dichloromethane. The combined organic layers were dried over anhydrous sodium sulfate, filtered and concentrated in vacuo. The resulting acyl-hemiacetal was filtered through a plug of silica and used as such in the next step. To a solution of the acyl-hemiacetal intermediate (0.09 g, 1 eq) in dichloromethane (4.7 ml) at room temperature, was added triethylsilane (0.31 ml, 7.5 eq) and trifluoroborane diethyl etherate (0.24 ml, 7.5 eq). The mixture was stirred at 40° C. for 12 h. The reaction mixture was partitioned between 1 M aqueous sodium hydroxide solution and dichloromethane. The aqueous layer was extracted with dichloromethane. The combined organic layers were dried over anhydrous sodium sulfate, filtered and concentrated in vacuo. The title compound was obtained after flash chromatography as light yellow oil in 32% yield. MS m/e: 295 ([M+H]$^+$).

Spiropiperidines of Formula (II)

General Procedure VII: Hydrogenolytic N-debenzylation

An intermediate of formula (XXXIV) or (XXXVII) (1 eq) is dissolved in a solvent such as ethanol (0.1-0.3 M). The flask is evacuated until the solvent begins to bubble gently and back-filled with Argon after 10-30 s. This procedure is repeated twice. After addition of a catalyst such as palladium, 10% on activated charcoal (0.05-0.1 eq), the flask is evacuated until the solvent begins to bubble and back-filled with hydrogen. The reaction mixture is stirred under an atmosphere of 1 bar hydrogen gas for 2-48 h. The catalyst is removed by filtration over Decalite and washed with a solvent. The filtrate is concentrated in vacuo to give a spiropiperidine of formula (II).

General Procedure VIII: N-BOC Deprotection with Hydrogen Chloride

A solution of an intermediate of formula (XXIX) (1 eq) in 4 M hydrogen chloride solution (10-20 eq HCl) in 1,4-dioxane is stirred for 6-24 h. The reaction mixture is partitioned between 1 M aqueous sodium hydroxide solution and an organic solvent, e.g. ethyl acetate or dichloromethane. The layers are separated and the aqueous layer is extracted with two portions of the organic solvent. The combined organic layers are dried over anhydrous sodium sulfate, filtered and concentrated in vacuo to give a spiropiperidine of formula (II).

General Procedure IX: N-BOC Deprotection with Trifluoroacetic Acid

A solution of an intermediate of formula (XXIX) (1 eq) in dichloromethane (0.1-1.0 M) and trifluoroacetic acid (10-20 eq) is stirred for 6-24 h. The reaction mixture is partitioned between 1 M aqueous sodium hydroxide solution and an organic solvent, e.g. ethyl acetate or dichloromethane. The layers are separated and the aqueous layer is extracted with two portions of the organic solvent. The combined organic layers are dried over anhydrous sodium sulfate, filtered and concentrated in vacuo to give a spiropiperidine of formula (II).

Spiropiperidine 1

4-Methyl-3H-spiro[isobenzofuran-1,4'-piperidin]-3-one

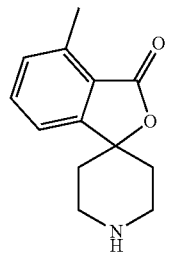 [SMILES: Cc1cccc2c1C(=O)OC21CCNCC1]

The title compound was obtained as white solid in 95% yield according to the general procedure VII from 1'-benzyl-4-methyl-3H-spiro[isobenzofuran-1,4'-piperidin]-3-one. MS m/e: 218 [(M+H)$^+$].

Spiropiperidine 2

5,6-Dimethoxy-3H-spiro[isobenzofuran-1,4'-piperidin]-3-one

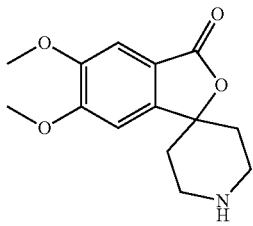 [SMILES: COc1cc2c(cc1OC)C1(CCNCC1)OC2=O]

The title compound was obtained as white solid in 97% yield according to the general procedure VII from 1'-benzyl-5,6-dimethoxy-3H-spiro[isobenzofuran-1,4'-piperidin]-3-one. MS m/e: 264 [(M+H)$^+$].

Spiropiperidine 3

3-Methyl-5H-spiro[furo[3,4-b]pyridine-7,4'-piperidin]-5-one

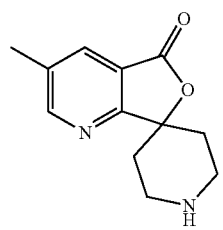 [SMILES: Cc1cnc2c(c1)C(=O)OC21CCNCC1]

The title compound was obtained as white solid in 86% yield according to the general procedure IX from tert-butyl 3-methyl-5-oxo-5H-spiro[furo[3,4-b]pyridine-7,4'-piperidine]-1'-carboxylate. MS m/e: 219 [(M+H)$^+$].

Spiropiperidine 4

3-Methyl-7H-spiro[furo[3,4-b]pyridine-5,4'-piperidin]-7-one

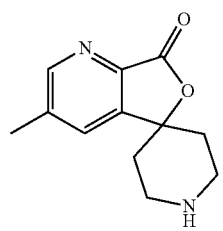 [SMILES: Cc1cnc2c(c1)C1(CCNCC1)OC2=O]

The title compound was obtained as white solid in 72% yield according to the general procedure IX from tert-butyl 3-methyl-7-oxo-7H-spiro[furo[3,4-b]pyridine-5,4'-piperidine]-1'-carboxylate. MS m/e: 219 [(M+H)$^+$].

Spiropiperidine 5

2-Methyl-5H-spiro[furo[3,4-b]pyridine-7,4'-piperidin]-5-one

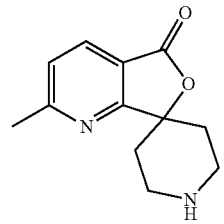 [SMILES: Cc1ccc2c(n1)C1(CCNCC1)OC2=O]

The title compound was obtained as white solid in 73% yield according to the general procedure IX from tert-butyl 2-methyl-5-oxo-5H-spiro[furo[3,4-b]pyridine-7,4'-piperidine]-1'-carboxylate. MS m/e: 219 [(M+H)$^+$]

Spiropiperidine 6

2-Methyl-7H-spiro[furo[3,4-b]pyridine-5,4'-piperidin]-7-one

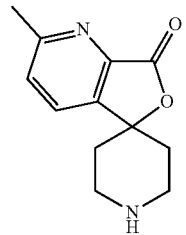 [SMILES: Cc1ccc2c(n1)C(=O)OC21CCNCC1]

The title compound was obtained as white solid in 95% yield according to the general procedure VII from 1'-benzyl-2-methyl-7H-spiro[furo[3,4-b]pyridine-5,4'-piperidin]-7-one. MS m/e: 219 [(M+H)$^+$].

Spiropiperidine 7

6-Methyl-3H-spiro[furo[3,4-c]pyridine-1,4'-piperidin]-3-one

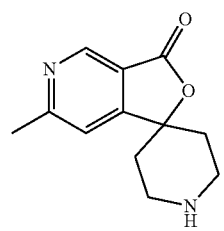 [SMILES: Cc1cc2c(cn1)C(=O)OC21CCNCC1]

The title compound was obtained as yellow oil in quantitative yield according to the general procedure VII from 1'-benzyl-6-methyl-3H-spiro[furo[3,4-c]pyridine-1,4'-piperidin]-3-one. MS m/e: 220 ([M+H]$^+$).

Spiropiperidine 8

6-Methyl-1H-spiro[furo[3,4-c]pyridine-3,4'-piperidin]-1-one

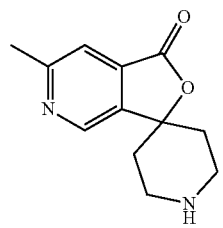 [SMILES: Cc1cc2c(cn1)C1(CCNCC1)OC2=O]

The title compound was obtained as yellow oil in 82% yield according to the general procedure VII from 1'-benzyl-6-methyl-1H-spiro[furo[3,4-c]pyridine-3,4'-piperidin]-1-one. MS m/e: 219 ([M+H]$^+$).

Spiropiperidine 9

6-chloro-1H-spiro[furo[3,4-c]pyridine-3,4'-piperidin]-1-one and 4-chloro-1H-spiro[furo[3,4-c]pyridine-3,4'-piperidin]-1-one

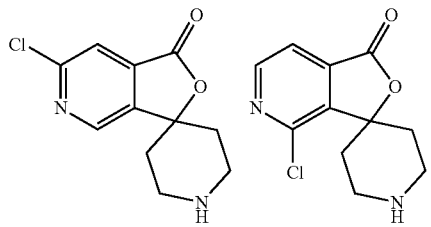

In a 50 ml round-bottomed flask, 5-bromo-2-chloroisonicotinic acid (1.0 g, 4.2 mmol, 1.0 eq) was combined with tetrahydrofuran (18 ml) to give a brown solution. At −78° C., n-butyllithium (1.6 M in hexane, 5.3 ml, 2.0 eq) was added within 10 minutes. After 10 minutes stirring at −78° C., tert-butyl 4-oxopiperidine-1-carboxylate (0.84 g, 1.0 eq) was added. The reaction mixture was stirred at −78° C. for 30 minutes then warmed to room temperature. 25 ml water and 25 ml ethyl acetate were added. The layers were separated and the aqueous layer was acidified to pH 1 with concentrated hydrochloric acid. The resulting mixture was stirred at 100° C. for 30 minutes. The reaction was cooled down, neutralized with solid sodium bicarbonate and extracted with ethyl acetate (3×20 ml). The combined organic layers were dried over anhydrous sodium sulfate, filtered and concentrated in vacuo. The title compound was obtained after purification by flash chromatography in 4% yield containing approximately 10% of regioisomeric 4-chloro-1H-spiro[furo[3,4-c]pyridine-3,4'-piperidin]-1-one. MS m/e: 239 ([M+H]$^+$).

Spiropiperidine 10

4-Methyl-3H-spiro[isobenzofuran-1,4'-piperidine]

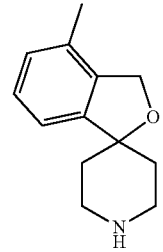

The title compound was obtained as white solid in 60% yield according to the general procedure VII from 1'-benzyl-4-methyl-3H-spiro[isobenzofuran-1,4'-piperidine]. MS m/e: 204 [(M+H)$^+$].

Spiropiperidine 11

3-Methyl-7H-spiro[furo[3,4-b]pyridine-5,4'-piperidine]

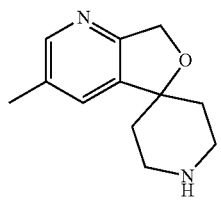

The title compound was obtained as white solid in 88% yield according to the general procedure IX from tert-butyl 3-methyl-7H-spiro[furo[3,4-b]pyridine-5,4'-piperidine]-1'-carboxylate. MS m/e: 205 [(M+H)$^+$].

Spiropiperidine 12

3-Methyl-5H-spiro[furo[3,4-b]pyridine-7,4'-piperidine]

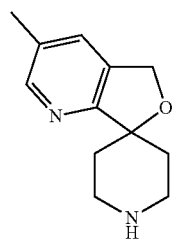

The title compound was obtained as viscous oil in 88% yield according to the general procedure IX from tert-butyl 3-methyl-5H-spiro[furo[3,4-b]pyridine-7,4'-piperidine]-1'-carboxylate. MS m/e: 205 [(M+H)$^+$].

Spiropiperidine 13

2-Methyl-5H-spiro[furo[3,4-b]pyridine-7,4'-piperidine]

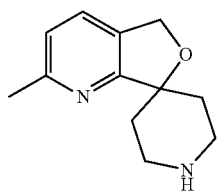

The title compound was obtained as colorless oil in 85% yield according to the general procedure IX from tert-butyl 2-methyl-5H-spiro[furo[3,4-b]pyridine-7,4'-piperidine]-1'-carboxylate. MS m/e: 205 [(M+H)$^+$].

Spiropiperidine 14

2-Methyl-7H-spiro[furo[3,4-b]pyridine-5,4'-piperidine]dihydrochloride

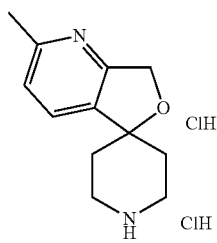

The title compound was obtained as white solid in 95% yield according to the general procedure VIII from tert-butyl 2-methyl-7H-spiro[furo[3,4-b]pyridine-5,4'-piperidine]-1'-carboxylate. MS m/e: 205 [(M+H)$^+$].

Spiropiperidine 15

6-Methyl-3H-spiro[furo[3,4-c]pyridine-1,4'-piperidine]

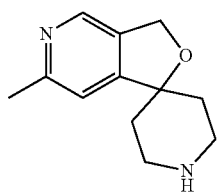

The title compound was obtained as white gum in quantitative yield according to the general procedure VII from 1'-benzyl-6-methyl-3H-spiro[furo[3,4-c]pyridine-1,4'-piperidine. MS m/e: 205 ([M+H]$^+$).

Spiropiperidine 16

6-Methyl-1H-spiro[furo[3,4-c]pyridine-3,4'-piperidine]

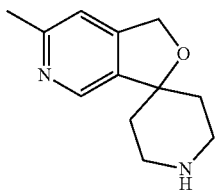

The title compound was obtained as yellow oil in 96% yield according to the general procedure VII 1'-benzyl-6-methyl-1H-spiro[furo[3,4-c]pyridine-3,4'-piperidine. MS m/e: 205 ([M+H]$^+$).

Spiropiperidine 17

5,5-Dimethyl-5H-spiro[furo[3,4-b]pyridine-7,4'-piperidine]

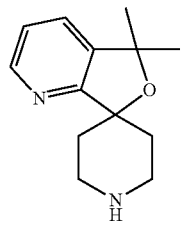 [SMILES: CC1(C)OC2(CCNCC2)c2ncccc21]

The title compound was obtained as light brown solid in 85% yield according to the general procedure VII from 1'-benzyl-5,5-dimethyl-5H-spiro[furo[3,4-b]pyridine-7,4'-piperidine]. MS m/e: 219 [(M+H)$^+$].

Spiropiperidine 18

7,7-Dimethyl-7H-spiro[furo[3,4-b]pyridine-5,4'-piperidine]

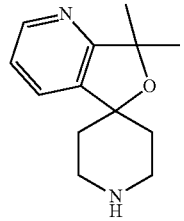 [SMILES: CC1(C)OC2(CCNCC2)c2cccnc21]

The title compound was obtained as white solid in 92% yield according to the general procedure IX from tert-butyl 7,7-dimethyl-7H-spiro[furo[3,4-b]pyridine-5,4'-piperidine]-1'-carboxylate. MS m/e: 219 [(M+H)$^+$].

Diazoketone Intermediates of Formula (XXIV)

General Procedure X:

To a solution of an acid chloride intermediate of formula (XXIII) in acetonitrile (0.5 M) is added dropwise 2.0 M solution of trimethylsilyl diazomethane (2.1 eq) in n-hexane at 0-5° C. The ice bath is removed after 10 minutes and stirring is continued until complete reaction is observed (2-15 h). Excess trimethylsilyl diazomethane is quenched by slow addition of acetic acid (1 eq) at room temperature. The reaction mixture is concentrated to dryness. Purification by flash-chromatography gives a diazoketone intermediate of formula (XXIV).

Diazoketone 1

1-Diazo-3-(4-methylphenyl)propan-2-one

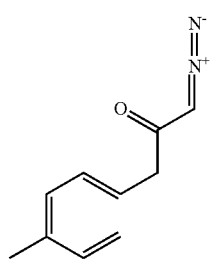

The title compound was obtained as white solid in 92% yield according to the general procedure X from p-tolylacetic acid chloride and (trimethylsilyl)-diazomethane. MS m/e: 175 ([M+H]$^+$).

Diazoketone 2

1-Diazo-3-(4-methoxyphenyl)propan-2-one

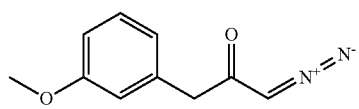

The title compound was obtained as brown oil in quantitative yield according to the general procedure X from 3-methoxyphenylacetic acid chloride and (trimethylsilyl)-diazomethane. MS m/e: 191 ([M+H]$^+$).

Diazoketone 3

1-Diazo-3-(3,4-dimethoxyphenyl)propan-2-one

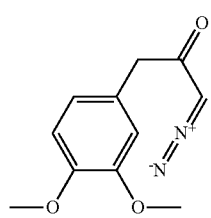

The title compound was obtained as orange liquid according to the general procedure X from 3,4-dimethoxyphenylacetic acid chloride and (trimethylsilyl)-diazomethane. MS m/e: 212 ([M+H]$^+$).

Diazoketone 4

1-(2-Chloro-5-methoxyphenyl)-3-diazopropan-2-one

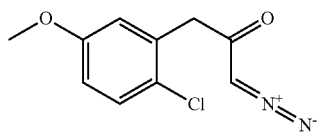

To a solution of 2-(2-chloro-5-methoxyphenyl)acetic acid (5.0 g, 24.9 mmol) in dichloromethane (83 ml) were added thionyl chloride (2.73 ml, 37.4 mmol) and a catalytic amount of N.N-dimethylformamide at 0-5° C. The cooling bath was removed after 10 minutes, and stirring was continued for 16 h. The solvent was evaporated to give the crude 2-(2-chloro-5-methoxyphenyl)acetic acid chloride intermediate. The title compound was obtained as yellow solid in 63% yield according to the general procedure X from 2-(2-chloro-5-methoxyphenyl)acetic acid chloride and (trimethylsilyl)-diazomethane. MS m/e: 225 ([M+H]$^+$).

2-Indanone Intermediates of Formula (XIV)

General Procedure XI:

To a solution of rhodium (II) acetate dimer (0.01 eq) in dichloromethane (0.002 M) is added a solution of a diazoketone intermediate of formula (XXIV) in dichloromethane (0.2 M) dropwise at 0-5° C. The reaction mixture is concentrated to dryness. Purification by flash-chromatography or Kugelrohr distillation gives a 2-indanone intermediate of formula (XIV).

2-Indanone Intermediate 1

5-Methyl-1,3-dihydro-2H-inden-2-one

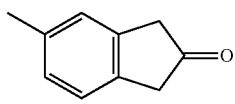

The title compound was obtained as off-white solid in 29% yield according to the general procedure XI from 1-diazo-3-(4-methylphenyl)propan-2-one. MS m/e: 146 (M+).

2-Indanone Intermediate 2

5-Methoxy-1,3-dihydro-2H-inden-2-one

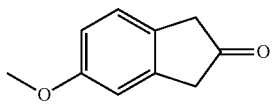

The title compound was obtained as off-white solid in 29% yield according to the general procedure XI from 1-diazo-3-(3-methoxyphenyl)propan-2-one. MS m/e: 163 ([M–H]+).

2-Indanone intermediate 3

5,6-Dimethoxy-1H-inden-2(3H)-one

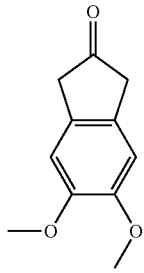

The title compound was obtained as orange semi-solid in 45% yield according to the general procedure XI from 1-diazo-3-(3,4-dimethoxyphenyl)propan-2-one. MS m/e: 192 ([M]+).

2-Indanone Intermediate 4

5,6-Difluoro-1,3-dihydro-2H-inden-2-one

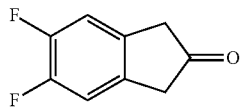

To a solution of 5,6-difluoro-2,3-dihydro-1H-inden-2-ol (2.6 g, 16 mmol) in dichloromethane (54 ml) was added Dess-Martin periodinane (8.5 g, 20 mmol) at room temperature. The reaction mixture was stirred for 7 h. Diethyl ether (250 ml) was added to the reaction mixture and stirring was continued for 15 minutes. The precipitate was removed by filtration and washed with diethyl ether. The filtrate was washed with one 150-ml portion of saturated aqueous saturated bicarbonate solution. The layers were separated. The aqueous layer was extracted with two 150-ml portions of diethyl ether. The combined organic layers were washed with one 150-ml portion of brine, dried over anhydrous sodium sulfate, filtered and concentrated in vacuo. Flash-chromatography with n-heptane/ethyl acetate gave the title compound (1.8 g, 69%) as white solid. MS m/e: 167 ([M–H]−).

2-Indanone Intermediate 5

4-Chloro-7-methoxy-1H-inden-2(3H)-one

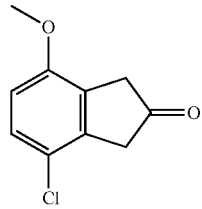

The title compound was obtained as light yellow solid in 21% yield according to the general procedure XI from 1-(2-chloro-5-methoxyphenyl)-3-diazopropan-2-one. MS m/e: 195 ([M–H]−]−).

Cyanohydrin Intermediates of Formula (XV) and trimethylsilyl cyanohydrin Intermediates of Formula (XVI)

General Procedure XV: Copper Catalyzed

A solution of a 2-indanone intermediate of formula (XIV), trimethylsilyl cyanide (2.6 eq) and copper(II) trifluoromethanesulfonate (0.01 eq) in dichloromethane (0.5-1.0 M) is stirred at room temperature for 15-24 h. The reaction mixture is concentrated to dryness to give a trimethylsilyl cyanohydrin intermediate of formula (XVI). The crude compound of formula (XVI) is partitioned between an organic solvent such as dichloromethane and water. The layers are separated. The aqueous layer is extracted with one or two portions of organic solvent. The combined organic layers are washed with one portion of brine, dried over anhydrous sodium sulfate, filtered and concentrated to dryness to give an intermediate of formula (XVI). During the work-up the trimethylsilyl group of the resulting trimethylsilyl cyanohydrin may be partially or completely cleaved to give a cyanohydrin intermediate of formula (XV).

General Procedure XVI: Lanthanum Catalyzed

A solution of a 2-indanone intermediate of formula (XIV), 2-hydroxy-2-methylpropanenitrile (1.5 eq) and lanthanum (III) isopropoxide (0.1 eq) in tetrahydrofuran (0.5-1.0 M) is stirred at room temperature for 15-24 h. The reaction mixture is partitioned between an organic solvent such as ethyl acetate or tert-butyl methyl ether and saturated aqueous ammonium chloride solution. The layers are separated. The aqueous layer is extracted with one or two portions of organic solvent. The combined organic layers are washed with one portion of brine, dried over anhydrous sodium sulfate, filtered and concentrated to dryness. Purification by flash-chromatography gives a cyanohydrin intermediate of formula (XV).

117

Cyanohydrin 1

2-[(Trimethylsilyl)oxy]-2,3-dihydro-1H-indene-2-carbonitrile

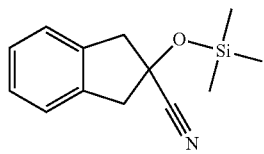 [SMILES: C[Si](C)(C)OC1(C#N)Cc2ccccc2C1]

The title compound was obtained as light brown oil in quantitative yield according to the general procedure XV from 2-indanone and trimethylsilyl cyanide. MS m/e: 231 (M+)

Cyanohydrin 2

5-Methyl-2-[(trimethylsilyl)oxy]-2,3-dihydro-1H-indene-2-carbonitrile

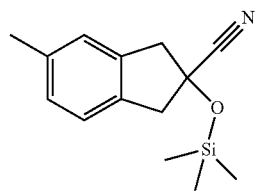 [SMILES: Cc1ccc2c(c1)CC(C#N)(O[Si](C)(C)C)C2]

The title compound was obtained as yellow oil in 95% yield according to the general procedure XV from 5-methyl-1,3-dihydro-2H-inden-2-one and trimethylsilyl cyanide.

Cyanohydrin 3

5-Methoxy-2-[(trimethylsilyl)oxy]-2,3-dihydro-1H-indene-2-carbonitrile

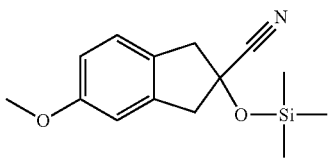

The title compound was obtained as brown oil in 97% yield according to the general procedure XV from 5-methoxy-1,3-dihydro-2H-inden-2-one and trimethylsilyl cyanide. MS m/e: 261 (M+).

118

Cyanohydrin 4

5,6-Difluoro-2-[(trimethylsilyl)oxy]-2,3-dihydro-1H-indene-2-carbonitrile

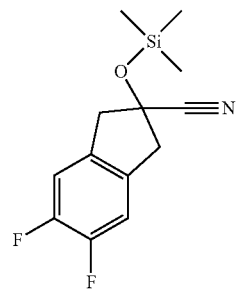 [SMILES: C[Si](C)(C)OC1(C#N)Cc2cc(F)c(F)cc2C1]

The title compound was obtained as yellow oil in 66% yield with a purity of approximately 70% (by NMR) according to the general procedure XV from 5,6-difluoro-1,3-dihydro-2H-inden-2-one and trimethylsilyl cyanide.

Cyanohydrin 5

5,6-Dimethoxy-2-(trimethylsilyloxy)-2,3-dihydro-1H-indene-2-carbonitrile

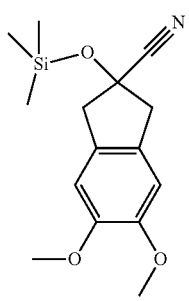 [SMILES: COc1cc2c(cc1OC)CC(C#N)(O[Si](C)(C)C)C2]

The title compound was obtained as dark red oil in 100% yield according to the general procedure XV from 5,6-dimethoxy-1H-inden-2(3H)-one and trimethylsilyl cyanide. MS m/e: 291 ([M+]$^+$).

Cyanohydrin 6

1-(Trimethylsilyloxy)-2,3-dihydro-1H-indene-1-carbonitrile

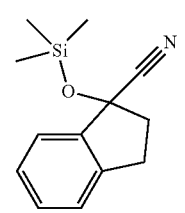 [SMILES: C[Si](C)(C)OC1(C#N)CCc2ccccc21]

The title compound was obtained as yellow oil in 74% yield according to the general procedure XV from 2,3-dihydro-1H-inden-1-one and trimethylsilyl cyanide.

Cyanohydrin 7

2-Hydroxy-1,2,3,4-tetrahydronaphthalene-2-carbonitrile

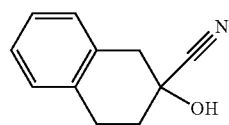 [SMILES: N#CC1(O)CCc2ccccc2C1]

The title compound was obtained as light brown oil in 20% yield according to the general procedure XVI from 3,4-dihydronaphthalen-2(1H)-one and 2-hydroxy-2-methyl-propanenitrile.

Cyanohydrin 8

1-(Trimethylsilyloxy)-1,2,3,4-tetrahydronaphthalene-1-carbonitrile

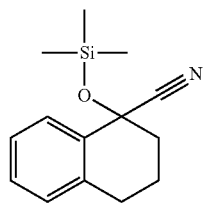 [SMILES: C[Si](C)(C)OC1(C#N)CCCc2ccccc21]

The title compound was obtained as yellow oil in 72% yield according to the general procedure XVI from 3,4-dihydronaphthalen-1(2H)-one, trimethylsilanecarbonitrile and copper(II) trifluoromethanesulfonate. MS m/e: 246 ([M+H]$^+$).

Cyanohydrin 9

4-Chloro-7-methoxy-2-(trimethylsilyloxy)-2,3-dihydro-1H-indene-2-carbonitrile

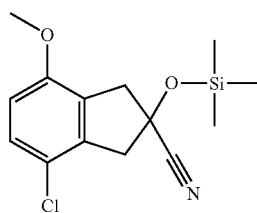 [SMILES: COc1ccc(Cl)c2c1CC(C#N)(O[Si](C)(C)C)C2]

The title compound was obtained as brown oil in quantitative yield according to the general procedure XV from 4-chloro-7-methoxy-1H-inden-2(3H)-one and trimethylsilyl cyanide.

Malonic Acid Ester Intermediates of Formula (XX)

General Procedure XII:

To a mixture of sodium hydride (2.1 eq) in tetrahydrofuran (1.0 M) is added a malonate derivative (1.1 eq) of formula (XVIII). The reaction mixture is stirred for 1 h. A solution of an alkylating reagent (1.0 eq) of formula (XIX) is added dropwise as a solution in tetrahydrofuran (1.0 M). The reaction mixture is stirred for 1-24 h and then quenched with saturated aqueous ammonium chloride solution at room temperature. The reaction mixture is partitioned between an organic solvent such as ethyl acetate or tert-butyl methyl ether and saturated aqueous ammonium chloride solution. The layers are separated. The aqueous layer is extracted with one or two portions of organic solvent. The combined organic layers are washed with one portion of brine, dried over anhydrous sodium sulfate, filtered and concentrated to dryness. Purification by flash-chromatography gives an intermediate of formula (XX).

Malonic Acid Ester Intermediate 1

2-tert-Butyl 2-ethyl 5,6-dimethyl-1H-indene-2,2(3H)-dicarboxylate

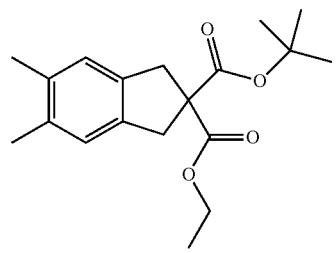 [SMILES: CCOC(=O)C1(C(=O)OC(C)(C)C)Cc2cc(C)c(C)cc2C1]

The title compound was obtained as colorless oil in 86% yield from 1,2-bis(chloromethyl)-4,5-dimethylbenzene and tert-butyl ethyl malonate according to the general procedure XII. MS m/e: 263 ([M-C$_4$H]$^+$).

Malonic Acid Intermediates of Formula (XXI)

General Procedure XIII:

To a solution of a compound of formula (XX) in a solvent such dichloromethane (0.1-0.5 M) is added trifluoro acetic acid (10-20 eq) at 0-5° C. The cooling bath is removed after 10-30 minutes and stirring is continued for 16-24 h. The reaction mixture is partitioned between an organic solvent such as ethyl acetate or dichloromethane and saturated aqueous ammonium chloride solution. The layers are separated. The aqueous layer is extracted with one or two portions of organic solvent. The combined organic layers are washed with one portion of brine, dried over anhydrous sodium sulfate, filtered and concentrated to dryness to give a compound of formula (XXI).

Malonic Acid 1

2-(Ethoxycarbonyl)-5,6-dimethyl-2,3-dihydro-1H-indene-2-carboxylic acid

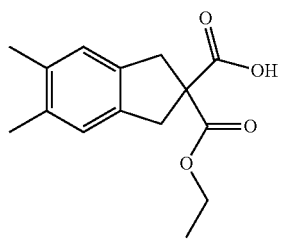 [SMILES: CCOC(=O)C1(C(=O)O)Cc2cc(C)c(C)cc2C1]

The title compound was obtained as grey solid in 95% yield from 2-tert-butyl 2-ethyl 5,6-dimethyl-1H-indene-2,2 (3H)-dicarboxylate according to the general procedure XIII. MS m/e: 261 ([M–H]⁻).

2-Indanecarboxvlic Ester Intermediates of Formula (XXII)

General Procedure XIV:

A solution of a compound of formula (XXI), lithium chloride (2.1 eq) and water (1.05 eq) in dimethyl sulfoxide (0.5 M) is stirred at 180° C. for 6 h. The reaction mixture is partitioned between an organic solvent such as ethyl acetate or tert-butyl methyl ether and 0.5 M aqueous hydrogen chloride solution. The layers are separated. The aqueous layer is extracted with one or two portions of organic solvent. The combined organic layers are washed with one portion of brine, dried over anhydrous sodium sulfate, filtered and concentrated to dryness. A solution of the crude reaction mixture in an alcohol such as ethanol or methanol is stirred at reflux with a catalytic amount of sulfuric acid for 6-24 h. The reaction mixture is concentrated to dryness. Purification by flash-chromatography gives an intermediate of formula (XXII).

2-Indanecarboxylic ester 1

Ethyl 5,6-dimethyl-2,3-dihydro-1H-indene-2-carboxylate

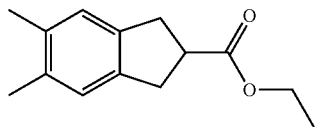 [SMILES: CCOC(=O)C1Cc2cc(C)c(C)cc2C1]

The title compound was obtained as light brown oil in 85% yield from 2-(ethoxycarbonyl)-5,6-dimethyl-2,3-dihydro-1H-indene-2-carboxylic acid according to the general procedure XIV. MS m/e: 218 ([M]⁺).

Alpha-hydroxy Ester Intermediates of Formula (XII) and (XVII)

General Procedure XVII: Cyanohydrin Hydrolysis with Aqueous Hydrogen Chloride

A solution of a cyanohydrin intermediate of formula (XV) or a trimethylsilyl cyanohydrin intermediate of formula (XVI) in an alcohol such as methanol or ethanol (0.3 M) and concentrated hydrochloric acid (20 eq) is refluxed for 6-24 h. The reaction mixture is partitioned between an organic solvent such as ethyl acetate or tert-butyl methyl ether and water. The layers are separated. The aqueous layer is extracted with one or two portions of organic solvent. The combined organic layers are washed with one portion of brine, dried over anhydrous sodium sulfate, filtered and concentrated to dryness. Purification by flash-chromatography gives an alpha-hydroxy ester intermediate of formula (XII).

General Procedure XVIII: Pinner-type Cyanohydrin Hydrolysis

A solution of a cyanohydrin intermediate of formula (XV) or a trimethylsilyl cyanohydrin intermediate of formula (XVI) and an alcohol such as methanol or ethanol (1 eq) in 4 M hydrochloric acid in 1,4-dioxane (4-10 eq) is stored overnight in the freezer or alternatively stirred over night at −10 to −5° C. Water is added to the reaction mixture and stirring is continued for 1-4 h. The reaction mixture is partitioned between an organic solvent such as ethyl acetate or tert-butyl methyl ether and water. The layers are separated. The aqueous layer is extracted with one or two portions of organic solvent. The combined organic layers are washed with one portion of brine, dried over anhydrous sodium sulfate, filtered and concentrated to dryness. Purification by flash-chromatography gives an alpha-hydroxy ester intermediate of formula (XII).

General Procedure XIX: Alpha-hydroxylation of 2-Indanecarboxylic Esters

To a solution of an 2-indanecarboxylic ester intermediate of formula (XXII) in tetrahydrofuran (0.5-1.0 M) is added 1.0 M lithium bis(trimethylsilyl)amide solution in tetrahydrofuran (1.1 eq) at −78° C. The cooling bath is removed and stirring is continued for 45 minutes at 0-5° C. A solution of (1S)-(+)-(10-camphorsulfonyl)oxaziridine (1.05 eq) as a solution in tetrahydrofuran (0.65 M) is added at max −55° C. The reaction mixture is stirred for 1-2 h. The cooling bath is removed and the reaction mixture is quenched by addition of saturated aqueous ammonium chloride solution at −20° C. The reaction mixture is partitioned between an organic solvent such as ethyl acetate or tert-butyl methyl ether and 0.5 M aqueous hydrogen chloride solution. The layers are separated. The aqueous layer is extracted with one or two portions of organic solvent. The combined organic layers are washed with one portion of brine, dried over anhydrous sodium sulfate, filtered and concentrated to dryness. Purification by flash-chromatography gives an alpha-hydroxy ester intermediate of formula (XII).

Alpha-hydroxy Ester 1

Ethyl 2-hydroxy-2,3-dihydro-1H-indene-2-carboxylate a) 2-Hydroxy-2,3-dihydro-1H-indene-2-carboxylate

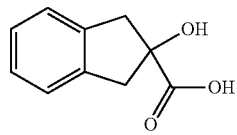 [SMILES: O=C(O)C1(O)Cc2ccccc2C1]

A slurry of 2-(trimethylsilyloxy)-2,3-dihydro-1H-indene-2-carbonitrile (21.0 g, 90.8 mmol) and concentrated hydrochloric acid (75.6 ml, 908 mmol) was stirred for 1 h at room temperature and for 4 h at 100° C. The reaction mixture was diluted with one 50-ml portion of water. The heating bath was removed and stirring was continued for 15 h. The precipitate was collected by filtration and washed with two 50-ml portions of 1 M aqueous hydrogen chloride solution. The wet precipitate was partitioned between ethyl acetate (150 ml) and 1 M aqueous sodium hydroxide solution (150 ml). The layers were separated. The organic layer was extracted with two 200-ml portions of 0.5 M aqueous sodium hydroxide solution. The combined aqueous layers were extracted with one 150-ml portion of ethyl acetate. The combined aqueous layers were acidified by addition of concentrated hydrochloric acid (35 ml). The aqueous layer was extracted with two 150-ml portions of ethyl acetate. The combined ethyl acetate layers from the acidic extraction were washed with one 50-ml portion of brine, dried over anhydrous sodium sulfate, filtered and concentrated in vacuo. The residue was triturated in diethyl ether (100 ml) for 3 h at room temperature. The precipitate was collected by filtration, washed with diethyl ether and dried in vacuo to give the title compound as off-white solid. Crystallization from hot ethyl acetate (90 ml) afforded the title compound (7.0 g, 43%) as white solid. MS m/e: 177 ([M–H]⁻).

b) Ethyl 2-hydroxy-2,3-dihydro-1H-indene-2-carboxylate

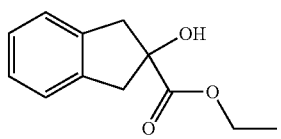

To a solution of 2-hydroxy-2,3-dihydro-1H-indene-2-carboxylic acid (4.0 g, 22.4 mmol) in ethanol (74.8 ml) was added a catalytic amount (3 drops) of sulfuric acid at room temperature. The reaction mixture was stirred for 48 h. The solvent was evaporated in vacuo. The residue was partitioned between ethyl acetate (150 ml) and 1 M sodium carbonate (50 ml). The layers were separated. The organic layer was washed with one 50-ml portion of brine, dried over anhydrous sodium sulfate, filtered and concentrated in vacuo to give the title compound (4.5 g, 97%) as white solid.

Alpha-hydroxy Ester 2

Ethyl 2-hydroxy-5-methoxy-2,3-dihydro-1H-indene-2-carboxylate a) 2-Hydroxy-5-methoxy-2,3-dihydro-1H-indene-2-carboxylate

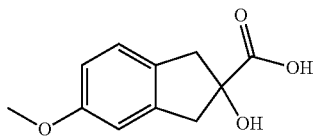

A solution of 5-methoxy-2-(trimethylsilyloxy)-2,3-dihydro-1H-indene-2-carbonitrile (4.98 g, 19.1 mmol) in toluene (12 ml) was added dropwise at 85-90° C. to a vigorously stirred solution of aqueous hydrochloride acid 25% (13.9 g, 12.4 ml, 95.3 mmol). The reaction mixture was stirred for 20 h and was then allowed to cool to room temperature. The mixture was partitioned between isopropyl acetate (50 ml) and water (30 ml). The layers were separated. The aqueous layer was extracted with two 50-ml portions of isopropyl acetate. The combined organic layers were washed with one 30-ml portion of brine, dried over anhydrous sodium sulfate, filtered and concentrated in vacuo. The residue was triturated in diethyl ether (50 ml). The solids were removed by filtration and washed with diethyl ether. The filtrate was concentrated in vacuo. The residue was partitioned between tert-butyl methyl ether (50 ml) and 1 M aqueous sodium hydroxide solution (50 ml). The layers were separated. The organic layer was extracted with two 50-ml portions of 1 M aqueous sodium hydroxide solution. The aqueous layer was extracted with one 100-ml portion of tert-butyl methyl ether. The combined aqueous layers were acidified by addition of 80 ml 2 M aqueous hydrogen chloride solution and extracted with three 50-ml portions of ethyl acetate. The combined ethyl acetate layers were dried over anhydrous sodium sulfate, filtered and concentrated in vacuo. Flash-chromatography with n-heptane/2-propanol gave the title compound (2.37 g, 60%) as brown solid. MS m/e: 207 ([M–H]⁻).

b) Ethyl 2-hydroxy-5-methoxy-2,3-dihydro-1H-indene-2-carboxylate

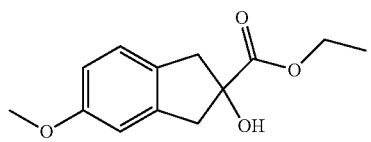 [SMILES: CCOC(=O)C1(O)Cc2ccc(OC)cc2C1]

To a solution of 2-hydroxy-5-methoxy-2,3-dihydro-1H-indene-2-carboxylic acid (2.32 g, 11.1 mmol) in ethanol (37.1 ml) was added a catalytic amount of sulfuric acid. The reaction mixture was stirred for 15 h at room temperature. The solvent was evaporated in vacuo. The residue was partitioned between ethyl acetate (50 ml) and 1 M sodium carbonate (50 ml). The layers were separated. The aqueous layer was extracted with three 50-ml portion of ethyl acetate. The combined organic layers were washed with one 30-ml portion of brine, dried over anhydrous sodium sulfate, filtered and concentrated in vacuo. Flash chromatography with n-heptane/ethyl acetate as eluent gave the title compound (1.57 g, 60%) a light yellow viscous oil. MS m/e: 237 ([M+H]+).

Alpha-hydroxy Ester 3

Methyl 2-hydroxy-5-methyl-2,3-dihydro-1H-indene-2-carboxylate

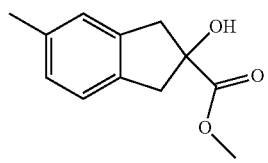

The title compound was obtained as brown oil in 45% yield according to the general procedure XVII from 5-methyl-2-[(trimethylsilyl)oxy]-2,3-dihydro-1H-indene-2-carbonitrile.

Alpha-hydroxy Ester 4

Ethyl 2-hydroxy-5,6-dimethyl-2,3-dihydro-1H-indene-2-carboxylate

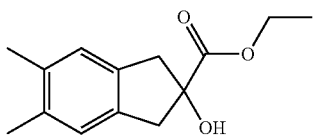 [SMILES: CCOC(=O)C1(O)Cc2cc(C)c(C)cc2C1]

The title compound was obtained as yellow oil in 30% yield according to the general procedure XIX from ethyl 5,6-dimethyl-2,3-dihydro-1H-indene-2-carboxylate.

Alpha-hydroxy Ester 5

Methyl 5,6-difluoro-2-hydroxy-2,3-dihydro-1H-indene-2-carboxylate

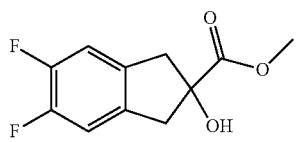 [SMILES: COC(=O)C1(O)Cc2cc(F)c(F)cc2C1]

The title compound was obtained as light brown solid in 46% yield according to the general procedure XVII from 5,6-difluoro-2-[(trimethylsilyl)oxy]-2,3-dihydro-1H-indene-2-carbonitrile.

Alpha-hydroxy Ester 6

Methyl 2-hydroxy-5,6-dimethoxy-2,3-dihydro-1H-indene-2-carboxylate

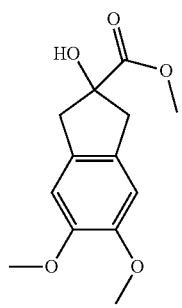

The title compound was obtained as orange solid in 35% yield according to the general procedure XVIII from 5,6-dimethoxy-2-(trimethylsilyloxy)-2,3-dihydro-1H-indene-2-carboxylate.

Alpha-hydroxy Ester 7

Methyl 1-hydroxy-2,3-dihydro-1H-indene-1-carboxylate

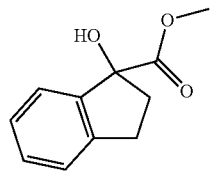

The title compound was obtained as brown oil in 91% yield according to the general procedures XVIII from 1-(trimethylsilyloxy)-2,3-dihydro-1H-indene-1-carbonitrile. MS m/e: 193 ([M+H]$^+$).

Alpha-hydroxy Ester 8

Methyl 2-hydroxy-1,2,3,4-tetrahydronaphthalene-2-carboxylate

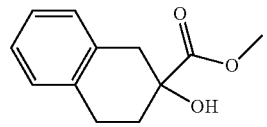

The title compound was obtained as colorless oil in 84% yield according to the general procedure XVIII from 2-hydroxy-1,2,3,4-tetrahydronaphthalene-2-carbonitrile.

Alpha-hydroxy Ester 9

Methyl 1-hydroxy-1,2,3,4-tetrahydronaphthalene-1-carboxylate

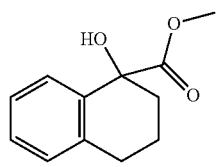

The title compound was obtained as yellow oil in 87% yield according to the general procedure XVIII from 1-(trimethylsilyloxy)-1,2,3,4-tetrahydronaphthalene-1-carbonitrile.

Alpha-hydroxy Ester 10

Ethyl 4-chloro-2-hydroxy-7-methoxy-2,3-dihydro-1H-indene-2-carboxylate

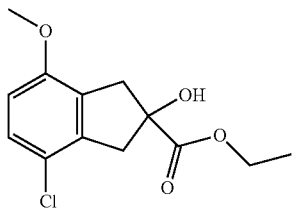 [SMILES: CCOC(=O)C1(O)Cc2c(Cl)ccc(OC)c2C1]

To a solution of 4-chloro-7-methoxy-2-(trimethyl silyloxy)-2,3-dihydro-1H-indene-2-carbonitrile (1.01 g, 3.41 mmol) in toluene (6.9 ml) was added hydrochloric acid, 25% in water (2.22 ml, 17.1 mmol) at 90° C. The reaction mixture was stirred for 15 h. The heating bath was removed, and stirring was continued for 2 h. The reaction mixture was partitioned between ethyl acetate (50 ml) and brine (20 ml). The layers were separated. The aqueous layer was extracted with two 50-ml portions of ethyl acetate. The combined organic layers were washed with one 20-ml portion of brine, dried over anhydrous sodium sulfate, filtered and concentrated in vacuo to give the crude alpha-hydroxy acid intermediate (1.3 g, dark brown). A mixture of the alpha-hydroxy acid intermediate in ethanol (14 ml) and a catalytic amount of sulfuric acid was stirred at room temperature for 6 h. The solvent was evaporated in vacuo. The residue was partitioned between ethyl acetate (50 ml) and 1 M aqueous sodium bicarbonate solution (50 ml). The layers were separated. The aqueous layer was extracted with two 50-ml portion of ethyl acetate. The combined organic layers were washed with one 30-ml portion of brine, dried over anhydrous sodium sulfate and concentrated in vacuo. Purification by flash-chromatography with n-heptane/ethyl acetate as eluent gave the title compound (0.169 g, 18%) as brown viscous oil. MS m/e: 270 ([M]⁺).

Alpha-hydroxy Ester 11

Ethyl 2-hydroxy-7-methoxy-2,3-dihydro-1H-indene-2-carboxylate

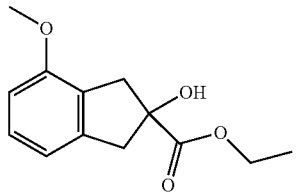 [SMILES: CCOC(=O)C1(O)Cc2cccc(OC)c2C1]

A 50-ml two-necked round-bottomed flask was charged with ethyl 4-chloro-2-hydroxy-7-methoxy-2,3-dihydro-1H-indene-2-carboxylate (0.169 g, 0.624 mmol) and ethanol (6.2 ml). The flask was evacuated to approximately 110 mbar until the solvent began to bubble gently and back-filled with Argon after 10 s. This procedure was repeated twice. After addition of palladium, 10% on activated charcoal (133 mg, 125 μmol, Eq: 0.2), the flask was evacuated to 110 mbar, back-filled with hydrogen and stirred for 20 h under an atmosphere of 1 bar of hydrogen gas. The catalyst was removed by filtration over Decalite and washed with ethanol. The solvent was evaporated. The residue was partitioned between ethyl acetate (50 ml) and water/brine (1:1) (30 ml). The layers were separated. The aqueous layer was extracted with two 50-ml portions of ethyl acetate. The combined organic layers were washed with one 20-ml portion of brine, dried over anhydrous sodium sulfate, filtered and concentrated in vacuo to give the title compound (0.147 g, quantitative) as light brown viscous oil. MS m/e: 236 ([M]⁺).

2-Amino-oxazol-4-one intermediates of formula (III)

General Procedure XX:

A mixture of molecular sieves 4A, guanidine hydrochloride (1.6-7 eq) and potassium tert-butoxide in tert-butanol is stirred at room temperature for 2-24 h. Addition of an alpha-hydroxy ester intermediate of formula (XII) is followed by stirring for 2-24 h. The reaction mixture is diluted with a solvent mixture such as ethyl acetate/2-propanol (4:1) or isopropyl acetate/2-propanol (4:1). The solids are removed by filtration. The filtrate is washed with water. The layers are separated. The aqueous layer is extracted with one or two portions of organic solvent mixture. The combined organic layers are washed with one portion of brine, dried over anhydrous sodium sulfate, filtered and concentrated to dryness. Trituration from a solvent such as ethyl acetate or isopropyl acetate gives a 2-amino-oxazol-4-one intermediate of formula (III).

2-Amino-oxazol-4-one intermediate 1

2'-Amino-1,3-dihydro-4'H-spiro[indene-2,5'-[1,3]oxazol]-4'-one

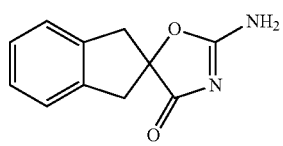 [SMILES: NC1=NC(=O)C2(Cc3ccccc3C2)O1]

The title compound was obtained as white solid in 75% yield according to the general procedure XX from ethyl 2-hydroxy-2,3-dihydro-1H-indene-2-carboxylate. MS m/e: 203 ([M+H]⁺).

2-Amino-oxazol-4-one intermediate 2

2'-Amino-5-methyl-1,3-dihydro-4'H-spiro[indene-2,5'-[1,3]oxazol]-4'-one

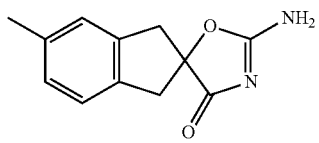 [SMILES: Cc1ccc2c(c1)CC1(C2)OC(N)=NC1=O]

The title compound was obtained as light brown solid in 86% yield according to the general procedure XX from ethyl 2-hydroxy-5-methyl-2,3-dihydro-1H-indene-2-carboxylate. MS m/e: 217 ([M+H]⁺).

2-Amino-oxazol-4-one intermediate 3

2'-Amino-5,6-dimethyl-1,3-dihydro-4'H-spiro[indene-2,5'-oxazol]-4'-one

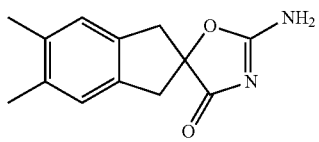 [SMILES: Cc1cc2c(cc1C)CC1(C2)OC(N)=NC1=O]

The title compound was obtained off-white solid in quantitative yield according to the general procedure XX from ethyl 2-hydroxy-5,6-dimethyl-2,3-dihydro-1H-indene-2-carboxylate. MS m/e: 231 ([M+H]⁺).

2-Amino-oxazol-4-one intermediate 4

2'-Amino-5,6-difluoro-1,3-dihydro-4'H-spiro[indene-2,5'-[1,3]oxazol]-4'-one

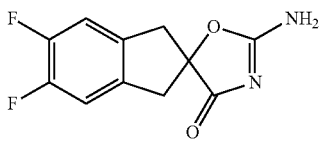 [SMILES: NC1=NC(=O)C2(Cc3cc(F)c(F)cc3C2)O1]

The title compound was obtained white solid in 73% yield according to the general procedure XX from ethyl 2-hydroxy-5,6-dimethyl-2,3-dihydro-1H-indene-2-carboxylate. MS m/e: 239 ([M+H]$^+$).

2-Amino-oxazol-4-one intermediate 5

2'-Amino-5-methoxy-1,3-dihydro-4'H-spiro[indene-2,5'-[1,3]oxazol]-4'-one

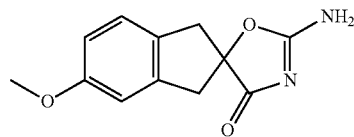 [SMILES: COc1ccc2c(c1)CC1(C2)OC(N)=NC1=O]

The title compound was obtained white solid in 68% yield according to the general procedure XX from ethyl 2-hydroxy-5-methoxy-2,3-dihydro-1H-indene-2-carboxylate. MS m/e: 233 ([M+H]$^+$).

2-Amino-oxazol-4-one intermediate 6

2'-Amino-5,6-dimethoxy-1,3-dihydro-4'H-spiro[indene-2,5'-oxazol]-4'-one

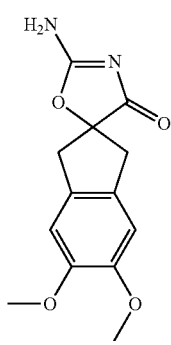 [SMILES: COc1cc2c(cc1OC)CC1(C2)OC(N)=NC1=O]

The title compound was obtained as light brown solid in 35% yield according to the general procedure XX from methyl 2-hydroxy-5,6-dimethoxy-2,3-dihydro-1H-indene-2-carboxylate. MS m/e: 264 ([M+H]$^+$).

2-Amino-oxazol-4-one intermediate 7

2'-Amino-2,3-dihydro-4'H-spiro[indene-1,5'-[1,3]oxazol]-4'-one

The title compound was obtained as brown solid in 85% yield according to the general procedure XX from methyl 1-hydroxy-2,3-dihydro-1H-indene-1-carboxylate. MS m/e: 203 ([M+H]$^+$).

2-Amino-oxazol-4-one intermediate 8

2'-Amino-3,4-dihydro-1H,4'H-spiro[naphthalene-2,5'-[1,3]oxazol]-4'-one

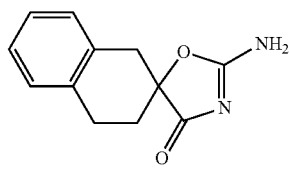 [SMILES: NC1=NC(=O)C2(CCc3ccccc3C2)O1]

The title compound was obtained as off-white solid in 71% yield according to the general procedure XX from methyl 2-hydroxy-1,2,3,4-tetrahydronaphthalene-2-carboxylate.

2-Amino-oxazol-4-one intermediate 9

2'-Amino-3,4-dihydro-2H,4'H-spiro[naphthalene-1,5'-[1,3]oxazol]-4'-one

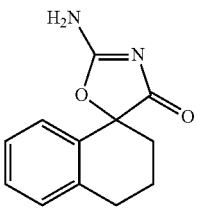 [SMILES: NC1=NC(=O)C2(CCCc3ccccc32)O1]

The title compound was obtained as off-white solid in 61% yield according to the general procedure XX from methyl 1-hydroxy-1,2,3,4-tetrahydronaphthalene-1-carboxylate. MS m/e: 217 ([M+H]$^+$).

2-Amino-oxazol-4-one intermediate 10

2'-Amino-4-methoxy-1,3-dihydro-4'H-spiro[indene-2,5'-oxazol]-4'-one

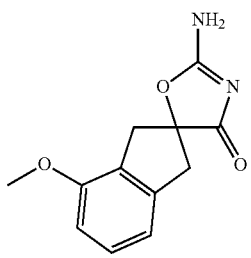 [SMILES: COc1cccc2c1CC1(C2)OC(N)=NC1=O]

The title compound was obtained as off-white solid in 69% yield according to the general procedure XX from ethyl 2-hydroxy-4-methoxy-2,3-dihydro-1H-indene-2-carboxylate. MS m/e: 233 ([M+H]$^+$).

Intermediate of Formula (V)

2-(1'H,3H-Spiro[2-benzofuran-1,4'-piperidin]-1'-yl)-1,3-oxazol-4(5H)-one

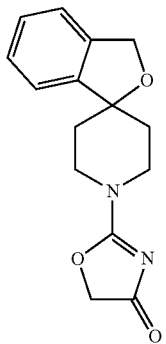 [SMILES: O=C1COC(N2CCC3(CC2)OCc2ccccc23)=N1]

To a solution of 3H-spiro[isobenzofuran-1,4'-piperidine] (7.9 g, 42 mmol) in dichloromethane (250 ml), 2-chloroacetyl isocyanate (5.0 g, 41.8 mmol) was added at RT. The mixture was stirred at 22° C. for 1 h. The reaction progress was monitored by LC/MS. The reaction mixture was poured into 250 ml water and extracted with dichloromethane (2×200 ml). The organic layers were dried over anhydrous sodium sulfate, filtered and concentrated in vacuo. The residue was dissolved with tetrahydrofuran (500 ml) to give a colorless solution. 1,8-Diazabicyclo[5.4.0]undec-7-ene (13 ml, 83 mmol) was added. The reaction mixture was stirred at RT for 30 minutes. The reaction mixture was poured into 400 ml aqueous 1 M hydrogen chloride and extracted with ethyl acetate (1×500 ml) and dichloromethane (2×300 ml). The organic layers were dried over anhydrous sodium sulfate, filtered and concentrated in vacuo. The light yellow solid crude was purified by precipitation from dichloromethane with ethyl acetate yielding the title compound (5.7 g, 50% yield) as a white solid. MS m/e: 273 ([M+H]$^+$).

Intermediate of Formula (VIII)

5,5-Di(prop-2-ynyl)-2-(3H-spiro[isobenzofuran-1,4'-piperidine]-1'-yl)oxazol-4(5H)-one

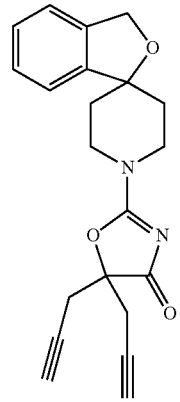 [SMILES: C#CCC1(CC#C)OC(N2CCC3(CC2)OCc2ccccc23)=NC1=O]

To a solution of 2-(3H-spiro[isobenzofuran-1,4'-piperidine]-1'-yl)oxazol-4(5H)-one (4.0 g, 15 mmol, 1.0 eq) in tetrahydrofuran (107 ml) was added lithium bis(trimethylsilyl)amide (29 ml, 29 mmol, 2.0 eq) at −78° C. The mixture was allowed to warm at −30° C. After 30 minutes 3-bromoprop-1-yne (4.9 ml, 44 mmol, 3.0 eq) was added at −78° C. The cooling bath was removed and the mixture was allowed to warm to room temperature. The reaction mixture was poured into 25 ml 1 M aqueous hydrogen chloride solution and extracted with three 25-ml portions of dichloromethane. The combined organic layers were dried over magnesium sulfate, filtered and concentrated in vacuo. Purification by flash-chromatography with n-heptane/ethyl acetate as eluent gave the title compound (2.7 g, 52%) as yellow solid. MS m/e: 349 ([M+H]$^+$).

Intermediate of Formula (VII)

5-(Prop-2-ynyl)-2-(3H-spiro[isobenzofuran-1,4'-piperidine]-1'-yl)oxazol-4(5H)-one

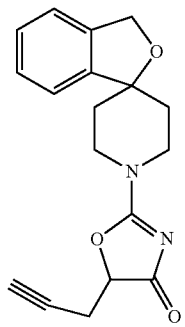 [SMILES: C#CCC1OC(N2CCC3(CC2)OCc2ccccc23)=NC1=O]

In a schlenk-tube, 2-(3H-spiro[isobenzofuran-1,4'-piperidine]-1'-yl)oxazol-4(5H)-one (5.0 g, 18 mmol, 1.0 eq) was dissolved in tetrahydrofuran (183 ml) and lithium bis(trimethylsily)amide (18 ml, 18 mmol, 1.0 eq) was added slowly at −30° C. and stirred for 1 h. The Li-intermediate was added to a solution of 3-bromoprop-1-yne in (5.5 g, 4.1 ml, 37 mmol, 2.0 eq) in tetrahydrofuran (33 ml) at 0-5° C. Stirring was continued for 30 minutes. The reaction mixture was poured into 10 ml 1 M aqueous hydrogen chloride solution and extracted with three 10-ml portions of dichloromethane. The combined organic layers were dried over magnesium sulfate, filtered and concentrated in vacuo. Purification by flash chromatography with n-heptane/ethyl acetate as eluent gave the title compound (1.3 g, 22%) as light brown solid. MS m/e: 311 ([M+H]+).

Intermediate of formula (XI)

2-(4-Oxo-5-(prop-2-ynyl)-2-(3H-spiro[isobenzofuran-1,4'-piperidine]-1'-yl)-4,5-dihydrooxazol-5-yl)acetonitrile

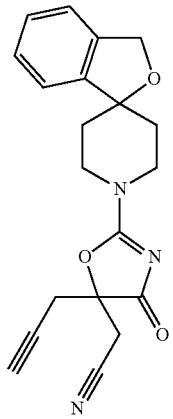 [SMILES: C#CCC1(CC#N)OC(N2CCC3(CC2)OCc2ccccc23)=NC1=O]

To a solution of 5-(prop-2-ynyl)-2-(3H-spiro[isobenzofuran-1,4'-piperidine]-1'-yl)oxazol-4(5H)-one (0.10 g, 0.32 mmol, 1.0 eq) in tetrahydrofuran (3 ml) was added lithium bis(trimethylsilyl)amide (0.39 ml, 0.39 mmol, 1.2 eq) at −78° C. Stirring was continued for 5 minutes, then 2-bromoacetonitrile (0.034 ml, 0.48 mmol, 1.5 eq) was added. The reaction mixture was allowed to warm to room temperature and was quenched by the addition of 10 ml aqueous saturated ammonium chloride solution and extracted with two 20-ml portions of dichloromethane. The combined organic layers were dried over anhydrous sodium sulfate, filtered and concentrated in vacuo. Purification by flash chromatography with n-heptane/ethyl acetate as eluent gave the title compound (0.042 g, 37%) as light brown solid. MS m/e: 350 ([M+H]+).

EXAMPLES

General procedure XXI: Aminolysis

A mixture of a spiropiperidine of formula (II) as free base and a 2-amino-oxazol-4-one intermediate of formula (III) in a solvent such as ethanol, n-butanol, tert-butanol, 1,4-dioxane or tetrahydrofuran (0.1-0.3 M) is heated at 78-125° C. for 6-72 h. Alternatively a mixture of a spiropiperidine of formula (II) as hydrochloride salt (1-1.5 eq), an organic base such as Huenig's Base or triethylamine (1-1.5 eq) and a 2-amino-oxazol-4-one intermediate of formula (III) in a solvent such as ethanol, n-butanol, tert-butanol, 1,4-dioxane or tetrahydrofuran (0.1-0.3 M) is heated at 78-125° C. for 6-72 h. The mixture can alternatively be heated under microwave irradiation at 130-160° C. for 10-30 minutes. After cooling to room temperature the reaction mixture is partitioned between an organic solvent such as ethyl acetate or dichloromethane and aqueous saturated ammonium chloride solution. The layers are separated. The aqueous layer is extracted with one or two portions of organic solvent. The combined organic layers are washed with one portion of brine, dried over anhydrous sodium sulfate, filtered and concentrated to dryness. Purification by flash-chromatography or crystallization from a suitable solvent gives a compound of formula (I).

General Procedure XXII: Ruthenium Catalyzed 2+2+2 Cyclization

To a solution of a compound of formula (VII) in 1,2-dichloroethane (0.2 M) is added an alkyne intermediate of formula (IX) (1.5 eq) at room temperature. Chloro(pentamethylcyclopentadienyl)(cyclooctadiene)ruthenium(II) (0.03 eq) is added as a solution in 1,2-dichloroethane. The reaction mixture is stirred for 20-60 minutes and consecutively concentrated to dryness. Purification by flash-chromatography gives a compound of formula (I).

General Procedure XXIII: Cobalt Catalyzed 2+2+2 Cyclization

A solution of a compound of formula (XI) in toluene (0.04 M) and cyclopentadienecobalt dicarbonyl (0.3 eq) is purged with ethyne three times and positive pressure is maintained at 1.5 bar. The vessel is placed in front of a 300 W tungsten lamp (approximately 5 cm) and irradiated for 1 h. During the reaction, the temperature rises to approximately 80° C. and the pressure increases to 2.5 bar. The reaction mixture is concentrated to dryness. Purification by flash-chromatography gives a compound of formula (I).

Example 1

2'-(1'H,3H-Spiro[2-benzofuran-1,4'-piperidin]-1'-yl)-1,3-dihydro-4'H-spiro[indene-2,5'-[1,3]oxazol]-4'-one The title compound was obtained as white foam in 28% yield from 2'-amino-1,3-dihydro-4'H-spiro[indene-2,5'-[1,3]oxazol]-4'-one and 3H-spiro[isobenzofuran-1,4'-piperidine] according to the general procedure XXI. MS m/e: 375 ([M+H]+).

Example 2

1'-(4'-Oxo-1,3-dihydro-4'H-spiro[indene-2,5'-[1,3]oxazol]-2'-yl)-3H-spiro[2-benzofuran-1,4'-piperidin]-3-one The title compound was obtained as light-brown solid in 44% yield from 2'-amino-1,3-dihydro-4'H-spiro[indene-2,5'-[1,3]oxazol]-4'-one and 3H-spiro[isobenzofuran-1,4'-piperidin]-3-one according to the general procedure XXI. MS m/e: 390 ([M+H]+).

Example 3

2'-(3,3-Dimethyl-1'H,3H-spiro[2-benzofuran-1,4'-piperidin]-1'-yl)-1,3-dihydro-4'H-spiro[indene-2,5'-[1,3]oxazol]-4'-one The title compound was obtained as light-brown solid in 23% yield from 2'-amino-1,3-dihydro-4'H-spiro[indene-2,5'-[1,3]oxazol]-4'-one and 3,3-dimethyl-3H-spiro[isobenzofuran-1,4'-piperidine] according to the general procedure XXI. MS m/e: 403 ([M+H]+).

Example 4

2'-(4-Methyl-1'H,3H-spiro[2-benzofuran-1,4'-piperidin]-1'-yl)-1,3-dihydro-4'H-spiro[indene-2,5'-[1,3]oxazol]-4'-one

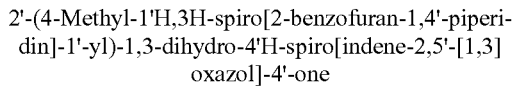

The title compound was obtained as light brown solid in 52% yield from 2'-amino-1,3-dihydro-4'H-spiro[indene-2,5'-[1,3]oxazol]-4'-one and 4-methyl-3H-spiro[isobenzofuran-1,4'-piperidine] according to the general procedure XXI. MS m/e: 389.5 ([M+H]$^+$).

Example 5

4-Methyl-1'-(4'-oxo-1,3-dihydro-4'H-spiro[indene-2,5'-[1,3]oxazol]-2'-yl)-3H-spiro[2-benzofuran-1,4'-piperidin]-3-one

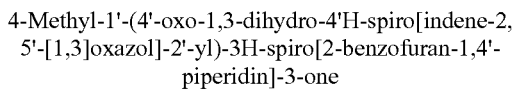

The title compound was obtained as light brown solid in 55% yield from 2'-amino-1,3-dihydro-4'H-spiro[indene-2,5'-[1,3]oxazol]-4'-one and 4-methyl-3H-spiro[isobenzofuran-1,4'-piperidin]-3-one according to the general procedure XXI. MS m/e: 403 ([M+H]$^+$).

Example 6

5-Methyl-1'-(4'-oxo-1,3-dihydro-4'H-spiro[indene-2,5'-[1,3]oxazol]-2'-yl)-3H-spiro[2-benzofuran-1,4'-piperidin]-3-one

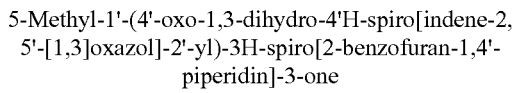

In a 5 ml pear-shaped flask, 5-bromo-1'-(4'-oxo-1,3-dihydro-4'H-spiro[indene-2,5'-[1,3]oxazol]-2'-yl)-3H-spiro[2-benzofuran-1,4'-piperidin]-3-one (50 mg, 1.0 eq) and tetrakis(triphenylphosphine)palladium (0) (6.2 mg, 0.050 eq) were combined with tetrahydrofuran (1 ml) to give a brown suspension. Dimethylzinc, 2 M in toluene (0.054 ml, 1.0 eq) was added. The reaction mixture was heated to 70° C. and stirred for 4 h. The reaction mixture was poured into 2 ml 5% sodium carbonate solution and extracted with ethyl acetate (3×5 ml). The organic layers were dried over anhydrous sodium sulfate, filtered and concentrated in vacuo. The crude material was purified by flash chromatography yielding the title compound in 65% yield as off white solid. MS m/e: 403 ([M+H]$^+$).

Example 7

6-Methyl-1'-(4'-oxo-1,3-dihydro-4'H-spiro[indene-2,5'-[1,3]oxazol]-2'-yl)-3H-spiro[2-benzofuran-1,4'-piperidin]-3-one

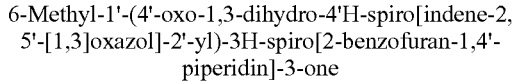

In a 5 ml microwave vial, 6-chloro-1'-(4'-oxo-1,3-dihydro-4'H-spiro[indene-2,5'-[1,3]oxazol]-2'-yl)-3H-spiro[2-benzofuran-1,4'-piperidin]-3-one (50 mg, 1.0 eq) and methylboronic acid (11 mg, 1.5 eq) were combined with toluene (0.5 ml) to give a brown suspension. Palladium (II) acetate (0.53 mg, 0.02 eq), potassium phosphate monohydrate (55 mg, 2.0 eq) and dicyclohexyl(2',6'-dimethoxybiphenyl-2-yl)phosphine (1.9 mg, 0.04 eq) were added. The reaction mixture was heated to 90° C. and stirred for 4 h. The reaction mixture was poured into 2 ml 5% sodium carbonate solution and extracted with ethyl acetate (3×5 ml). The organic layers were dried over anhydrous sodium sulfate, filtered and concentrated in vacuo. The crude material was purified by flash chromatography yielding the title compound in 8% yield. MS m/e: 403 ([M+H]$^+$).

Example 8

5-Methoxy-1'-(4'-oxo-1,3-dihydro-4'H-spiro[indene-2,5'-[1,3]oxazol]-2'-yl)-3H-spiro[2-benzofuran-1,4'-piperidin]-3-one

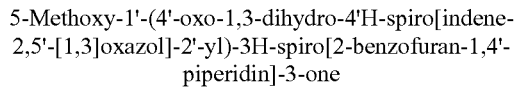

The title compound was obtained as white solid in 25% yield from 2'-amino-1,3-dihydro-4'H-spiro[indene-2,5'-[1,3]oxazol]-4'-one and 5-methoxy-3H-spiro[isobenzofuran-1,4'-piperidin]-3-one according to the general procedure XXI. MS m/e: 419 ([M+H]$^+$).

Example 9

5-Hydroxy-1'-(4'-oxo-1,3-dihydro-4'H-spiro[indene-2,5'-[1,3]oxazol]-2'-yl)-3H-spiro[2-benzofuran-1,4'-piperidin]-3-one

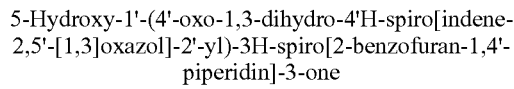

To a solution of 5-methoxy-1'-(4'-oxo-1,3-dihydro-4'H-spiro[indene-2,5'-[1,3]oxazol]-2'-yl)-3H-spiro[2-benzofuran-1,4'-piperidin]-3-one (0.013 g, 0.031 mmol) in dichloromethane (2.0 ml) was added boron tribromide, 1 M in dichloromethane (0.093 ml, 0.093 mmol) at −78° C. The reaction mixture was stirred for 1 h. The dry ice/acetone bath was removed and stirring was continued for 30 minutes. Further boron tribromide, 1 M in dichloromethane (0.093 ml, 0.093 mmol) was added at 0-5° C. The reaction mixture was stirred for 30 minutes. The ice bath was removed and stirring was continued for 15 h. The reaction mixture was quenched with ice water and partitioned between dichloromethane (30 ml) and saturated aqueous bicarbonate solution (10 ml). The layers were separated. The aqueous layer was extracted with three 10-ml portions of dichloromethane. The combined organic layers were washed with one 5-ml portion of brine, dried over anhydrous sodium sulfate, filtered and concentrated in vacuo. Purification by preparative RP-HPLC on a Gemini NX 3u 50×4.6 mm column with methanol/water as eluent gave the title compound (0.005 g, 40%) as off-white solid. MS m/e: 405 ([M+H]$^+$).

Example 10

6-Methoxy-1'-(4'-oxo-1,3-dihydro-4'H-spiro[indene-2,5'-[1,3]oxazol]-2'-yl)-3H-spiro[2-benzofuran-1,4'-piperidin]-3-one

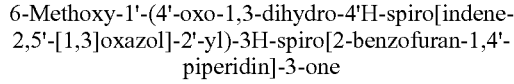

The title compound was obtained as off-white solid in 74% yield from 2'-amino-1,3-dihydro-4'H-spiro[indene-2,5'-[1,3]oxazol]-4'-one and 6-methoxy-3H-spiro[isobenzofuran-1,4'-piperidin]-3-one according to the general procedure XXI. MS m/e: 419 ([M+H]$^+$).

Example 11

6-Hydroxy-1'-(4'-oxo-1,3-dihydro-4'H-spiro[indene-2,5'-[1,3]oxazol]-2'-yl)-3H-spiro[2-benzofuran-1,4'-piperidin]-3-one

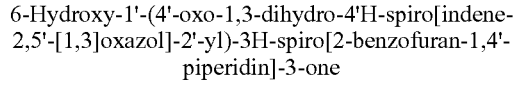

To a suspension of 6-methoxy-1'-(4'-oxo-1,3-dihydro-4'H-spiro[indene-2,5'-[1,3]oxazol]-2'-yl)-3H-spiro[2-benzofuran-1,4'-piperidin]-3-one (60 mg, 1.0 eq) in dichloromethane (0.72 ml) at 0-5° C., was added 1 M boron tribromide solution in dichloromethane (0.43 ml, 3.0 eq). The mixture was stirred at 0-5° C. for 2 h, then at 22° C. for 18 h. The reaction mixture was quenched with water and stirred for 15 minutes, then dichloromethane was added. The phases were separated. The aqueous layer was extracted with dichloromethane (2×5 ml). The combined organic layers were washed with brine, dried over anhydrous sodium sulfate, filtered and concentrated in vacuo. The title compound was obtained after purification by flash chromatography in 26% yield as a white solid. MS m/e: 406 ([M+H]$^+$).

Example 12

5,6-Dimethoxy-1'-(4'-oxo-1,3-dihydro-4'H-spiro[indene-2,5'-[1,3]oxazol]-2'-yl)-3H-spiro[2-benzofuran-1,4'-piperidin]-3-one The title compound was obtained as white solid in 53% yield from 2'-amino-1,3-dihydro-4'H-spiro[indene-2,5'-[1,3]oxazol]-4'-one and 5,6-dimethoxy-3H-spiro[isobenzofuran-1,4'-piperidin]-3-one according to the general procedure XXI. MS m/e: 449 ([M+H]$^+$).

Example 13

5,6-Dihydroxy-1'-(4'-oxo-1,3-dihydro-4'H-spiro[indene-2,5'-[1,3]oxazol]-2'-yl)-3H-spiro[2-benzofuran-1,4'-piperidin]-3-one To a solution of 5,6-dimethoxy-1'-(4'-oxo-1,3-dihydro-4'H-spiro[indene-2,5'-[1,3]oxazol]-2'-yl)-3H-spiro[2-benzofuran-1,4'-piperidin]-3-one (0.22 g, 0.48 mmol) in dichloromethane (2.4 ml) was added 1 M boron tribromide solution in dichloromethane (1.4 ml, 1.4 mmol) at 0-5° C. The reaction mixture was stirred for 10 minutes at 0-5° C. The ice bath was removed and stirring was continued at room temperature for 3 h. The reaction mixture was quenched with ice/water at 0-5° C. and stirred for 5 minutes. The solvent was evaporated. The residue was partitioned between ethyl acetate (50 ml) and water (10 ml). The layers were separated. The aqueous layer was extracted with three 50-ml portions of ethyl acetate. The combined organic layers were dried over anhydrous sodium sulfate, filtered and concentrated in vacuo. Purification by preparative RP-HPLC on a Gemini NX 3u 50×4.6 mm column with methanol/water as eluent gave the title compound (0.007 g, 3%) as red solid. MS m/e: 421 ([M+H]$^+$).

Example 14

4-Fluoro-1'-(4'-oxo-1,3-dihydro-4'H-spiro[indene-2,5'-[1,3]oxazol]-2'-yl)-3H-spiro[2-benzofuran-1,4'-piperidin]-3-one The title compound was obtained as white gum in 19% yield from 2'-amino-1,3-dihydro-4'H-spiro[indene-2,5'-[1,3]oxazol]-4'-one and 4-fluoro-3H-spiro[isobenzofuran-1,4'-piperidin]-3-one according to the general procedure XXI. MS m/e: 407 ([M+H]$^+$).

Example 15

5-Fluoro-1'-(4'-oxo-1,3-dihydro-4'H-spiro[indene-2,5'-[1,3]oxazol]-2'-yl)-3H-spiro[2-benzofuran-1,4'-piperidin]-3-one The title compound was obtained as white solid in 17% yield from 2'-amino-1,3-dihydro-4'H-spiro[indene-2,5'-[1,3]oxazol]-4'-one and 5-fluoro-3H-spiro[isobenzofuran-1,4'-piperidin]-3-one according to the general procedure XXI. MS m/e: 407 ([M+H]$^+$).

Example 16

7-Fluoro-1'-(4'-oxo-1,3-dihydro-4'H-spiro[indene-2,5'-[1,3]oxazol]-2'-yl)-3H-spiro[2-benzofuran-1,4'-piperidin]-3-one The title compound was obtained as off-white solid in 51% yield from 2'-amino-1,3-dihydro-4'H-spiro[indene-2,5'-[1,3]oxazol]-4'-one and 7-fluoro-3H-spiro[isobenzofuran-1,4'-piperidin]-3-one according to the general procedure XXI. MS m/e: 407 ([M+H]$^+$).

Example 17

6-Chloro-1'-(4'-oxo-1,3-dihydro-4'H-spiro[indene-2,5'-[1,3]oxazol]-2'-yl)-3H-spiro[2-benzofuran-1,4'-piperidin]-3-one The title compound was obtained as brown foam in 47% yield from 2'-amino-1,3-dihydro-4'H-spiro[indene-2,5'-[1,3]oxazol]-4'-one and 6-chloro-3H-spiro[isobenzofuran-1,4'-piperidin]-3-one according to the general procedure XXI. MS m/e: 423 ([M+H]$^+$).

Example 18

5-Bromo-1'-(4'-oxo-1,3-dihydro-4'H-spiro[indene-2,5'-[1,3]oxazol]-2'-yl)-3H-spiro[2-benzofuran-1,4'-piperidin]-3-one The title compound was obtained as light brown foam in 20% yield from 2'-amino-1,3-dihydro-4'H-spiro[indene-2,5'-[1,3]oxazol]-4'-one and 5-bromo-3H-spiro[isobenzofuran-1,4'-piperidin]-3-one according to the general procedure XXI. MS m/e: 469 ([M+H]$^+$).

Example 19

(−)-2'-(1'H,3H-Spiro[2-benzofuran-1,4'-piperidin]-1'-yl)-2,3-dihydro-4'H-spiro[indene-1,5'-[1,3]oxazol]-4'-one and Example 20

(+)-2'-(1'H,3H-Spiro[2-benzofuran-1,4'-piperidin]-1'-yl)-2,3-dihydro-4'H-spiro[indene-1,5'-[1,3]oxazol]-4'-one The title compounds were obtained according to the general procedure XXI from 2'-amino-2,3-dihydro-4'H-spiro[indene-1,5'-[1,3]oxazol]-4'-one and 3H-spiro[isobenzofuran-1,4'-piperidine] following chiral HPLC separation on a Chiralpak AD column with n-heptane/ethanol as eluent. The compounds are cited in the order of elution:

(−)-2'-(1'H,3H-spiro[2-benzofuran-1,4'-piperidin]-1'-yl)-2,3-dihydro-4'H-spiro[indene-1,5'-[1,3]oxazol]-4'-one: off-white solid, 7% yield. MS m/e: 375 ([M+H]$^+$).

(+)-2'-(1'H,3H-spiro[2-benzofuran-1,4'-piperidin]-1'-yl)-2,3-dihydro-4'H-spiro[indene-1,5'-[1,3]oxazol]-4'-one: light yellow solid, 8% yield. MS m/e: 375 ([M+H]$^+$).

Example 21

5-Methyl-2'-(1'H,3H-spiro[2-benzofuran-1,4'-piperidin]-1'-yl)-1,3-dihydro-4'H-spiro[indene-2,5'-[1,3]oxazol]-4'-one The title compound was obtained as off-white solid in 62% yield from 2'-amino-5-methyl-1,3-dihydro-4'H-spiro

139

[indene-2,5'-oxazol]-4'-one and 3H-spiro[isobenzofuran-1,4'-piperidine] according to the general procedure XXI. MS m/e: 389 ([M+H]$^+$).

Example 22

1'-(5-Methyl-4'-oxo-1,3-dihydro-4'H-spiro[indene-2,5'-[1,3]oxazol]-2'-yl)-3H-spiro[2-benzofuran-1,4'-piperidin]-3-one The title compound was obtained as off-white solid in 74% yield from 2'-amino-5-methyl-1,3-dihydro-4'H-spiro[indene-2,5'-oxazol]-4'-one and 3H-spiro[isobenzofuran-1,4'-piperidin]-3-one hydrochloride using triethylamine according to the general procedure XXI. MS m/e: 403 ([M+H]$^+$).

Example 23

(+)-1'-[5-Methyl-4'-oxo-1,3-dihydro-4'H-spiro[indene-2,5'-[1,3]oxazol]-2'-yl]-3H-spiro[2-benzofuran-1,4'-piperidin]-3-one and Example 24

(−)-1'-[5-Methyl-4'-oxo-1,3-dihydro-4'H-spiro[indene-2,5'-[1,3]oxazol]-2'-yl]-3H-spiro[2-benzofuran-1,4'-piperidin]-3-one (+)-1'-[5-methyl-4'-oxo-1,3-dihydro-4'H-spiro[indene-2,5'-[1,3]oxazol]-2'-yl]-3H-spiro[2-benzofuran-1,4'-piperidin]-3-one and (−)-1'-[5-methyl-4'-oxo-1,3-dihydro-4'H-spiro[indene-2,5'-[1,3]oxazol]-2'-yl]-3H-spiro[2-benzofuran-1,4'-piperidin]-3-one were obtained from 1'-(5-methyl-4'-oxo-1,3-dihydro-4'H-spiro[indene-2,5'-[1,3]oxazol]-2'-yl)-3H-spiro[2-benzofuran-1,4'-piperidin]-3-one by chiral HPLC separation on Lux Amylose column with n-heptane/ethanol as eluent.

(+)-1'-[5-methyl-4'-oxo-1,3-dihydro-4'H-spiro[indene-2,5'-[1,3]oxazol]-2'-yl]-3H-spiro[2-benzofuran-1,4'-piperidin]-3-one (0.050 g, 27%) was obtained as white solid. MS m/e: 403.5 ([M+H]$^+$). [α]D=+23.10 (c=1.000, CHCl$_3$, 20° C.).

(−)-1'-[5-methyl-4'-oxo-1,3-dihydro-4'H-spiro[indene-2,5'-[1,3]oxazol]-2'-yl]-3H-spiro[2-benzofuran-1,4'-piperidin]-3-one (0.049 g, 26%) was obtained as white solid. MS m/e: 403.5 ([M+H]$^+$). [α]D=−21.00 (c=1.000, CHCl$_3$, 20° C.).

Example 25

5,6-Dimethyl-2'-(1'H,3H-spiro[2-benzofuran-1,4'-piperidin]-1'-yl)-1,3-dihydro-4'H-spiro[indene-2,5'-[1,3]oxazol]-4'-one The title compound was obtained as off-white solid in 38% yield from 2'-amino-5,6-dimethyl-1,3-dihydro-4'H-spiro[indene-2,5'-oxazol]-4'-one and 3H-spiro[isobenzofuran-1,4'-piperidine] according to the general procedure XXI. MS m/e: 403 ([M+H]$^+$).

Example 26

1'-(5,6-Dimethyl-4'-oxo-1,3-dihydro-4'H-spiro[indene-2,5'-[1,3]oxazol]-2'-yl)-3H-spiro[2-benzofuran-1,4'-piperidin]-3-one The title compound was obtained as white solid in 12% yield from 2'-amino-5,6-dimethyl-1,3-dihydro-4'H-spiro[indene-2,5'-oxazol]-4'-one and 3H-spiro[isobenzofuran-1,4'-piperidin]-3-one hydrochloride using triethylamine according to the general procedure XXI. MS m/e: 417 ([M+H]$^+$).

Example 27

1'-(5-Methoxy-4'-oxo-1,3-dihydro-4'H-spiro[indene-2,5'-[1,3]oxazol]-2'-yl)-3H-spiro[2-benzofuran-1,4'-piperidin]-3-one The title compound was obtained as white solid in 48% yield from 2'-amino-5-methoxy-1,3-dihydro-4'H-spiro[indene-2,5'-oxazol]-4'-one and 3H-spiro[isobenzofuran-1,4'-piperidin]-3-one according to the general procedure XXI. MS m/e: 419 ([M+H]$^+$).

Example 28

1'-(5-Hydroxy-4'-oxo-1,3-dihydro-4'H-spiro[indene-2,5'-[1,3]oxazol]-2'-yl)-3H-spiro[2-benzofuran-1,4'-piperidin]-3-one To a solution of 1'-(5-methoxy-4'-oxo-1,3-dihydro-4'H-spiro[indene-2,5'-[1,3]oxazol]-2'-yl)-3H-spiro[2-benzofuran-1,4'-piperidin]-3-one (0.27 g, 0.65 mmol) in dichloromethane (6.5 ml) was added 1 M boron tribromide solution in dichloromethane (1.9 ml, 1.9 mmol) at 0-5° C. The ice bath was removed after 5 minutes and stirring was continued for 1 h. The reaction mixture was quenched with methanol (1 ml) at 0-5° C. and stirred for 5 minutes. The reaction mixture was partitioned between ethyl acetate (50 ml) and saturated bicarbonate solution (30 ml). The layers were separated. The aqueous layer was extracted with two 50-ml portions of ethyl acetate. The combined organic layers were washed with one 30-ml portion of brine, dried over anhydrous sodium sulfate, filtered and concentrated in vacuo. The residue was triturated in warm ethyl acetate (6 ml). The precipitate was collected by filtration, washed with ethyl acetate and dried in vacuo to give the title compound (0.23 g, 90%) as off-white solid. MS m/e: 405 ([M+H]$^+$).

Example 29

2'-(1'H,3H-Spiro[2-benzofuran-1,4'-piperidin]-1'-yl)-5-(trimethylsilyl)-1,3-dihydro-4'H-spiro[indene-2,5'-[1,3]oxazol]-4'-one The title compound was obtained as off-white solid in 48% yield from 5,5-di(prop-2-ynyl)-2-(3H-spiro[isobenzofuran-1,4'-piperidine]-1'-yl)oxazol-4(5H)-one and trimethylsilylacetylene using chloro(pentamethylcyclopentadienyl)(cyclooctadiene)ruthenium(II) as a catalyst according to the general procedure XXII. MS m/e: 447 ([M+H]$^+$).

Example 30

5-Fluoro-2'-(1'H,3H-spiro[2-benzofuran-1,4'-piperidin]-1'-yl)-1,3-dihydro-4'H-spiro[indene-2,5'-[1,3]oxazol]-4'-one In a 10 ml round-bottomed flask, 2'-(1'H,3H-spiro[2-benzofuran-1,4'-piperidin]-1'-yl)-5-(trimethylsilyl)-1,3-dihydro-4'H-spiro[indene-2,5'-[1,3]oxazol]-4'-one (30 mg, 1.0 eq) and boron trifluoride diethyl etherate (1.90 g, 200 eq) were combined to give a yellow solution. Mercuric acetate (2.1 mg, 0.1 eq) and lead tetraacetate (36 mg, 1.2 eq) were added and the reaction mixture was stirred at room temperature for 1 h. The reaction mixture was poured into 20 ml aqueous saturated sodium bicarbonate solution and extracted with dichloromethane (4×25 ml). The organic layers were dried over magnesium sulfate, filtered and concentrated in vacuo. The title compound was obtained after flash chromatography as a light brown solid in 80% yield. MS m/e: 393 ([M+H]+).

Example 31

5-Chloro-2'-(1'H,3H-spiro[2-benzofuran-1,4'-piperidin]-1'-yl)-1,3-dihydro-4'H-spiro[indene-2,5'-[1,3]oxazol]-4'-one In a 5 ml round-bottomed flask, 2'-(1'H,3H-spiro[2-benzofuran-1,4'-piperidin]-1'-yl)-5-(trimethylsilyl)-1,3-dihydro-4'H-spiro[indene-2,5'-[1,3]oxazol]-4'-one (45 mg, 1.0 eq) and tert-butyl hypochlorite (16 mg, 1.5 eq) were combined with dichloromethane (1 ml) to give a light yellow solution. The mixture was stirred at room temperature for 5 h and then concentrated in vacuo. The title compound was obtained as colorless oil after purification by HPLC in 18% yield. MS m/e: 410 ([M+H]+).

Example 32

1'-(5,6-Dimethoxy-4'-oxo-1,3-dihydro-4'H-spiro[indene-2,5'-[1,3]oxazol]-2'-yl)-3H-spiro[2-benzofuran-1,4'-piperidin]-3-one The title compound was obtained as white solid in 5% yield from 2'-amino-5,6-dimethoxy-1,3-dihydro-4'H-spiro[indene-2,5'-oxazol]-4'-one and 3H-spiro[isobenzofuran-1,4'-piperidin]-3-one according to the general procedure XXI. MS m/e: 449 ([M+H]+).

Example 33

1'-(5,6-Dihydroxy-4'-oxo-1,3-dihydro-4'H-spiro[indene-2,5'-[1,3]oxazol]-2'-yl)-3H-spiro[2-benzofuran-1,4'-piperidin]-3-one To a suspension of 1'-(5,6-dimethoxy-4'-oxo-1,3-dihydro-4'H-spiro[indene-2,5'-[1,3]oxazol]-2'-yl)-3H-spiro[2-benzofuran-1,4'-piperidin]-3-one (0.064 g, 1.0 eq) in dichloromethane (0.72 ml) at 0-5° C., was added 1 M boron tribromide solution in dichloromethane (0.43 ml, 3.0 eq). The mixture was stirred at 0-5° C. for 2 h. The reaction mixture was quenched with water and stirred for 15 minutes, then dichloromethane was added. The phases were separated. The aqueous layer was extracted with dichloromethane. The combined organic layers were washed with brine, dried over anhydrous sodium sulfate, filtered and concentrated in vacuo. The title compound was obtained by flash chromatography as light brown solid in 13% yield. 421 ([M+H]+).

Example 34

5,6-Difluoro-2'-(1'H,3H-spiro[2-benzofuran-1,4'-piperidin]-1'-yl)-1,3-dihydro-4'H-spiro[indene-2,5'-[1,3]oxazol]-4'-one The title compound was obtained as white solid in 10% yield from 2'-amino-5,6-difluoro-1,3-dihydro-4'H-spiro[indene-2,5'-[1,3]oxazol]-4'-one and 3H-spiro[isobenzofuran-1,4'-piperidine] according to the general procedure XXI. MS m/e: 411 ([M+H]+).

Example 35

1'-(5,6-Difluoro-4'-oxo-1,3-dihydro-4'H-spiro[indene-2,5'-[1,3]oxazol]-2'-yl)-3H-spiro[2-benzofuran-1,4'-piperidin]-3-one The title compound was obtained as white solid in 5% yield from 2'-amino-5,6-difluoro-1,3-dihydro-4'H-spiro[indene-2,5'-[1,3]oxazol]-4'-one and 3H-spiro[isobenzofuran-1,4'-piperidin]-3-one hydrochloride using triethylamine according to the general procedure XXI. MS m/e: 425 ([M+H]+).

Example 36

2'-(1'H,5H-Spiro[furo[3,4-b]pyridine-7,4'-piperidin]-1'-yl)-1,3-dihydro-4'H-spiro[indene-2,5'-[1,3]oxazol]-4'-one The title compound was obtained as colorless oil in 4% yield according to the general procedure XXI from 5H-spiro[furo[3,4-b]pyridine-7,4'-piperidine]hydrochloride, and 2'-amino-1,3-dihydro-4'H-spiro[indene-2,5'-[1,3]oxazol]-4'-one using Huenig's Base. MS m/e: 376.5 ([M+H]+).

Example 37

2'-(1'H,7H-Spiro[furo[3,4-b]pyridine-5,4'-piperidin]-1'-yl)-1,3-dihydro-4'H-spiro[indene-2,5'-[1,3]oxazol]-4'-one The title compound was obtained as white solid in 25% yield according to the general procedure XXI from 7H-spiro[furo[3,4-b]pyridine-5,4'-piperidine] and 2'-amino-1,3-dihydro-4'H-spiro[indene-2,5'-[1,3]oxazol]-4'-one. MS m/e: 376 ([M+H]+).

Example 38

2'-(5,5-Dimethyl-1'H,5H-spiro[furo[3,4-b]pyridine-7,4'-piperidin]-1'-yl)-1,3-dihydro-4'H-spiro[indene-2,5'-[1,3]oxazol]-4'-one The title compound was obtained as white solid in 25% yield from 2'-amino-1,3-dihydro-4'H-spiro[indene-2,5'-[1,3]oxazol]-4'-one and 5,5-dimethyl-5H-spiro[furo[3,4-b]pyridine-7,4'-piperidine] according to the general procedure XXI. MS m/e: 404 ([M+H]+).

Example 39

2'-(7,7-Dimethyl-1'H,7H-spiro[furo[3,4-b]pyridine-5,4'-piperidin]-1'-yl)-1,3-dihydro-4'H-spiro[indene-2,5'-[1,3]oxazol]-4'-one The title compound was obtained as white solid in 23% yield from 2'-amino-1,3-dihydro-4'H-spiro[indene-2,5'-[1,3]oxazol]-4'-one and 7,7-dimethyl-7H-spiro[furo[3,4-b]pyridine-5,4'-piperidine] according to the general procedure XXI. MS m/e: 404 ([M+H]$^+$).

Example 40

2'-(7,7-Dimethyl-1'H,7H-spiro[furo[3,4-b]pyridine-5,4'-piperidin]-1'-yl)-5-methoxy-1,3-dihydro-4'H-spiro[indene-2,5'-[1,3]oxazol]-4'-one The title compound was obtained as light brown solid in 47% yield from 2'-amino-5-methoxy-1,3-dihydro-4'H-spiro[indene-2,5'-oxazol]-4'-one and 7,7-dimethyl-7H-spiro[furo[3,4-b]pyridine-5,4'-piperidine] according to the general procedure XXI. MS m/e: 434 ([M+H]$^+$).

Example 41

2'-(7,7-Dimethyl-1'H,7H-spiro[furo[3,4-b]pyridine-5,4'-piperidin]-1'-yl)-5-hydroxy-1,3-dihydro-4'H-spiro[indene-2,5'-[1,3]oxazol]-4'-one To a solution of 2'-(7,7-dimethyl-1'H,7H-spiro[furo[3,4-b]pyridine-5,4'-piperidin]-1'-yl)-5-methoxy-1,3-dihydro-4'H-spiro[indene-2,5'-[1,3]oxazol]-4'-one (0.27 g, 0.62 mmol) in dichloromethane (6.2 ml) was added 1 M boron tribromide solution in dichloromethane (1.9 ml, 1.9 mmol) at 0-5° C. The ice bath was removed after 5 minutes and stirring was continued for 1 h. The reaction mixture was quenched with methanol (1 ml) at 0-5° C. and stirred for 5 minutes.

The reaction mixture was partitioned between ethyl acetate (50 ml) and saturated bicarbonate solution (30 ml). The layers were separated. The aqueous layer was extracted with two 50-ml portions of ethyl acetate. The combined organic layers were washed with one 30-ml portion of brine, dried over anhydrous sodium sulfate, filtered and concentrated in vacuo. The residue was triturated in warm ethyl acetate (6 ml). The precipitate was collected by filtration, washed with ethyl acetate and dried in vacuo to give the title compound (0.24 g, 93%) as off-white solid. MS m/e: 420 ([M+H]$^+$).

Example 42

2'-(2-Methyl-1'H,5H-spiro[furo[3,4-b]pyridine-7,4'-piperidin]-1'-yl)-1,3-dihydro-4'H-spiro[indene-2,5'-[1,3]oxazol]-4'-one The title compound was obtained as white foam in 49% yield from 2'-amino-1,3-dihydro-4'H-spiro[indene-2,5'-[1,3]oxazol]-4'-one and 2-methyl-5H-spiro[furo[3,4-b]pyridine-7,4'-piperidine] according to the general procedure XXI. MS m/e: 390 ([M+H]$^+$).

Example 43

2-Methyl-1'-(4'-oxo-1,3-dihydro-4'H-spiro[indene-2,5'-[1,3]oxazol]-2'-yl)-5H-spiro[furo[3,4-b]pyridine-7,4'-piperidin]-5-one The title compound was obtained as off-white solid in 46% yield from 2'-amino-1,3-dihydro-4'H-spiro[indene-2,5'-[1,3]oxazol]-4'-one and 2-methyl-5H-spiro[furo[3,4-b]pyridine-7,4'-piperidin]-5-one according to the general procedure XXI. MS m/e: 404 ([M+H]$^+$).

Example 44

2'-(3-Methyl-1'H,5H-spiro[furo[3,4-b]pyridine-7,4'-piperidin]-1'-yl)-1,3-dihydro-4'H-spiro[indene-2,5'-[1,3]oxazol]-4'-one The title compound was obtained as light brown solid in 46% yield from 2'-amino-1,3-dihydro-4'H-spiro[indene-2,5'-[1,3]oxazol]-4'-one and 3-methyl-5H-spiro[furo[3,4-b]pyridine-7,4'-piperidine] according to the general procedure XXI. MS m/e: 390 ([M+H]$^+$).

Example 45

3-Methyl-1'-(4'-oxo-1,3-dihydro-4'H-spiro[indene-2,5'-[1,3]oxazol]-2'-yl)-5H-spiro[furo[3,4-b]pyridine-7,4'-piperidin]-5-one The title compound was obtained as light yellow solid in 28% yield from 2'-amino-1,3-dihydro-4'H-spiro[indene-2,5'-[1,3]oxazol]-4'-one and 3-methyl-5H-spiro[furo[3,4-b]pyridine-7,4'-piperidin]-5-one according to the general procedure XXI. MS m/e: 404 ([M+H]$^+$).

Example 46

2'-(6-Methyl-1H,1'H-spiro[furo[3,4-c]pyridine-3,4'-piperidin]-1'-yl)-1,3-dihydro-4'H-spiro[indene-2,5'-[1,3]oxazol]-4'-one The title compound was obtained as off-white solid in 56% yield from 2'-amino-1,3-dihydro-4'H-spiro[indene-2,5'-[1,3]oxazol]-4'-one and 6-methyl-1H-spiro[furo[3,4-c]pyridine-3,4'-piperidine] according to the general procedure XXI. MS m/e: 391 ([M+H]$^+$).

Example 47

6-Methyl-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one The title compound was obtained as brown solid in 16% yield from 2'-amino-1,3-dihydro-4'H-spiro[indene-2,5'-[1,3]oxazol]-4'-one and 6-methyl-1H-spiro[furo[3,4-c]pyridine-3,4'-piperidin]-1-one according to the general procedure XXI. MS m/e: 405 ([M+H]$^+$).

Example 48

2'-(2-Methyl-1'H,7H-spiro[furo[3,4-b]pyridine-5,4'-piperidin]-1'-yl)-1,3-dihydro-4'H-spiro[indene-2,5'-[1,3]oxazol]-4'-one The title compound was obtained as light brown solid in 41% yield from 2'-amino-1,3-dihydro-4'H-spiro[indene-2,5'-[1,3]oxazol]-4'-one and 2-methyl-7H-spiro[furo[3,4-b]pyridine-5,4'-piperidine]dihydrochloride using Huenig's Base according to the general procedure XXI. MS m/e: 390.5 ([M+H]$^+$).

Example 49

2-Methyl-1'-(4'-oxo-1,3-dihydro-4'H-spiro[indene-2,5'-[1,3]oxazol]-2'-yl)-7H-spiro[furo[3,4-b]pyridine-5,4'-piperidin]-7-one The title compound was obtained as light brown solid in 16% yield from 2'-amino-1,3-dihydro-4'H-spiro[indene-2, 5'-[1,3]oxazol]-4'-one and 2-methyl-7H-spiro[furo[3,4-b]pyridine-5,4'-piperidin]-7-one according to the general procedure XXI. MS m/e: 404 ([M+H]$^+$).

Example 50

2'-(6-Methyl-1'H,3H-spiro[furo[3,4-c]pyridine-1,4'-piperidin]-1'-yl)-1,3-dihydro-4'H-spiro[indene-2,5'-[1,3]oxazol]-4'-one The title compound was obtained as light brown solid in 16% yield from 2'-amino-1,3-dihydro-4'H-spiro[indene-2,5'-[1,3]oxazol]-4'-one and 6-methyl-3H-spiro[furo[3,4-c]pyridine-1,4'-piperidine] according to the general procedure XXI. MS m/e: 391 ([M+H]$^+$).

Example 51

6-Methyl-1'-(4'-oxo-1,3-dihydro-4'H-spiro[indene-2,5'-[1,3]oxazol]-2'-yl)-3H-spiro[furo[3,4-c]pyridine-1,4'-piperidin]-3-one The title compound was obtained as light brown solid in 15% yield from 2'-amino-1,3-dihydro-4'H-spiro[indene-2,5'-[1,3]oxazol]-4'-one and 6-methyl-3H-spiro[furo[3,4-c]pyridine-1,4'-piperidin]-3-one according to the general procedure XXI. MS m/e: 405 ([M+H]$^+$).

Example 52

2'-(3-Methyl-1'H,7H-spiro[furo[3,4-b]pyridine-5,4'-piperidin]-1'-yl)-1,3-dihydro-4'H-spiro[indene-2,5'-[1,3]oxazol]-4'-one The title compound was obtained as white solid in 27% yield from 2'-amino-1,3-dihydro-4'H-spiro[indene-2,5'-[1,3]oxazol]-4'-one and 3-methyl-7H-spiro[furo[3,4-b]pyridine-5,4'-piperidine] according to the general procedure XXI. MS m/e: 390 ([M+H]$^+$).

Example 53

3-Methyl-1'-(4'-oxo-1,3-dihydro-4'H-spiro[indene-2,5'-[1,3]oxazol]-2'-yl)-7H-spiro[furo[3,4-b]pyridine-5,4'-piperidin]-7-one The title compound was obtained as white solid in 54% yield from 2'-amino-1,3-dihydro-4'H-spiro[indene-2,5'-[1,3]oxazol]-4'-one and 3-methyl-7H-spiro[furo[3,4-b]pyridine-5,4'-piperidin]-7-one according to the general procedure XXI. MS m/e: 404 ([M+H]$^+$).

Example 54

6-Chloro-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one Example 55

4-Chloro-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one The title compounds were obtained from 2'-amino-1,3-dihydro-4'H-spiro[indene-2,5'-[1,3]oxazol]-4'-one and a mixture of 6-chloro-1H-spiro[furo[3,4-c]pyridine-3,4'-piperidin]-1-one and 4-chloro-1H-spiro[furo[3,4-c]pyridine-3,4'-piperidin]-1-one according to the general procedure XXI. Purification by HPLC yielded:

6-Chloro-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one: light brown solid, 12% yield. MS m/e: 424 ([M+H]$^+$).

4-Chloro-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one: light brown solid, 1% yield. MS m/e: 424 ([M+H]$^+$).

Example 56

2'-(1'H,3H-Spiro[2-benzofuran-1,4'-piperidin]-1'-yl)-5,7-dihydro-4'H-spiro[cyclopenta[b]pyridine-6,5'-[1,3]oxazol]-4'-one The title compound was obtained as colorless oil in 4% yield from 2-(4-oxo-5-(prop-2-ynyl)-2-(3H-spiro[isobenzofuran-1,4'-piperidine]-1'-yl)-4,5-dihydrooxazol-5-yl)acetonitrile and ethyne using cylopentadienylcobalt dicarbonyl as a catalyst according to the general procedure XXIII. MS m/e: 376 ([M+H]$^+$).

Example 57

3-(Chloromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one The title compound was obtained as off-white solid in 54% yield from 5,5-di(prop-2-ynyl)-2-(3H-spiro[isobenzofuran-1,4'-piperidine]-1'-yl)oxazol-4(5H)-one and 2-chloroacetonitrile using chloro(pentamethylcyclopentadienyl)(cyclooctadiene)ruthenium(II) as a catalyst according to the general procedure XXII. MS m/e: 424 ([M+H]$^+$).

Example 58

3-Methyl-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one In a 25 ml round-bottomed flask, 3-(chloromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-(0.03 g, 1 eq) and sodium acetate (0.015 g, 2.5 eq) were combined with methanol (3 ml) to give a light brown suspension. Palladium 10% on charcoal (0.023 g, 0.3 eq) was added. Hydrogen gas was bubbled through the reaction mixture for 5 minutes, and stirring was continued for 1 h under an atmosphere of 1 bar of hydrogen gas. The reaction mixture was filtered through a plug of celite and concentrated in vacuo. The title compound was obtained by flash chromatography as a light brown solid in 44% yield. MS m/e: 390 ([M+H]$^+$).

Example 59

3-(Fluoromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one The title compound was obtained as light brown oil in 28% yield from 5,5-di(prop-2-ynyl)-2-(3H-spiro[isobenzofuran-1,4'-piperidine]-1'-yl)oxazol-4(5H)-one and 2-fluoroacetonitrile using chloro(pentamethylcyclopentadienyl)(cyclooctadiene)ruthenium(II) as a catalyst according to the general procedure XXII. MS m/e: 408 ([M+H]$^+$).

Example 60

3-(Difluoromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one The title compound was obtained as light yellow solid in 85% yield from 5,5-di(prop-2-ynyl)-2-(3H-spiro[isobenzofuran-1,4'-piperidine]-1'-yl)oxazol-4(5H)-one and 2,2-difluoroacetonitrile using chloro(pentamethylcyclopentadienyl)(cyclooctadiene)ruthenium(II) as a catalyst according to the general procedure XXII. MS m/e: 426 ([M+H]$^+$).

Example 61

2'-(1'H,3H-Spiro[2-benzofuran-1,4'-piperidin]-1'-yl)-3-(trifluoromethyl)-5,7-dihydro-4'H-spiro[cyclopenta[c]pyridine-6,5'-[1,3]oxazol]-4'-one The title compound was obtained as off-white solid in 1% yield from 5,5-di(prop-2-ynyl)-2-(3H-spiro[isobenzofuran-1,4'-piperidine]-1'-yl)oxazol-4(5H)-one and 2,2,2-trifluoroacetonitrile using chloro(pentamethylcyclopentadienyl)(cyclooctadiene)ruthenium(II) as a catalyst according to the general procedure XXII. MS m/e: 444 ([M+H]$^+$).

Example 62

2'-(1'H,3H-Spiro[2-benzofuran-1,4'-piperidin]-1'-yl)-3,4-dihydro-2H,4'H-spiro[naphthalene-1,5'-[1,3]oxazol]-4'-one The title compound was obtained as light brown solid in 3% 2'-amino-3,4-dihydro-2H,4'H-spiro[naphthalene-1,5'-[1,3]oxazol]-4'-one and 3H-spiro[isobenzofuran-1,4'-piperidin]according to the general procedure XXI. MS m/e: 390 ([M+H]$^+$)

Example 63

1'-(4'-Oxo-3,4-dihydro-2H,4'H-spiro[naphthalene-1,5'-[1,3]oxazol]-2'-yl)-3H-spiro[2-benzofuran-1,4'-piperidin]-3-one The title compound was obtained as light yellow solid in 3% from 2'-amino-3,4-dihydro-2H,4'H-spiro[naphthalene-1,5'-[1,3]oxazol]-4'-one and 3H-spiro[isobenzofuran-1,4'-piperidin]-3-one according to the general procedure XXI. MS m/e: 403 ([M+H]$^+$).

Example 64

2'-(1'H,3H-Spiro[2-benzofuran-1,4'-piperidin]-1'-yl)-3,4-dihydro-1H,4'H-spiro[naphthalene-2,5'-[1,3]oxazol]-4'-one The title compound was obtained as white solid in 9% yield from 3H-spiro[isobenzofuran-1,4'-piperidine] and 2'-amino-3,4-dihydro-1H,4'H-spiro[naphthalene-2,5'-oxazol]-4'-one according to the general procedure XXI. MS m/e: 388 ([M+H]$^+$).

Example 65

1'-(4'-Oxo-3,4-dihydro-1H,4' H-spiro[naphthalene-2,5'-[1,3]oxazol]-2'-yl)-1' H,3H-spiro[2-benzofuran-1,4'-piperidin]-3-one The title compound was obtained as off-white solid in 37% from 2'-amino-3,4-dihydro-1H,4'H-spiro[naphthalene-2,5'-[1,3]oxazol]-4'-one and 3H-spiro[isobenzofuran-1,4'-piperidin]-3-one according to the general procedure according to the general procedure XXI. MS m/e: 403 ([M+H]$^+$)

Example 66

1'-[4'-Oxo-3,4-dihydro-1H,4'H-spiro[naphthalene-2,5'-[1,3]oxazol]-2'-yl]-1'H,3H-spiro[2-benzofuran-1,4'-piperidin]-3-one enantiomer A and Example 67

1'-[4'-Oxo-3,4-dihydro-1H,4'H-spiro[naphthalene-2,5'-[1,3]oxazol]-2'-yl]-1'1,3H-spiro[2-benzofuran-1,4'-piperidin]-3-one enantiomer B 1'-[4'-Oxo-3,4-dihydro-1H,4'H-spiro[naphthalene-2,5'-[1,3]oxazol]-2'-yl]-1'H,3H-spiro[2-benzofuran-1,4'-piperidin]-3-one enantiomer A and 1'-[4'-oxo-3,4-dihydro-1H,4'H-spiro[naphthalene-2,5'-[1,3]oxazol]-2'-yl]-1'H,3H-spiro[2-benzofuran-1,4'-piperidin]-3-one enantiomer B were obtained from 1'-(4'-oxo-3,4-dihydro-1H,4' H-spiro[naphthalene-2,5'-[1,3]oxazol]-2'-yl)-1'H,3H-spiro[2-benzofuran-1,4'-piperidin]-3-one by chiral HPLC separation on a Reprosil Chiral-NR column with n-heptane/ethanol as eluent. The compounds are cited in the order of elution:

1'-[4'-Oxo-3,4-dihydro-1H,4'H-spiro[naphthalene-2,5'-[1,3]oxazol]-2'-yl]-1'H,3H-spiro[2-benzofuran-1,4'-piperidin]-3-one enantiomer A (0.011 g, 11%) was obtained as off-white powder. MS m/e: 403 ([M+H]$^+$).

1'-[4'-Oxo-3,4-dihydro-1H,4'H-spiro[naphthalene-2,5'-[1,3]oxazol]-2'-yl]-1'H,3H-spiro[2-benzofuran-1,4'-piperidin]-3-one enantiomer B (0.011 g, 11%) was obtained as off-white powder. MS m/e: 403 ([M+H]$^+$).

Example 68

2'-(7,7-Dimethyl-1'H,7H-spiro[furo[3,4-b]pyridine-5,4'-piperidin]-1'-yl)-4-methoxy-1,3-dihydro-4'H-spiro[indene-2,5'-[1,3]oxazol]-4'-one The title compound was obtained as off-white solid in 41% yield from 2'-amino-4-methoxy-1,3-dihydro-4'H-spiro[indene-2,5'-oxazol]-4'-one and 7,7-dimethyl-7H-spiro[furo[3,4-b]pyridine-5,4'-piperidine] according to the general procedure XXI. MS m/e: 434 ([M+H]$^+$).

Example 69

2'-(7,7-Dimethyl-1'H,7H-spiro[furo[3,4-b]pyridine-5,4'-piperidin]-1'-yl)-4-hydroxy-1,3-dihydro-4'H-spiro[indene-2,5'-[1,3]oxazol]-4'-one To a solution of 2'-(7,7-dimethyl-1'H,7H-spiro[furo[3,4-b]pyridine-5,4'-piperidin]-1'-yl)-4-methoxy-1,3-dihydro-4'H-spiro[indene-2,5'-[1,3]oxazol]-4'-one (0.066 g, 0.152 mmol) in dichloromethane (1.5 ml) was added 1M boron tribromide solution in dichloromethane (0.457 ml, 0.457 mmol) at 0-5° C. The ice bath was removed after 5 minutes, and stirring was continued for 5 min. The excess boron tribromide was quenched with methanol (0.25 ml) at 0-5° C. and stirred for 5 minutes. The reaction mixture was partitioned between ethyl acetate (50 ml) and saturated aqueous sodium bicarbonate solution (25 ml). The layers were separated. The aqueous layer was extracted with two 40-ml portions of ethyl acetate. The combined organic layers were washed with one 25-ml portion of brine, dried over anhydrous sodium sulfate, filtered and concentrated in vacuo. Crystallization from ethyl acetate (1 ml) gave the title compound (0.041 g, 64%) as off-white solid. MS m/e: 420 ([M+H]$^+$).

Example 70

2'-(7,7-Dimethyl-1-oxido-1'H,7H-spiro[furo[3,4-b]pyridine-5,4'-piperidin]-1'-yl)-1,3-dihydro-4'H-spiro[indene-2,5'-[1,3]oxazol]-4'-one To a mixture of 2'-(7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one (0.300 g, 0.744 mmol) in dichloromethane (7.44 ml) was added m-chloroperbenzoic acid (0.192 g, 1.12 mmol). Stirring was continued for 72 h. The reaction mixture was partitioned between dichloromethane (30 ml) and saturated bicarbonate solution (30 ml). The layers were separated. The aqueous layer was extracted with three 30-ml portions of dichloromethane. The combined organic layers were washed with one 30-ml portion of brine, dried over anhydrous sodium sulfate, filtered and concentrated in vacuo. Purification by preparative RP-HPLC on a Gemini NX 3u 50×4.6 mm column with water/acetonitrile/triethylamine gave the title compound (0.20 g, 65%) as white solid. MS m/e: 420 ([M+H]$^+$).

Example 71

2'-(3-Hydroxy-7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one and Example 72

2'-(2-Hydroxy-7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one a) 7,7-Dimethyl-1'-(4'-oxo-1,3-dihydro-4'H-spiro[indene-2,5'-oxazole]-2'-yl)-7H-spiro[furo[3,4-b]pyridine-5,4'-piperidine]-3-yl acetate and 7,7-dimethyl-1'-(4'-oxo-1,3-dihydro-4'H-spiro[indene-2,5'-oxazole]-2'-yl)-7H-spiro[furo[3,4-b]pyridine-5,4'-piperidine]-2-yl acetate A solution of 2'-(7,7-dimethyl-1-oxido-1'H,7H-spiro[furo[3,4-b]pyridine-5,4'-piperidin]-1'-yl)-1,3-dihydro-4'H-spiro[indene-2,5'-[1,3]oxazol]-4'-one (0.140 g, 0.334 mol) and 2,4,6-trimethylpyridine (0.089 ml, 0.668 mmol) in acetic anhydride (3.15 ml, 33.4 mmol) was heated at 140° C. and stirred for 15 h. The reaction mixture was partitioned between ethyl acetate (50 ml) and saturated bicarbonate solution (75 ml). The layers were separated. The aqueous layer was extracted with two 50-ml portions of ethyl acetate. The combined organic layers were washed with one 30-ml portion of saturated ammonium chloride solution, dried over anhydrous sodium sulfate, filtered and concentrated in vacuo. Purification by preparative RP-HPLC on a Gemini 5 um C18 100×30 mm column with water/acetonitrile/formic acid gave 7,7-dimethyl-1'-(4'-oxo-1,3-dihydro-4'H-spiro[indene-2,5'-oxazole]-2'-yl)-7H-spiro[furo[3,4-b]pyridine-5,4'-piperidine]-3-yl acetate and 7,7-dimethyl-1'-(4'-oxo-1,3-dihydro-4'H-spiro[indene-2,5'-oxazole]-2'-yl)-7H-spiro[furo[3,4-b]pyridine-5,4'-piperidine]-2-yl acetate.

7,7-Dimethyl-1'-(4'-oxo-1,3-dihydro-4'H-spiro[indene-2,5'-oxazole]-2'-yl)-7H-spiro[furo[3,4-b]pyridine-5,4'-piperidine]-3-yl acetate was obtained as off-white solid in 6% yield. MS m/e: 462 ([M+H]$^+$).

7,7-Dimethyl-1'-(4'-oxo-1,3-dihydro-4'H-spiro[indene-2,5'-oxazole]-2'-yl)-7H-spiro[furo[3,4-b]pyridine-5,4'-piperidine]-2-yl acetate was obtained as off-white solid in 10% yield. MS m/e: 462 ([M+H]$^+$).

b) 2'-(3-Hydroxy-7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one To a solution of 7,7-dimethyl-1'-(4'-oxo-1,3-dihydro-4'H-spiro[indene-2,5'-oxazole]-2'-yl)-7H-spiro[furo[3,4-b]pyridine-5,4'-piperidine]-3-yl acetate (0.010 g, 0.0217 mmol) in methanol (1 ml) was added 5.4 M sodium methoxide solution in methanol (0.000401 ml, 2.17 µmol, Eq: 0.0999). Stirring was continued for 30 minutes. The reaction mixture was partitioned between dichloromethane (20 ml) and saturated ammonium chloride solution (10 ml). The layers were separated. The aqueous layer was extracted with three 20-ml portions of dichloromethane. The combined organic layers were dried over anhydrous sodium sulfate, filtered and concentrated in vacuo to give the crude title compound (0.009 g, 99%) as off-white solid. MS m/e: 420 ([M+H]$^+$).

c) 2'-(2-Hydroxy-7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one To a solution of 7,7-dimethyl-1'-(4'-oxo-1,3-dihydro-4'H-spiro[indene-2,5'-oxazole]-2'-yl)-7H-spiro[furo[3,4-b]pyridine-5,4'-piperidine]-2-yl acetate (0.015 g, 0.0325 mmol) in methanol (1 ml) was added sodium methoxide (0.000602 ml, 0.00325 mmol). Stirring was continued for 30 minutes. The reaction mixture was partitioned between dichloromethane (20 ml) and saturated ammonium chloride solution (10 ml). The layers were separated. The aqueous layer was extracted with three 20-ml portions of dichloromethane. The combined organic layers were dried over anhydrous sodium sulfate, filtered and concentrated in vacuo to give the crude title compound (0.012 g, 88%). MS m/e: 420 ([M+H]$^+$)

[1]Robben, et al. (2006). Am J Physiol Renal Physiol. 291, F257-70, "Cell biological aspects of the vasopressin type-2 receptor and aquaporin 2 water channel in nephrogenic diabetes insipidus"

[2]Neumann (2008). J Neuroendocrinol. 20, 858-65, "Brain oxytocin: a key regulator of emotional and social behaviours in both females and males"

[3]Ebner, et al. (2002). Eur J Neurosci. 15, 384-8, "Forced swimming triggers vasopressin release within the amygdala to modulate stress-coping strategies in rats"

[4]Kendler, et al. (2003). Arch Gen Psychiatry. 60, 789-96, "Life Event Dimensions of Loss, Humiliation, Entrapment, and Danger in the Prediction of Onsets of Major Depression and Generalized Anxiety"

[5]Regier, et al. (1998). Br J Psychiatry Suppl. 24-8, "Prevalence of anxiety disorders and their comorbidity with mood and addictive disorders"

[6]Bielsky, et al. (2004). Neuropsychopharmacology. 29, 483-93, "Profound impairment in social recognition and reduction in anxiety-like behavior in vasopressin Via receptor knockout mice"

[7]Landgraf, et al. (1995). Regul Pept. 59, 229-39, "V1 vasopressin receptor antisense oligodeoxynucleotide into septum reduces vasopressin binding, social discrimination abilities, and anxiety-related behavior in rats"

[8]Yirmiya, et al. (2006). 11, 488-94, "Association between the arginine vasopressin 1a receptor (AVPR1a) gene and autism in a family-based study: mediation by socialization skills"

[9]Thompson, et al. (2004). Psychoneuroendocrinology. 29, 35-48, "The effects of vasopressin on human facial responses related to social communication"

[10]Raskind, et al. (1987). Biol Psychiatry. 22, 453-62, "Antipsychotic drugs and plasma vasopressin in normals and acute schizophrenic patients"

[11]Altemus, et al. (1992). Arch Gen Psychiatry. 49, 9-20, "Abnormalities in the regulation of vasopressin and corticotropin releasing factor secretion in obsessive-compulsive disorder"

[12]Genes, Brain and Behavior (2011) 10: 228-235

[13]Curr. Opin. Neurobiol. 19, 231-234 (2009)

[14]Kalsbeek, A., E. Fliers, M. A. Hofman, D. F. Swaab and R. M. Buijs. 2010. Vasopressin and the output of the hypothalamic biological clock.

[15]Schwartz, W. J., R. J. Coleman and S. M. Reppert. 1983. A daily vasopressin rhythm in rat cerebrospinal fluid. Brain Res 263: 105-12

[16]Groblewski, T. A., A. A. Nunez and R. M. Gold. 1981. Circadian rhythms in vasopressin deficient rats. Brain Res Bull 6: 125-30

[17]Albers, H. E., C. F. Ferris, S. E. Leeman and B. D. Goldman. 1984. Avian pancreatic polypeptide phase shifts hamster circadian rhythms when microinjected into the suprachiasmatic region. Science 223: 833-5

[18]Yoshiaki Yamaguchi, Toru Suzuki, Yasutaka Mizoro, Hiroshi Kori, Kazuki Okada, Yulin Chen, Jean-Michel Fustin, Fumiyoshi Yamazaki, Naoki Mizuguchi, Jing Zhang, Xin Dong, Gozoh Tsujimoto, Yasushi Okuno, Masao Doi, Hitoshi Okamura. Mice Genetically Deficient in Vasopressin V1a and V1b Receptors Are Resistant to Jet Lag. (2013) Science, 342: 85-90

[19]Compendium of Chemical Terminology, 2nd, A. D. McNaught & A. Wilkinson (Eds). Blackwell Scientific Publications, Oxford (1997)

The invention claimed is:

1. A compound of formula I,

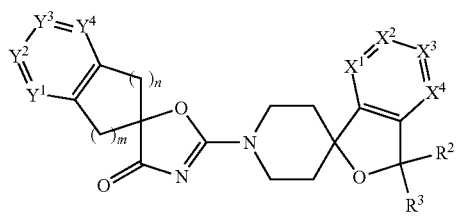

I wherein
$X^1$ is C—$R^1$ or N;
$X^2$ is C—$R^1$ or N;
$X^3$ is C—$R^1$ or N;
$X^4$ is C—$R^1$, N or NO;
whereby only one of $X^1$, $X^2$, $X^3$ and $X^4$ is N;

$R^1$ each separately is selected from the group consisting of hydrogen, halogen, hydroxy, $C_{1-6}$-alkyl and $C_{1-6}$-alkoxy;
$R^2$ is selected from the group consisting of H and $C_{1-6}$-alkyl;
$R^3$ is selected from the group consisting of H and $C_{1-6}$-alkyl;
or $R^2$ and $R^3$ together are =O;
$Y^1$ is C—$R^4$ or N;
$Y^2$ is C—$R^4$ or N;
$Y^3$ is C—$R^4$ or N;
$Y^4$ is C—$R^4$ or N;
whereby only one of $Y^1$, $Y^2$, $Y^3$ and $Y^4$ is N;
$R^4$ each separately is selected from the group consisting of hydrogen, halogen, halogen-$C_{1-6}$-alkyl, hydroxy, $C_{1-6}$-alkyl, $C_{1-6}$-alkoxy and Si($C_{1-6}$-alkyl)$_3$;
m is 1 or 2; and
n is 1;
or pharmaceutically acceptable salts thereof.

2. The compound of claim 1, wherein
$X^1$ is C—H or N;
$X^3$ is C—$R^1$;
$X^4$ is C—H or N;
$R^1$ each separately is selected from the group consisting of hydrogen, halogen, hydroxy, and $C_{1-6}$-alkyl;
$Y^1$ is C—H or N;
$Y^4$ is C—H or N; and
$R^4$ each separately is selected from the group consisting of hydrogen, halogen, hydroxy and $C_{1-6}$-alkyl.

3. The compound of claim 1, wherein
$X^1$, $X^2$, $X^3$ and $X^4$ are each CH;
$R^2$ and $R^3$ are each H;
$Y^1$ and $Y^4$ are each CH; and
$Y^2$ and $Y^3$ are each CH or CF.

4. The compound of claim 1, wherein
$X^1$, $X^2$ and $X^3$ are each CH and $X^4$ is N;
$R^2$ and $R^3$ are each $C_{1-6}$-alkyl; and
$Y^1$, $Y^2$, $Y^3$ and $Y^4$ are each CH.

5. The compound of claim 1, wherein,
$X^1$ is C—$R^1$;
$X^2$ is C—$R^1$;
$X^3$ is C—$R^1$;
$X^4$ is N or NO;
or pharmaceutically acceptable salts thereof.

6. The compound of claim 5, wherein
$X^1$ $X^2$ and $X^3$ are each CH;
$R^2$ and $R^3$ are each $C_{1-6}$-alkyl; and
$Y^1$, $Y^2$, $Y^3$ and $Y^4$ are each CH.

7. The compound of claim 5, wherein
$X^1$, $X^2$ and $X^3$ are each CH;
$R^2$ and $R^3$ are each H; and
$Y^1$, $Y^2$, $Y^3$ and $Y^4$ are each CH.

8. A compound selected from the group consisting of
(1R)-2'-(1'H,3H-spiro[2-benzofuran-1,4'-piperidin]-1'-yl)-2,3-dihydro-4'H-spiro[indene-1,5'[1,3]oxazol]-4'-one,
(1S)-2'-(1'H,3H-spiro[2-benzofuran-1,4'-piperidin]-1'-yl)-2,3-dihydro-4'H-spiro[indene-1,5'[1,3]oxazol]-4'-one,
1'-(4'-oxo-1,3-dihydro-4'H-spiro[indene-2,5'-[1,3]oxazol]-2'-yl)-3H-spiro[2-benzofuran-1,4'-piperidin]-3-one,
1'-(4'-oxo-3,4-dihydro-1H,4'H-spiro[naphthalene-2,5'-[1,3]oxazol]-2'-yl)-1'H,3H-spiro[2-benzofuran-1,4'-piperidin]-3-one, 1'-(4'-oxo-3,4-dihydro-2H,4'H-spiro[naphthalene-1,5'-[1,3]oxazol]-2'-yl)-3H-spiro[2-benzofuran-1,4'-piperidin]-3-one,
1'-(5,6-difluoro-4'-oxo-1,3-dihydro-4'H-spiro[indene-2,5'-[1,3]oxazol]-2'-yl)-3H-spiro[2-benzofuran-1,4'-piperidin]-3-one,
1'-(5,6-dihydroxy-4'-oxo-1,3-dihydro-4'H-spiro[indene-2,5'-[1,3]oxazol]-2'-yl)-3H-spiro[2-benzofuran-1,4'-piperidin]-3-one,
1'-(5,6-dimethoxy-4'-oxo-1,3-dihydro-4'H-spiro[indene-2,5'-[1,3]oxazol]-2'-yl)-3H-spiro[2-benzofuran-1,4'-piperidin]-3-one,
1'-(5,6-dimethyl-4'-oxo-1,3-dihydro-4'H-spiro[indene-2,5'-[1,3]oxazol]-2'-yl)-3H-spiro[2-benzofuran-1,4'-piperidin]-3-one,
1'-(5-hydroxy-4'-oxo-1,3-dihydro-4'H-spiro[indene-2,5'-[1,3]oxazol]-2'-yl)-3H-spiro[2-benzofuran-1,4'-piperidin]-3-one,
1'-(5-methoxy-4'-oxo-1,3-dihydro-4'H-spiro[indene-2,5'-[1,3]oxazol]-2'-yl)-3H-spiro[2-benzofuran-1,4'-piperidin]-3-one,
1'-(5-methyl-4'-oxo-1,3-dihydro-4'H-spiro[indene-2,5'-[1,3]oxazol]-2'-yl)-3H-spiro[2-benzofuran-1,4'-piperidin]-3-one,
1'-[(2R)-4'-oxo-3,4-dihydro-1H,4'H-spiro[naphthalene-2,5'-[1,3]oxazol]-2'-yl]-1'H,3H-spiro[2-benzofuran-1,4'-piperidin]-3-one,
1'-[(2R)-5-methyl-4'-oxo-1,3-dihydro-4'H-spiro[indene-2,5'-[1,3]oxazol]-2'-yl]-3H-spiro[2-benzofuran-1,4'-piperidin]-3-one,
1'-[(2S)-4'-oxo-3,4-dihydro-1H,4'H-spiro[naphthalene-2,5'-[1,3]oxazol]-2'-yl]-1'H,3H-spiro[2-benzofuran-1,4'-piperidin]-3-one,
1'-[(2S)-5-methyl-4'-oxo-1,3-dihydro-4'H-spiro[indene-2,5'-[1,3]oxazol]-2'-yl]-3H-spiro[2-benzofuran-1,4'-piperidin]-3-one,
2'-(1'H,3H-spiro[2-benzofuran-1,4'-piperidin]-1'-yl)-1,3-dihydro-4'H-spiro[indene-2,5'-[1,3]oxazol]-4'-one,
2'-(1'H,3H-spiro[2-benzofuran-1,4'-piperidin]-1'-yl)-3-(trifluoromethyl)-5,7-dihydro-4'H-spiro[cyclopenta[c]pyridine-6,5'-[1,3]oxazol]-4'-one,
2'-(1'H,3H-spiro[2-benzofuran-1,4'-piperidin]-1'-yl)-3,4-dihydro-2H,4'H-spiro[naphthalene-1,5'-[1,3]oxazol]-4'-one,
2'-(1'H,3H-spiro[2-benzofuran-1,4'-piperidin]-1'-yl)-3,4-dihydro-1H,4'H-spiro[naphthalene-2,5'-[1,3]oxazol]-4'-one,
2'-(1'H,3H-spiro[2-benzofuran-1,4'-piperidin]-1'-yl)-5-(trimethylsilyl)-1,3-dihydro-4'H-spiro[indene-2,5'-[1,3]oxazol]-4'-one,
2'-(1'H,3H-spiro[2-benzofuran-1,4'-piperidin]-1'-yl)-5,7-dihydro-4'H-spiro[cyclopenta[b]pyridine-6,5'-[1,3]oxazol]-4'-one,
2'-(2-hydroxy-7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one,
2'-(2-methyl-1'H,5H-spiro[furo[3,4-b]pyridine-7,4'-piperidin]-1'-yl)-1,3-dihydro-4'H-spiro[indene-2,5'-[1,3]oxazol]-4'-one,
2'-(2-methyl-1'H,7H-spiro[furo[3,4-b]pyridine-5,4'-piperidin]-1'-yl)-1,3-dihydro-4'H-spiro[indene-2,5'-[1,3]oxazol]-4'-one,
2'3,3-dimethyl-1'H,3H-spiro[2-benzofuran-1,4'-piperidin]-1'-yl)-1,3-dihydro-4'H-spiro[indene-2,5'-[1,3]oxazol]-4'-one,
2'-(3-hydroxy-7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one,
2'-(3-methyl-1'H,5H-spiro[furo[3,4-b]pyridine-7,4'-piperidin]-1'-yl)-1,3-dihydro-4'H-spiro[indene-2,5'-[1,3]oxazol]-4'-one,
2'-(3-methyl-1'H,7H-spiro[furo[3,4-b]pyridine-5,4'-piperidin]-1'-yl)-1,3-dihydro-4'H-spiro[indene-2,5'-[1,3]oxazol]-4'-one,
2'-(4-methyl-1'H,3H-spiro[2-benzofuran-1,4'-piperidin]-1'-yl)-1,3-dihydro-4'H-spiro[indene-2,5'-[1,3]oxazol]-4'-one,
2'-(5,5-dimethyl-1'H,5H-spiro[furo[3,4-b]pyridine-7,4'-piperidin]-1'-yl)-1,3-dihydro-4'H-spiro[indene-2,5'-[1,3]oxazol]-4'-one,
2'-(6-methyl-1H,1'H-spiro[furo[3,4-c]pyridine-3,4'-piperidin]-1'-yl)-1,3-dihydro-4'H-spiro[indene-2,5'-[1,3]oxazol]-4'-one,
2'-(6-methyl-1'H,3H-spiro[furo[3,4-c]pyridine-1,4'-piperidin]-1'-yl)-1,3-dihydro-4'H-spiro[indene-2,5'-[1,3]oxazol]-4'-one,
2'-(7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one,
2'-(7,7-dimethyl-1'H,7H-spiro[furo[3,4-b]pyridine-5,4'-piperidin]-1'-yl)-5-methoxy-1,3-dihydro-4'H-spiro[indene-2,5'-[1,3]oxazol]-4'-one,
2'-(7,7-dimethyl-1'H,7H-spiro[furo[3,4-b]pyridine-5,4'-piperidin]-1'-yl)-5-hydroxy-1,3-dihydro-4'H-spiro[indene-2,5'-[1,3]oxazol]-4'-one,
2'-(7,7-dimethyl-1'H,7H-spiro[furo[3,4-b]pyridine-5,4'-piperidin]-1'-yl)-4-methoxy-1,3-dihydro-4'H-spiro[indene-2,5'-[1,3]oxazol]-4'-one,
2'-(7,7-dimethyl-1'H,7H-spiro[furo[3,4-b]pyridine-5,4'-piperidin]-1'-yl)-4-hydroxy-1,3-dihydro-4'H-spiro[indene-2,5'-[1,3]oxazol]-4'-one,
2'-(7,7-dimethyl-1-oxido-1'H,7H-spiro[furo[3,4-b]pyridine-5,4'-piperidin]-1'-yl)-1,3-dihydro-4'H-spiro[indene-2,5'-[1,3]oxazol]-4'-one,
2-methyl-1'-(4'-oxo-1,3-dihydro-4'H-spiro[indene-2,5'-[1,3]oxazol]-2'-yl)-5H-spiro[furo[3,4-b]pyridine-7,4'-piperidin]-5-one,
2-methyl-1'-(4'-oxo-1,3-dihydro-4'H-spiro[indene-2,5'-[1,3]oxazol]-2'-yl)-7H-spiro[furo[3,4-b]pyridine-5,4'-piperidin]-7-one,
2'-spiro[5H-furo[3,4-b]pyridine-7,4'-piperidine]-1'-yl-spiro[indane-2,5'-oxazole]-4'-one,
2'-spiro[7H-furo[3,4-b]pyridine-5,4'-piperidine]-1'-yl-spiro[indane-2,5'-oxazole]-4'-one,
3-(chloromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one,
3-(difluoromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one,
3-(fluoromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one,
3-methyl-1'-(4'-oxo-1,3-dihydro-4'H-spiro[indene-2,5'-[1,3]oxazol]-2'-yl)-5H-spiro[furo[3,4-b]pyridine-7,4'-piperidin]-5-one,
3-methyl-1'-(4'-oxo-1,3-dihydro-4'H-spiro[indene-2,5'-[1,3]oxazol]-2'-yl)-7H-spiro[furo[3,4-b]pyridine-5,4'-piperidin]-7-one,
3-methyl-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one, 4-chloro-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one,
4-fluoro-1'-(4'-oxo-1,3-dihydro-4'H-spiro[indene-2,5'-[1,3]oxazol]-2'-yl)-3H-spiro[2-benzofuran-1,4'-piperidin]-3-one,
4-methyl-1'-(4'-oxo-1,3-dihydro-4'H-spiro[indene-2,5'-[1,3]oxazol]-2'-yl)-3H-spiro[2-benzofuran-1,4'-piperidin]-3-one,
5,6-difluoro-2'-(1'H,3H-spiro[2-benzofuran-1,4'-piperidin]-1'-yl)-1,3-dihydro-4'H-spiro[indene-2,5'-[1,3]oxazol]-4'-one,
5,6-dihydroxy-1'-(4'-oxo-1,3-dihydro-4'H-spiro[indene-2,5'-[1,3]oxazol]-2'-yl)-3H-spiro[2-benzofuran-1,4'-piperidin]-3-one,
5,6-dimethoxy-1'-(4'-oxo-1,3-dihydro-4'H-spiro[indene-2,5'-[1,3]oxazol]-2'-yl)-3H-spiro[2-benzofuran-1,4'-piperidin]-3-one,
5,6-dimethyl-2'-(1'H,3H-spiro[2-benzofuran-1,4'-piperidin]-1'-yl)-1,3-dihydro-4'H-spiro[indene-2,5'-[1,3]oxazol]-4'-one,
5-bromo-1'-(4'-oxo-1,3-dihydro-4'H-spiro[indene-2,5'-[1,3]oxazol]-2'-yl)-3H-spiro[2-benzofuran-1,4'-piperidin]-3-one,
5-chloro-2'-(1'H,3H-spiro[2-benzofuran-1,4'-piperidin]-1'-yl)-1,3-dihydro-4'H-spiro[indene-2,5'-[1,3]oxazol]-4'-one,
5-fluoro-1'-(4'-oxo-1,3-dihydro-4'H-spiro[indene-2,5'-[1,3]oxazol]-2'-yl)-3H-spiro[2-benzofuran-1,4'-piperidin]-3-one,
5-fluoro-2'-(1'H,3H-spiro[2-benzofuran-1,4'-piperidin]-1'-yl)-1,3-dihydro-4'H-spiro[indene-2,5'-[1,3]oxazol]-4'-one,
5-hydroxy-1'-(4'-oxo-1,3-dihydro-4'H-spiro[indene-2,5'-[1,3]oxazol]-2'-yl)-3H-spiro[2-benzofuran-1,4'-piperidin]-3-one,
5-methoxy-1'-(4'-oxo-1,3-dihydro-4'H-spiro[indene-2,5'-[1,3]oxazol]-2'-yl)-3H-spiro[2-benzofuran-1,4'-piperidin]-3-one,
5-methyl-1'-(4'-oxo-1,3-dihydro-4'H-spiro[indene-2,5'-[1,3]oxazol]-2'-yl)-3H-spiro[2-benzofuran-1,4'-piperidin]-3-one,
5-methyl-2'-(1'H,3H-spiro[2-benzofuran-1,4'-piperidin]-1'-yl)-1,3-dihydro-4'H-spiro[indene-2,5'-[1,3]oxazol]-4'-one,
6-chloro-1'-(4'-oxo-1,3-dihydro-4'H-spiro[indene-2,5'-[1,3]oxazol]-2'-yl)-3H-spiro[2-benzofuran-1,4'-piperidin]-3-one,
6-chloro-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one,
6-hydroxy-1'-(4'-oxo-1,3-dihydro-4'H-spiro[indene-2,5'-[1,3]oxazol]-2'-yl)-3H-spiro[2-benzofuran-1,4'-piperidin]-3-one,
6-methoxy-1'-(4'-oxo-1,3-dihydro-4'H-spiro[indene-2,5'-[1,3]oxazol]-2'-yl)-3H-spiro[2-benzofuran-1,4'-piperidin]-3-one,
6-methyl-1'-(4'-oxo-1,3-dihydro-4'H-spiro[indene-2,5'-[1,3]oxazol]-2'-yl)-3H-spiro[2-benzofuran-1,4'-piperidin]-3-one,
6-methyl-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one,
6-methyl-1'-(4'-oxo-1,3-dihydro-4'H-spiro[indene-2,5'-[1,3]oxazol]-2'-yl)-3H-spiro[furo[3,4-c]pyridine-1,4'-piperidin]-3-one, and
7-fluoro-1'-(4'-oxo-1,3-dihydro-4'H-spiro[indene-2,5'-[1,3]oxazol]-2'-yl)-3H-spiro[2-benzofuran-1,4'-piperidin]-3-one, or a pharmaceutically acceptable salt thereof.

9. A compound selected from the group consisting of
(+)-2'-(1'H,3H-spiro[2-benzofuran-1,4'-piperidin]-1'-yl)-2,3-dihydro-4'H-spiro[indene-1,5'[1,3]oxazol]-4'-one,
(−)-2'-(1'H,3H-spiro[2-benzofuran-1,4'-piperidin]-1'-yl)-2,3-dihydro-4'H-spiro[indene-1,5'[1,3]oxazol]-4'-one,
1'-(4'-oxo-1,3-dihydro-4'H-spiro[indene-2,5'-[1,3]oxazol]-2'-yl)-3H-spiro[2-benzofuran-1,4'-piperidin]-3-one,
1'-(4'-oxo-3,4-dihydro-1H,4'H-spiro[naphthalene-2,5'-[1,3]oxazol]-2'-yl)-1'H,3H-spiro[2-benzofuran-1,4'-piperidin]-3-one,
1'-(4'-oxo-3,4-dihydro-2H,4'H-spiro[naphthalene-1,5'-[1,3]oxazol]-2'-yl)-3H-spiro[2-benzofuran-1,4'-piperidin]-3-one,
1'-(5,6-difluoro-4'-oxo-1,3-dihydro-4'H-spiro[indene-2,5'-[1,3]oxazol]-2'-yl)-3H-spiro[2-benzofuran-1,4'-piperidin]-3-one,
1'-(5,6-dihydroxy-4'-oxo-1,3-dihydro-4'H-spiro[indene-2,5'-[1,3]oxazol]-2'-yl)-3H-spiro[2-benzofuran-1,4'-piperidin]-3-one,
1'-(5,6-dimethoxy-4'-oxo-1,3-dihydro-4'H-spiro[indene-2,5'-[1,3]oxazol]-2'-yl)-3H-spiro[2-benzofuran-1,4'-piperidin]-3-one,
1'-(5,6-dimethyl-4'-oxo-1,3-dihydro-4'H-spiro[indene-2,5'-[1,3]oxazol]-2'-yl)-3H-spiro[2-benzofuran-1,4'-piperidin]-3-one,
1'-(5-hydroxy-4'-oxo-1,3-dihydro-4'H-spiro[indene-2,5'-[1,3]oxazol]-2'-yl)-3H-spiro[2-benzofuran-1,4'-piperidin]-3-one,
1'-(5-methoxy-4'-oxo-1,3-dihydro-4'H-spiro[indene-2,5'-[1,3]oxazol]-2'-yl)-3H-spiro[2-benzofuran-1,4'-piperidin]-3-one,
1'-(5-methyl-4'-oxo-1,3-dihydro-4'H-spiro[indene-2,5'-[1,3]oxazol]-2'-yl)-3H-spiro[2-benzofuran-1,4'-piperidin]-3-one,
1'-[4'-oxo-3,4-dihydro-1H,4'H-spiro[naphthalene-2,5'-[1,3]oxazol]-2'-yl]-1'H,3H-spiro[2-benzofuran-1,4'-piperidin]-3-one enantiomer A,
1'-[4'-oxo-3,4-dihydro-1H,4'H-spiro[naphthalene-2,5'-[1,3]oxazol]-2'-yl]-1'H,3H-spiro[2-benzofuran-1,4'-piperidin]-3-one enantiomer B,
(−)-1'-[5-methyl-4'-oxo-1,3-dihydro-4'H-spiro[indene-2,5'-[1,3]oxazol]-2'-yl]-3H-spiro[2-benzofuran-1,4'-piperidin]-3-one,
(+)-1'5-methyl-4'-oxo-1,3-dihydro-4'H-spiro[indene-2,5'-[1,3]oxazol]-2'-yl]-3H-spiro[2-benzofuran-1,4'-piperidin]-3-one,
2'-(1'H,3H-spiro[2-benzofuran-1,4'-piperidin]-1'-yl)-1,3-dihydro-4'H-spiro[indene-2,5'-[1,3]oxazol]-4'-one,
2'-(1'H,3H-spiro[2-benzofuran-1,4'-piperidin]-1'-yl)-3-(trifluoromethyl)-5,7-dihydro-4'H-spiro[cyclopenta[c]pyridine-6,5'-[1,3]oxazol]-4'-one,
2'-(1'H,3H-spiro[2-benzofuran-1,4'-piperidin]-1'-yl)-3,4-dihydro-2H,4'H-spiro[naphthalene-1,5'-[1,3]oxazol]-4'-one,
2'-(1'H,3H-spiro[2-benzofuran-1,4'-piperidin]-1'-yl)-3,4-dihydro-1H,4'H-spiro[naphthalene-2,5'-[1,3]oxazol]-4'-one,
2'-(1'H,3H-spiro[2-benzofuran-1,4'-piperidin]-1'-yl)-5-(trimethylsilyl)-1,3-dihydro-4'H-spiro[indene-2,5'-[1,3]oxazol]-4'-one, 2'-(1'H,3H-spiro[2-benzofuran-1,4'-piperidin]-1'-yl)-5,7-dihydro-4'H-spiro[cyclopenta[b]pyridine-6,5'-[1,3]oxazol]-4'-one,
2'-(2-methyl-1'H,5H-spiro[furo[3,4-b]pyridine-7,4'-piperidin]-1'-yl)-1,3-dihydro-4'H-spiro[indene-2,5'-[1,3]oxazol]-4'-one,
2'-(2-methyl-1'H,7H-spiro[furo[3,4-b]pyridine-5,4'-piperidin]-1'-yl)-1,3-dihydro-4'H-spiro[indene-2,5'-[1,3]oxazol]-4'-one,
2'-(3,3-dimethyl-1'H,3H-spiro[2-benzofuran-1,4'-piperidin]-1'-yl)-1,3-dihydro-4'H-spiro[indene-2,5'-[1,3]oxazol]-4'-one,
2'-(3-methyl-1'H,5H-spiro[furo[3,4-b]pyridine-7,4'-piperidin]-1'-yl)-1,3-dihydro-4'H-spiro[indene-2,5'-[1,3]oxazol]-4'-one,
2'-(3-methyl-1'H,7H-spiro[furo[3,4-b]pyridine-5,4'-piperidin]-1'-yl)-1,3-dihydro-4'H-spiro[indene-2,5'-[1,3]oxazol]-4'-one,
2'-(4-methyl-1'H,3H-spiro[2-benzofuran-1,4'-piperidin]-1'-yl)-1,3-dihydro-4'H-spiro[indene-2,5'-[1,3]oxazol]-4'-one,
2'-(5,5-dimethyl-1'H,5H-spiro[furo[3,4-b]pyridine-7,4'-piperidin]-1'-yl)-1,3-dihydro-4'H-spiro[indene-2,5'-[1,3]oxazol]-4'-one,
2'-(6-methyl-1H, 1'H-spiro[furo[3,4-c]pyridine-3,4'-piperidin]-1'-yl)-1,3-dihydro-4'H-spiro[indene-2,5'-[1,3]oxazol]-4'-one,
2'-(6-methyl-1'H,3H-spiro[furo[3,4-c]pyridine-1,4'-piperidin]-1'-yl)-1,3-dihydro-4'H-spiro[indene-2,5'-[1,3]oxazol]-4'-one,
2'-(7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one,
2'-(7,7-dimethyl-1'H,7H-spiro[furo[3,4-b]pyridine-5,4'-piperidin]-1'-yl)-5-methoxy-1,3-dihydro-4'H-spiro[indene-2,5'-[1,3]oxazol]-4'-one,
2'-(7,7-dimethyl-1'H,7H-spiro[furo[3,4-b]pyridine-5,4'-piperidin]-1'-yl)-5-hydroxy-1,3-dihydro-4'H-spiro[indene-2,5'-[1,3]oxazol]-4'-one,
2-methyl-1'-(4'-oxo-1,3-dihydro-4'H-spiro[indene-2,5'-[1,3]oxazol]-2'-yl)-5H-spiro[furo[3,4-b]pyridine-7,4'-piperidin]-5-one,
2-methyl-1'-(4'-oxo-1,3-dihydro-4'H-spiro[indene-2,5'-[1,3]oxazol]-2'-yl)-7H-spiro[furo[3,4-b]pyridine-5,4'-piperidin]-7-one,
2'-(1'H,5H-spiro[furo[3,4-b]pyridine-7,4'-piperidin]-1'-yl)-1,3-dihydro-4'H-spiro[indene-2,5'-[1,3]oxazol]-4'-one,
2'-(1'H,7H-spiro[furo[3,4-b]pyridine-5,4'-piperidin]-1'-yl)-1,3-dihydro-4'H-spiro[indene-2,5'-[1,3]oxazol]-4'-one,
3-(chloromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one,
3-(difluoromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one,
3-(fluoromethyl)-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one,
3-methyl-1'-(4'-oxo-1,3-dihydro-4'H-spiro[indene-2,5'-[1,3]oxazol]-2'-yl)-5H-spiro[furo[3,4-b]pyridine-7,4'-piperidin]-5-one,
3-methyl-1'-(4'-oxo-1,3-dihydro-4'H-spiro[indene-2,5'-[1,3]oxazol]-2'-yl)-7H-spiro[furo[3,4-b]pyridine-5,4'-piperidin]-7-one,
3-methyl-2'-(1'H,3H-spiro[2-benzofuran-1,4'-piperidin]-1'-yl)-5,7-dihydro-4'H-spiro[cyclopenta[c]pyridine-6,5'-[1,3]oxazol]-4'-one,
4-chloro-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one,
4-fluoro-1'-(4'-oxo-1,3-dihydro-4'H-spiro[indene-2,5'-[1,3]oxazol]-2'-yl)-3H-spiro[2-benzofuran-1,4'-piperidin]-3-one,
4-methyl-1'-(4'-oxo-1,3-dihydro-4'H-spiro[indene-2,5'-[1,3]oxazol]-2'-yl)-3H-spiro[2-benzofuran-1,4'-piperidin]-3-one,
5,6-difluoro-2'-(1'H,3H-spiro[2-benzofuran-1,4'-piperidin]-1'-yl)-1,3-dihydro-4'H-spiro[indene-2,5'-[1,3]oxazol]-4'-one,
5,6-dihydroxy-1'-(4'-oxo-1,3-dihydro-4'H-spiro[indene-2,5'-[1,3]oxazol]-2'-yl)-3H-spiro[2-benzofuran-1,4'-piperidin]-3-one,
5,6-dimethoxy-1'-(4'-oxo-1,3-dihydro-4'H-spiro[indene-2,5'-[1,3]oxazol]-2'-yl)-3H-spiro[2-benzofuran-1,4'-piperidin]-3-one,
5,6-dimethyl-2'-(1'H,3H-spiro[2-benzofuran-1,4'-piperidin]-1'-yl)-1,3-dihydro-4'H-spiro[indene-2,5'-[1,3]oxazol]-4'-one,
5-bromo-1'-(4'-oxo-1,3-dihydro-4'H-spiro[indene-2,5'-[1,3]oxazol]-2'-yl)-3H-spiro[2-benzofuran-1,4'-piperidin]-3-one,
5-chloro-2'-(1'H,3H-spiro[2-benzofuran-1,4'-piperidin]-1'-yl)-1,3-dihydro-4'H-spiro[indene-2,5'-[1,3]oxazol]-4'-one,
5-fluoro-1'-(4'-oxo-1,3-dihydro-4'H-spiro[indene-2,5'-[1,3]oxazol]-2'-yl)-3H-spiro[2-benzofuran-1,4'-piperidin]-3-one,
5-fluoro-2'-(1'H,3H-spiro[2-benzofuran-1,4'-piperidin]-1'-yl)-1,3-dihydro-4'H-spiro[indene-2,5'-[1,3]oxazol]-4'-one,
5-hydroxy-1'-(4'-oxo-1,3-dihydro-4'H-spiro[indene-2,5'-[1,3]oxazol]-2'-yl)-3H-spiro[2-benzofuran-1,4'-piperidin]-3-one,
5-methoxy-1'-(4'-oxo-1,3-dihydro-4'H-spiro[indene-2,5'-[1,3]oxazol]-2'-yl)-3H-spiro[2-benzofuran-1,4'-piperidin]-3-one,
5-methyl-1'-(4'-oxo-1,3-dihydro-4'H-spiro[indene-2,5'-[1,3]oxazol]-2'-yl)-3H-spiro[2-benzofuran-1,4'-piperidin]-3-one,
5-methyl-2'-(1'H,3H-spiro[2-benzofuran-1,4'-piperidin]-1'-yl)-1,3-dihydro-4'H-spiro[indene-2,5'-[1,3]oxazol]-4'-one,
6-chloro-1'-(4'-oxo-1,3-dihydro-4'H-spiro[indene-2,5'-[1,3]oxazol]-2'-yl)-3H-spiro[2-benzofuran-1,4'-piperidin]-3-one,
6-chloro-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one,
6-hydroxy-1'-(4'-oxo-1,3-dihydro-4'H-spiro[indene-2,5'-[1,3]oxazol]-2'-yl)-3H-spiro[2-benzofuran-1,4'-piperidin]-3-one,
6-methoxy-1'-(4'-oxo-1,3-dihydro-4'H-spiro[indene-2,5'-[1,3]oxazol]-2'-yl)-3H-spiro[2-benzofuran-1,4'-piperidin]-3-one,
6-methyl-1'-(4'-oxo-1,3-dihydro-4'H-spiro[indene-2,5'-[1,3]oxazol]-2'-yl)-3H-spiro[2-benzofuran-1,4'-piperidin]-3-one,
6-methyl-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one, 6-methyl-1'-(4'-oxo-1,3-dihydro-4'H-spiro[indene-2,5'-[1,3]oxazol]-2'-yl)-3H-spiro[furo[3,4-c]pyridine-1,4'-piperidin]-3-one, and 7-fluoro-1'-(4'-oxo-1,3-dihydro-4'H-spiro[indene-2,5'-[1,3]oxazol]-2'-yl)-3H-spiro[2-benzofuran-1,4'-piperidin]-3-one, or a pharmaceutically acceptable salt thereof.

10. A compound selected from the group consisting of

1'-(4'-oxo-1,3-dihydro-4'H-spiro[indene-2,5'-[1,3]oxazol]-2'-yl)-3H-spiro[2-benzofuran-1,4'-piperidin]-3-one, 1'-(5,6-difluoro-4'-oxo-1,3-dihydro-4'H-spiro[indene-2,5'-[1,3]oxazol]-2'-yl)-3H-spiro[2-benzofuran-1,4'-piperidin]-3-one, 1'-(5,6-dihydroxy-4'-oxo-1,3-dihydro-4'H-spiro[indene-2,5'-[1,3]oxazol]-2'-yl)-3H-spiro[2-benzofuran-1,4'-piperidin]-3-one, 1'-(5-hydroxy-4'-oxo-1,3-dihydro-4'H-spiro[indene-2,5'-[1,3]oxazol]-2'-yl)-3H-spiro[2-benzofuran-1,4'-piperidin]-3-one, 1'-[(2R)-5-methyl-4'-oxo-1,3-dihydro-4'H-spiro[indene-2,5'-[1,3]oxazol]-2'-yl]-3H-spiro[2-benzofuran-1,4'-piperidin]-3-one, 2'-(1'H,3H-spiro[2-benzofuran-1,4'-piperidin]-1'-yl)-1,3-dihydro-4'H-spiro[indene-2,5'-[1,3]oxazol]-4'-one, 2'-(3-methyl-1'H,5H-spiro[furo[3,4-b]pyridine-7,4'-piperidin]-1'-yl)-1,3-dihydro-4'H-spiro[indene-2,5'-[1,3]oxazol]-4'-one, 2'-(3-methyl-1'H,7H-spiro[furo[3,4-b]pyridine-5,4'-piperidin]-1'-yl)-1,3-dihydro-4'H-spiro[indene-2,5'-[1,3]oxazol]-4'-one, 2'-(5,5-dimethyl-1'H,5H-spiro[furo[3,4-b]pyridine-7,4'-piperidin]-1'-yl)-1,3-dihydro-4'H-spiro[indene-2,5'-[1,3]oxazol]-4'-one, 2'-(6-methyl-1H, 1'H-spiro[furo[3,4-c]pyridine-3,4'-piperidin]-1'-yl)-1,3-dihydro-4'H-spiro[indene-2,5'-[1,3]oxazol]-4'-one, 2'-(7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one, 2'-(7,7-dimethyl-1'H,7H-spiro[furo[3,4-b]pyridine-5,4'-piperidin]-1'-yl)-5-hydroxy-1,3-dihydro-4'H-spiro[indene-2,5'-[1,3]oxazol]-4'-one, 3-methyl-1'-(4'-oxo-1,3-dihydro-4'H-spiro[indene-2,5'-[1,3]oxazol]-2'-yl)-5H-spiro[furo[3,4-b]pyridine-7,4'-piperidin]-5-one, 3-methyl-1'-(4'-oxo-1,3-dihydro-4'H-spiro[indene-2,5'-[1,3]oxazol]-2'-yl)-7H-spiro[furo[3,4-b]pyridine-5,4'-piperidin]-7-one, 5,6-difluoro-2'-(1'H,3H-spiro[2-benzofuran-1,4'-piperidin]-1'-yl)-1,3-dihydro-4'H-spiro[indene-2,5'-[1,3]oxazol]-4'-one, 5,6-dihydroxy-1'-(4'-oxo-1,3-dihydro-4'H-spiro[indene-2,5'-[1,3]oxazol]-2'-yl)-3H-spiro[2-benzofuran-1,4'-piperidin]-3-one, 5-fluoro-1'-(4'-oxo-1,3-dihydro-4'H-spiro[indene-2,5'-[1,3]oxazol]-2'-yl)-3H-spiro[2-benzofuran-1,4'-piperidin]-3-one, 5-hydroxy-1'-(4'-oxo-1,3-dihydro-4'H-spiro[indene-2,5'-[1,3]oxazol]-2'-yl)-3H-spiro[2-benzofuran-1,4'-piperidin]-3-one, 6-hydroxy-1'-(4'-oxo-1,3-dihydro-4'H-spiro[indene-2,5'-[1,3]oxazol]-2'-yl)-3H-spiro[2-benzofuran-1,4'-piperidin]-3-one, and 6-methyl-1'-(4'-oxo-1,3-dihydro-4'H-spiro[indene-2,5'-[1,3]oxazol]-2'-yl)-1H-spiro[furo[3,4-c]pyridine-3,4'-piperidin]-1-one, or a pharmaceutically acceptable salt thereof.

11. A compound selected from the group consisting of

2'-(1'H,3H-spiro[2-benzofuran-1,4'-piperidin]-1'-yl)-1,3-dihydro-4'H-spiro[indene-2,5'-[1,3]oxazol]-4'-one, 1'-(4'-oxo-1,3-dihydro-4'H-spiro[indene-2,5'-[1,3]oxazol]-2'-yl)-3H-spiro[2-benzofuran-1,4'-piperidin]-3-one, 2'-(6-methyl-1H,1'H-spiro[furo[3,4-c]pyridine-3,4'-piperidin]-1'-yl)-1,3-dihydro-4'H-spiro[indene-2, ]oxazol]-4'-one, 2'-(3-methyl-1'H,5H-spiro[furo[3,4-b ]pyridine-7,4'-piperidin]-1'-yl)-1,3-dihydro-4'H-spiro[indene-2,5'-[1,3]oxazol]-4'-one, and 2'-(3-methyl-1'H,7H-spiro[furo[3,4-b ]pyridine-5,4'-piperidin]-1'-yl)-1,3-dihydro-4'H-spiro[indene-2,5'41,3]oxazol]-4'-one, or a pharmaceutically acceptable salt thereof.

12. The compound 2'-(7,7-dimethyl-1'H,7H-spiro[furo[3,4-b]pyridine-5,4'-piperidin]-1'-yl)-1,3-dihydro-4'H-spiro[indene-2,5'-[1,3]oxazol]-4'-one, or a pharmaceutically acceptable salt thereof.

13. A pharmaceutical composition comprising a compound of claim 1 and a pharmaceutically acceptable carrier and/or a pharmaceutically acceptable auxiliary substance.

* * * * *